(12) United States Patent
Mao et al.

(10) Patent No.: US 6,548,302 B1
(45) Date of Patent: Apr. 15, 2003

(54) POLYMERS FOR DELIVERY OF NUCLEIC ACIDS

(75) Inventors: Hai-Quan Mao, Towson, MD (US); Kevin Y. Lin, Placentia, CA (US); Bart S. Hendriks, Cambridge, MA (US); Kam W. Leong, Ellicott City, MD (US); Michael F. Haller, Baltimore, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/336,390

(22) Filed: Jun. 18, 1999

Related U.S. Application Data

(60) Provisional application No. 60/089,699, filed on Jun. 18, 1998.

(51) Int. Cl.⁷ .................. A61K 48/00; A61K 9/127; C12N 15/85; C12N 5/00; C12N 15/63

(52) U.S. Cl. .................. 435/455; 424/450; 435/325; 435/375; 514/44

(58) Field of Search .................. 424/450; 435/6, 435/325, 69.1, 455, 375; 514/44; 510/468; 436/829

(56) References Cited

U.S. PATENT DOCUMENTS

| | | |
|---|---|---|
| 3,857,931 A | 12/1974 | Hager |
| 3,887,699 A | 6/1975 | Yolles |
| 3,927,231 A | 12/1975 | Desitter et al. |
| 3,932,566 A | 1/1976 | Reader |
| 4,259,222 A | 3/1981 | Login et al. |
| 4,293,539 A | 10/1981 | Ludwig et al. |
| 4,315,847 A | 2/1982 | Login et al. |
| 4,315,969 A | 2/1982 | Login et al. |
| 4,638,045 A | 1/1987 | Kohn et al. |
| 4,741,872 A | 5/1988 | De Luca et al. |
| 4,818,542 A | 4/1989 | DeLuca et al. |
| 5,075,109 A | 12/1991 | Tice et al. |
| 5,099,060 A | 3/1992 | Kohn et al. |
| 5,104,947 A | 4/1992 | Schacht et al. |
| 5,160,745 A | 11/1992 | DeLuca et al. |
| 5,176,907 A | 1/1993 | Leong |
| 5,194,581 A | 3/1993 | Leong |
| 5,219,564 A | 6/1993 | Zalipsky et al. |
| 5,256,765 A | 10/1993 | Leong |
| 5,407,609 A | 4/1995 | Tice et al. |
| 5,460,831 A | 10/1995 | Kossovsky et al. |
| 5,530,093 A | 6/1996 | Engelhardt et al. |
| 5,531,925 A | 7/1996 | Landh et al. |
| 5,580,575 A | 12/1996 | Unger et al. |
| 5,580,859 A | 12/1996 | Felgner et al. |
| 5,626,863 A | 5/1997 | Hubbell et al. |
| 5,759,582 A | 6/1998 | Leong et al. |
| 5,783,567 A | 7/1998 | Hedley et al. |
| 5,861,159 A | 1/1999 | Pardoll et al. |
| 5,869,103 A | 2/1999 | Yeh et al. |
| 5,912,225 A | 6/1999 | Mao et al. |
| 5,932,241 A * | 8/1999 | Gorman .................. 424/450 |
| 5,952,451 A | 9/1999 | Zhao |
| 6,008,318 A | 12/1999 | Zhao et al. |
| 6,166,173 A | 12/2000 | Mao et al. |

FOREIGN PATENT DOCUMENTS

| | | |
|---|---|---|
| CA | 597473 | 5/1960 |
| CA | 2126685 | 5/1994 |
| EP | 248 531 A2 | 12/1987 |
| EP | 266 119 B1 | 5/1988 |
| EP | 0 386 757 | 9/1990 |
| EP | 0 386 757 B1 | 9/1990 |
| EP | 0 386 757 A2 | 9/1990 |
| EP | 467 389 A3 | 1/1992 |
| EP | 467 389 A2 | 1/1992 |
| EP | 635 261 B1 | 1/1995 |
| EP | 706 792 A1 | 4/1996 |
| WO | WO 94/04171 | 3/1994 |
| WO | WO 94/09898 | 5/1994 |
| WO | WO 94/23699 | 10/1994 |
| WO | WO 94/23738 | 10/1994 |
| WO | WO 94/28873 | 12/1994 |
| WO | WO 94/28874 | 12/1994 |
| WO | WO 95/07072 | 3/1995 |
| WO | WO 95/17167 | 6/1995 |
| WO | WO 95/20660 | 8/1995 |
| WO | WO 95/24929 | 9/1995 |
| WO | WO 95/35097 | 12/1995 |
| WO | WO 96/00295 | 1/1996 |
| WO | WO 96/02655 | 2/1996 |
| WO | WO 96/11671 | 4/1996 |
| WO | WO 96/29998 | 10/1996 |
| WO | WO96/40963 | * 12/1996 |
| WO | WO 97/40085 | 10/1997 |
| WO | WO 98/42330 | 10/1998 |
| WO | WO/9844020 | 10/1998 |
| WO | WO 98/44021 | 10/1998 |
| WO | WO 98/46286 | 10/1998 |
| WO | WO 98/48859 | 11/1998 |
| WO | WO 98/58012 | 12/1998 |
| WO | WO 00/19976 | 4/2000 |
| WO | WO 00/41678 | 7/2000 |

OTHER PUBLICATIONS

Chaubal et al. (2000), Accelerated Hydrolysis and Erosion Studies of In Vitro Degradation of Prolilactofates, Proceed. Intl. Symp. Control. Rel. Bioact. Mater. 27:656.

(List continued on next page.)

*Primary Examiner*—Sean McGarry
*Assistant Examiner*—Janet Epps
(74) *Attorney, Agent, or Firm*—Foley Hoag, LLP; Kingsley L. Taft; James T. Olesen

(57) ABSTRACT

The present invention relates to compositions and methods for delivery of nucleic acids. In particular, the invention provides a polymeric delivery formulation including a nucleic acid to be transfected into a host cell, formulated in a biodegradable polymer having phosphorous-based linkages.

29 Claims, 12 Drawing Sheets

OTHER PUBLICATIONS

Mao et al. (1999), Biodegradable Polymers: Poly (Phosphoester)s, Encyclo. Controlled Drug Delivery, Wiley & Sons, p. 45–60, Jul. 1999.

Mao et. al. (1998), Intramuscular Delivery of LacZ Plasmid Encapsulated in Microspheres Composed of Biogradable Phosphate Chain–Extended Poly (L–lactide), Proceed. Intl. Symp. Control. Rel. Bioact. Mater. 25:203.

Vinogradov et al. (1996), *Block Polycationic Oligonucleotide Derivative: Synthesis and Inhibition of herpes Virus Reproduction,* Bioconjugate Chem. vol. 3, pp. 3–6.

Mao et al., "Design of New Biodegradable Polymers Based on Chain–Extension of Oligomeric Lactides by Phosphates," Proceedings of the Topical Conference on Biomaterials Carriers for Drug Delivery and Scaffold for Tissue Engineering, pp. 193–195, Nov. 1997.

Mao et al., "Biodegradable Copolymer for Drug Delivery: Poly(phosphate–terephthalate)s," Proceedings of the Topical Conference on B iomaterials Carriers for Drug Delivery and Scaffold for Tissue Engineering, pp. 141–143, Nov. 1997.

Alpar et al., "Potential of Particulate Carriers for the Mucosal Delivery of DNA Vaccines," Biochemical Society Transactions 25 (2):347 (1997).

Gorecki and Simons, "The Dangers of DNA Vccination," Nature Medicine 5 (2): 126–127 (Feb. 1999).

Jones et al., "Poly(DL–lactide–Co–glycolide)–encapsulated plasmid DNA Elicits Systemic and Mucosal Antibody Responses to Encoded Protein after Oral Administration", Vaccine vol. 15 (8): pp. 814–817 (1997).

Langer et al., "Biocompatibility of Polymeric Delivery Systems for Macromolecules", Journal of Biomedical Materials Research 15:267–277 (1981).

O'Hagan, Derek T., "Recent Advances in Vaccine Adjuvants for Systemic and Mucosal Administration", J. Pharm. Pharmacol. 49: 1–10 (Sep. 15, 1997).

Pec et al., "Biological Activity of Urease Formulated in Poloxamer 407 after Intraperitoneal Injection in the Rat", Journal of Pharmaceutical Sciences 81 (7):626–630 (1992).

Pardoll, Drew M., "Paracrine Cytokine Adjuvants in Cancer Immunotherapy", Annu. Rev. Immunol. 13:399–415 (1995).

Pretula et al., "High–molecular–weight poly(alkylene phosphonate)s by condensation of dialkylphosphonates with diols," Die Makromolekulare Chemie 191:671–680 (1990).

Rhine et al., "Polymers for Sustained Macromolecule Release: Procedures to Fabricate Reproducible Delivery Systems and Control Release Kinetics," Journal of Pharmaceutical Sciences 69 (3):265–270 (1980).

Wloch et al., "The Influence of DNA Sequence on the Immunostimulatory Properties of Plasmid DNA Vectors," Human Gene Therapy 9:1439–1447 (Jul. 1, 1998).

Tomlinson et al., "Controllable gene theraphy Pharmaceutics of non–viral gene delivery systems," Journal of Controlled Release 39:357–372 (1996).

Lewis et al., "Biodegradable poly (L–lactic acid) matrices for the sustained delivery of antisense oligonucleotides," Journal of Controlled Release, 37:173–183 (1995).

Hedley, M., "Genetic Modulation of Antigen Presentation," MHC Molecules: Expression, Assembly and Function, Ch. 17, pp. 281–293; Editors, Robert G. Urban and Roman M. Chicz; published by R.G. Landes & Co. (1996).

Gref et al., "Biodegradable Long–Circulating Polymeric Nanospheres," Science, 263:1600–1603 (1994).

Jones et al., "Immune Responses Following Oral and Parenteral Administration of Plasmid DNA Encapsulated in Poly(lactide–coglycolide) Microparticles, " (Abstract) Int'l Meeting on Nucleic Acid Vaccines, Bethesda, MD (1996).

Heard, R., "HLA and autoimmune disease," HLA & Disease, pp. 123–151 (1994).

Beer et al., "Extended release of adenovirus from polymer microspheres: potential use in gene therapy for brain tumors," Advanced Drug Delivery Reviews, 27:59–66 (1997).

Amagai et al., "Autoantibodies against a Novel Epithelial Cadherin in *Pemphigus Vulgaris,* a Disease of Cell Adhesion," Cell 67:869–877 (1991).

Kadiyala et al., "Poly(phosphoesters): Synthesis, Physicochemical Characterization and Biological Response," Biomedical Applications of Synthetic Biodegradable Polymers, Chapter 3, pp. 33–57 (1995).

Weiner et al., "Genetic Vaccines," Scientific American pp. 50–57 (Jul. 1999).

Bruin et al., "Biodegradable lysine diisocyanate–based poly(glycolide–co–ε–caprolactone)–urethane network in artificial skin," Biomaterials, 11(4):291–295 (1990).

Chien, Y.W., "Controlled–Release Drug Administration: Logic," Novel Drug Delivery Systems (1982) pp. 1–11.

Choueka et al., "Canine bone response to tyrosine–derived polycarbonates and poly(L–lactic acid)," Journal of Biomedical Materials Research, 31:35–41 (1996).

Ertel et al., "Evaluation of poly(DTH carbonate), a tyrosine–derived degradable polymer, for orthopedic applications," Journal of Biomedical Materials Research, 29:1337–1348 (1995).

Langer et al., "Controlled Release of Bioactive Agents," Rev. Macro. Chem. Phys., C23(1), pp. 62–125 (1983).

Langer, Robert, "New Methods of Drug Delivery," Science, 249:1527–1533 (1990).

Leong et al., "Polyanhydrides for controlled release of bioactive agents," Biomaterials, 7:364–371 (1986).

Leong et al., "Polymeric controlled drug delivery," Advanced Drug Delivery Reviews, 1:199–233 (1987).

Penczek et al., "Phosphorous–Containing Polymers," Handbook of Polymer Synthesis, Part B, Chapter 17, pp. 1077–1132 (1992).

Pulapura et al., "Trends in the Development of Bioresorbable Polymers for Medical Applications," Journal of Biomaterials Applications, 6:216–250 (1992).

* cited by examiner 1. 1 hr
2. 2 days
3. 6 days
4. 8 days
5. 10 days
6. 12 days
7. 19 days
8. 25 days
9. Molecular weight market: λ-DNA HindIII digested.
10. Plasmid DNA (p43-LacZ)

POLYMERS FOR DELIVERY OF NUCLEIC ACIDS

RELATED APPLICATION INFORMATION

This Application claims the benefit of priority under 35 U.S.C. §119(e) to Provisional Application No. 60/089,699, filed Jun. 18, 1998, the specification of which is incorporated by reference in its entirety.

ACKNOWLEDGEMENT OF GOVERNMENT RIGHTS

This invention was made with support from the U.S. Government under a grant from the National Cancer Institute. The U.S. Government has certain rights in this invention.

INTRODUCTION

1. Biocompatible Polymers

Biocompatible polymeric materials have been used extensively in therapeutic drug delivery and medical implant device applications. In certain applications, it may be desirable for such polymers to be not only biocompatible, but also biodegradable.

A biocompatible, biodegradable polymer is one effective means of delivering a therapeutic agent or other biologically active substance. See generally Langer et al., (1983) *Rev. Macro. Chem. Phys.* C23(1):61. Polymers have been used as carriers of therapeutic agents to effect a localized and sustained release. See generally *Controlled Drug Delivery*, Vols. I and II; Bruck et al., eds. (1982); and Chien et al., (1982) *Novel Drug Delivery Systems*. Such delivery systems may provide enhanced therapeutic efficacy and reduced overall toxicity.

Typically, a biodegradable matrix not only allows for diffusional release of any therapeutic or other agent, but also allows for controlled release of such agent by degradation of the polymer matrix. Specific examples of biodegradable materials that have been used, or proposed for such use, include: polylactide, polyglycolide, polydioxanone, poly(lactide-co-glycolide), poly(glycolide-co-polydioxarone), polyanhydride, poly(glycolide-co-trimethylene carbonate), and poly(glycolide-co-caprolactone).

Polymers having phosphorous linkages are known. Some respective structures of such polymers, each of which have a different sidechain connected to the phosphorus atom, are:

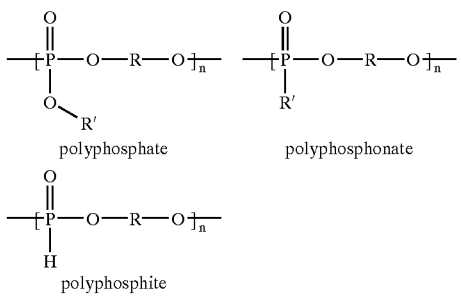

In part, the present invention provides biocompatible polymers having phosphorous-based linkages and related compositions and formulations, and methods for using them.

2. Gene Therapy

Somatic gene therapy may be defined, in part, as the ability to cause ectopic expression of a gene in non-germ line cells of an animal or patient by the introduction of foreign nucleic acid. In general, gene therapy may be divided into two categories. Ex vivo gene therapy typically involves the removal of cells from a host organism, introduction of a foreign gene or other nucleic acid into those cells in the laboratory, and reimplantation or transplantation of the modified cells back into a recipient host. In contrast, in vivo gene therapy generally involves the introduction of a foreign gene or other nucleic acid directly into cells of a recipient host without the need for prior removal of those cells.

A. Gene Therapy in Cardiac Myocytes

The ability to program gene expression in cardiac myocytes may enable the treatment of a number of inherited, acquired or other cardiac diseases. Applications of this approach may be divided into several general categories, two of which are described in more detail below As many as 1.5 million patients per year in the U.S. suffer a myocardial infarction (MI). Many millions more suffer from syndromes of chronic myocardial ischemia due to large and small vessel coronary atherosclerosis. Many of these patients may benefit from the ability to stimulate collateral vessel formation in areas of ischemic myocardium. Such a result may be achieved, for example, by injecting plasmids encoding recombinant angiogenesis factors directly into the left ventricular wall to stimulate new collateral circulation in areas of chronically ischemic myocardium. Also, this approach maybe used to study directly the molecular mechanisms regulating cardiac myocyte gene expression both during cardiac myogeneses and in a variety of pathophysiologic states such as cardiac hypertrophy. Gene therapy methods may provide an alternative approach to the current methods of coronary artery bypass and percutaneous transluminal coronary angioplasty. For certain patients having severe and diffuse atherosclerosis that they are not candidates for bypass or angioplasty.

A number of genetic disorders affect myocardial performance. For example, many patients with Duchenne's muscular dystrophy also suffer from a cardiomyopathy. In addition, it is clear that there are a number of other genetically-inherited cardiomyopathies of unknown etiology. Gene therapy approaches may be useful in treating a variety of these inherited disorders of cardiac function. For example, injection of vectors containing the normal dystrophin gene or cDNA, or their functional equivalent, may correct the defect in patients with Duchenne's muscular dystrophy. In part, the present invention provides gene therapy compositions for treatment of disorders affecting myocardial and other muscle tissues.

B. Gene Therapy Using Skeletal Myoblasts

A variety of acquired and inherited diseases are currently treated by intravenous or subcutaneous infusions of recombinant or purified proteins as needed. Some examples include diabetes mellitus, which may be treated with subcutaneous or intravenous injections of insulin, hemophilia A, which may be treated with intravenous infusions of factor VIII, and pituitary dwarfism, which may be treated with subcutaneous injections of growth hormone. The development of expression systems that may produce and deliver such recombinant proteins into the systemic circulation represents an important advance in treatment of such diseases.

In certain instances, the recombinant protein delivery system may utilize muscle cells isolated from the recipient, which are grown and transduced with one or more recombinant genes in vitro, and reimplanted into the host organism. Such cells may be engineered to produce large amounts of secreted recombinant protein, which, following secretion, may be circulated.

In part, the present invention provides formulations of gene expression constructs for transfecting skeletal muscle stem cells (myoblasts) to produce therapeutic levels of serum proteins in a recipient host. In one embodiment, for example, myocytes are engineered to secrete recombinant proteins in the myocardium.

3. Genetic Immunization

One means of evoking an immune response involves DNA-based immunization. In one aspect, such immunization involves introducing plasmid DNA, containing protein coding sequences and the necessary regulatory elements to express them, into tissues of the organism by means of a parenteral injection of a simple saline solution. Such application of plasmid DNA to muscular tissues has been shown to lead to transgene expression. DNA immunization may elicit both antibody and cell-mediated immune responses, thereby generating protective immunity.

One aspect typically inherent to this means of immunization is that the immunizing molecule, usually plasmid DNA, is often not highly immunogenic. It appears that some features of DNA-based immunization do mimic, at least in part, the immune response induced by a viral infection. For example antigen presentation by molecules of the major histocompatibility complex (MHC) class I pathway may take place, thus leading to the induction of cytotoxic T lymphocytes.

In part, the present invention presents improved DNA vaccinations, and methods of using them.

SUMMARY OF THE INVENTION

Design of controlled release systems and tissue engineering scaffolds continues to stimulate development of new biodegradable polymers. Polymers having phosphate linkages in the backbone have shown promise because of their structural versatility and attractive physico-chemical properties. The present invention is directed in part to the discovery of a polymer system for nucleic acid transfer into muscle and other tissue both in vitro and in vivo. In certain instances, the subject formulations may be used to effectuate both stable and transient transfection of cells. The subject formulations may provide prolonged transgene expression even under transient conditions and in non-dividing cells. In addition, the subject formulations are useful as DNA vaccinations.

In one aspect, the present invention is directed to a polymer formulation or system, methods for treatment using such system, and precursors of the polymer system, such as a liquid composition, all for delivery of nucleic acid and other materials.

In another aspect, the present invention relates to compositions and methods for delivery of nucleic acids in vivo. In one aspect, the present invention provides a polymeric delivery formulation including a nucleic acid to be transfected, formulated in a biodegradable polymer having phosphorous-based linkages. In certain embodiments, such linkages are comprised of poly(phosphoester)s or derivatives or analogs thereof. In other embodiments of the present invention, the polymer matrix, loaded with one or more substances such as nucleic acid or therapeutic agent, may be prepared as a microsphere for use.

The versatility of the polymers of the present invention results in part from the versatility of the phosphorus atom, which is known for a multiplicity of reactions. The physico-chemical properties of the phosphorous linkage may be readily manipulated, in part, by varying substituents attached to the phosphorous atom. In certain embodiments, the degradation observed for any polymer in vivo is due in large part to the physiologically labile phosphoester bond (or other analogs or derivatives thereof) in the backbone of the polymer. By manipulating the backbone or other substituents, a wide range of degradation rates may be attained.

The gene delivery system of the present invention, and methods of using such system, have a variety of attractive features, some of which include the following: (i) ligands may be conjugated to the DNA-nanosphere for potential tissue targeting and to stimulate receptor-mediated endocytosis; (ii) lysosomolytic agents may be incorporated to promote escape of DNA from endosomal and lysosomal compartments; (iii) bioavailability of the DNA may be improved because of protection from serum nuclease degradation by the polymer matrix; (iv) other bioactive agents such as proteins, multiple plasmids, or drugs may be co-encapsulated in the formulations; and (v) prolonged gene expression may allow for a single dose DNA vaccine.

This polymeric system may be administered as is necessary depending on the subject being treated, the severity of the affliction, the judgment of the prescribing physician, and the like.

DETAILED DESCRIPTION OF THE INVENTION

1. Overview

Figure 1:
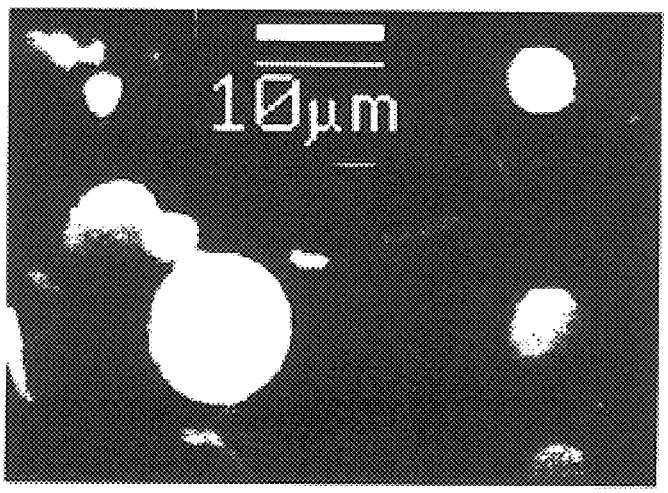
FIG. 1: EM image of microsphere A.

In one aspect, the present invention provides a polymeric delivery formulation including a transfectable nucleic acid formulated in a biodegradable polymer comprised of poly(phosphoester)s or derivatives thereof The subject method may be practiced using biodegradable polymers having phosphorous-based linkages, such as a variety of different types of poly(phosphoester)s or derivatives thereof. The diversity in the polymers contemplated by present invention allows the selection of physical and functional characteristics.

In certain embodiments, certain polymers of the subject invention include one or more subunits of general formula (XV):

Formula XV wherein, independently for each occurrence:
 $Q_1$ represents O or S;
 $Q_2$ represents O, S or NR';
 X represents O, S or NR';
 R' represents H or alkyl;
 R represents an organic or organometallic moiety, e.g., a substituted or unsubstituted cyclic, branched or straight chain aliphatic group of 2 to about 10 bonds in length, including alkyls, alkenyls, cycloalkyls, cycloalkenyls, alkynyls, aryls, heteroalkyls, or heteroaryl moieties;
 R1 represents hydrogen, alkyl, —O-alkyl, —O-cycloalkyl, aryl, —O-aryl, heterocycle, —O-heterocycle, —S—$R_4$, —O—(C=O)—$R_4$, —Cl or —N($R_2$)$R_3$;
 $R_2$ and $R_3$, each independently, represent a hydrogen, an alkyl, an alkenyl, —(CH$_2$)$_n$—$R_4$, or $R_2$ and $R_3$ taken together with the N atom to which they are attached complete a heterocycle having from 4 to about 8 atoms in the ring structure; and,
 $R_4$ represents a hydrogen, aryl, cycloalkyl, cycloalkenyl, heterocycle or polycycle.

In certain embodiments, "n" in formula XV range from about 5 to about 500 or more. Alternatively, in other embodiments, "n" may be about 10, 25, 50, 75, 100, 150, 200, 300, or 400.

In another aspect, the present invention is directed to a formulation or composition including a biodegradable polymer having phosphorous-based linkages formulated with nucleic acid for transfection, vaccination, or other purposes, and method of using the same.

In one embodiment, the subject transfection system is based on biodegradable poly(phosphate-terephthalate) copolymers with a chemical structure analogous to that of Dacron. In other embodiments, the polymer is based on poly(alpha-hydroxy acids), such as poly(lactide-co-glycolide)s (PLGA). In still other embodiments, the present invention provides a biodegradable paste composed of a polyphosphate synthesized by the solution polycondensation of trans-1,4-cyclohexane dimethanol and hexyl phosphorodichloridate or the like. The various a polymeric systems that may be used in the subject method allow the degradative, thermal, and mechanical properties of the polymers to be manipulated. As a result, the biocompatibility and biodegradability characteristics of the polymer systems of the present invention may be modified as needed.

To further illustrate, in certain embodiments the polymeric compositions of the present invention comprise a nucleic acid formulated, such as in the form of microspheres, in a polymeric system having one or more recurring monomeric elements in the polymer represented in general formula (I) or (II):

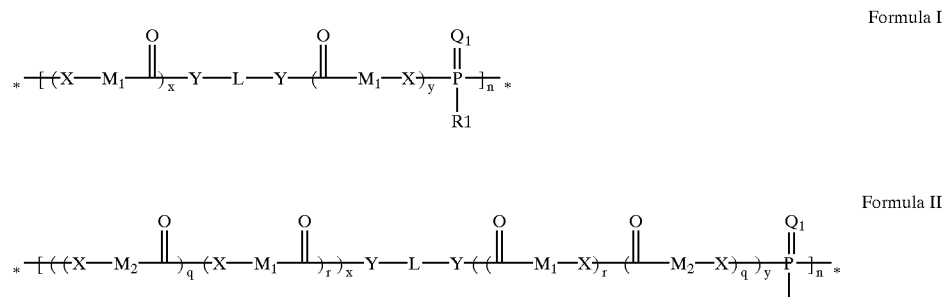

Formula I

Formula II wherein, independently for each occurrence:
 $Q_1$ represents O or S;
 X represents O, S or NR';
 R' is H or alkyl;
 R1 represents hydrogen, alkyl, —O-alkyl, aryl, —O-aryl, heterocycle, —O-heterocycle, or —N($R_2$)$R_3$;
 $R_2$ and $R_3$, each independently, represent a hydrogen, an alkyl, an alkenyl, —(CH$_2$)$_p$—$R_4$, or $R_2$ and $R_3$, taken together with the N atom to which they are attached, complete a heterocycle having from 4 to about 8 atoms in the ring structure;
 $R_4$ represents an aryl, a cycloalkyl, a cycloalkenyl, a heterocycle or a polycycle;
 L represents any divalent branched or straight chain aliphatic group having from 1 to about 20 carbon atoms;
 $M_1$ and $M_2$ are each, independently, (i) a branched or straight chain aliphatic group having from 1 to about 20 carbon atoms, or (ii) a branched or straight chain, oxy-carboxy, or amino-aliphatic group having from 1 to about 20 carbon atoms;
 p is zero or an integer from 1 to about 10; and,
 molar ratio of x:y is about 1, molar ratio of n:(x or y) is between about 200:1 and about 1:200, and molar ratio of q:r is between about 1:99 and about 99:1.

In the above formulas, and others used herein, "*" represents another monomeric unit of the polymer, which may be the same or different from the monomeric unit to which "*" is attached, and may be a chain terminating group (.g., a hydrogen or hydroxyl-protecting group) as appropriate.

In certain embodiments, at least about 10 percent to 100 percent of the polymer may be composed of monomeric elements having the structures depicted by the formulas herein. In other embodiments of the present invention, at least about 25, 50, 75, 85, 90 or 95 percent of the polymer may be composed of such repetitive elements. For example, for a polymer having units depicted in Formula I, at least about 10 percent to 100 percent of the polymer may be composed of monomeric elements having the structures depicted by such formula, and in other embodiments of the present invention, at least about 25, 50, 75, 85, 90 or 95 percent of the polymer may be composed of such repetitive subunits.

In certain embodiments, substituents of the polymeric chain, such as any of R1–R4, may be selected to permit additional inter-chain cross-linking by covalent or electrostatic (including hydrogen-binding or the formation of salt bridges), e.g., by the use of a sidechain appropriately substituted.

In certain embodiments, the polymeric chains of the subject compositions have molecular weights of from at least about 5,000 daltons to about 1,000,000 daltons or more, or alternatively about 8,000, 10,000, 15,000, 25,000, 50,000, or 75,000. In other embodiments, the polymers of the present invention are at least about 100,000 daltons, at least about 250,000 daltons, or at least about 500,000 daltons. Alternatively, the polymers of the present invention may range in molecular weight from about 2,000 to about 1,000,000, and may contain from about 10 to about 10,000 monomeric units.

In any of the subject polymers, a variety of material may be incorporated. For example, the present invention contemplates incorporating nucleic acid into the polymer matrix. In other instances, materials that serve as adjuvants may be associated with the polymer matrix. A combination of more than one nucleic acid with either additional nucleic acids or other therapeutic agents may be incorporated into the compositions of the present invention. Such multiple incorporation may take advantage of a variety of techniques, such as physical dispersion in the polymer matrix of one component, and pendant attachment of another.

The amount of nucleic acid desirable in the polymer matrix of the present invention will often vary with a number of factors, including: (i) the nature of the nucleic acid; (ii) the polymer's intended use, including any desired therapeutic effect for in vivo use; (iii) the means of incorporation of any nucleic acid or other material; and (iv) the chemical and physical properties of the polymer matrix, including the degradation rate under different conditions. The loading level for a composition of the invention may vary, for example, on whether the nucleic acid or other material to be incorporated is pendantly attached, or alternatively physically dispersed. For those compositions in which the nucleic acid and other material is physically dispersed within or on the polymer matrix, the concentration of typically does not exceed 50 weight %. For compositions in which the nucleic acid or other material is pendantly attached to the polymer matrix, the loading level is up to the stoichiometric ratio of nucleic acid or other material per monomeric unit of the polymer suited for such attachment.

In certain embodiments, the amount of nucleic acid loaded in any microsphere ranges from about 0.05 to about 10 weight percent, or 0.1, 0.25, 0.5, 0.75, 1.0, 1.5, 2.0, 3.0, 4.0, 5.0, 6.0, 7.0, 8.0, and 9.0. For example, a nucleic acid loaded at a 2% level means that there is 2 mg of DNA per 100 mg of microspheres comprised of polymers of the present invention. In other embodiments, the present invention contemplates incorporating a therapeutically effective amount of nucleic acid. In DNA vaccinations using the subject polymer systems, an initial high dose of nucleic acid may prove most effective in producing an immunogenic response.

In addition to nucleic acids, other materials may be incorporated into the polymer matrix. Such additional materials may affect the characteristics of the polymer matrix that results. For example, fillers, such as bovine serum albumin (BSA) or mouse serum albumin (MSA) may be associated with the microspheres of the polymer matrix. In certain embodiments, when incorporated in combination with nucleic acid, the amount of filler may range from about 1 to about 100 times or more the amount of nucleic acid, by weight, or a ratio of about 2.5, 5, 10, 25, 50, 75 weight filler to nucleic acid. For example, if 1 mg of nucleic acid is loaded into 1 gm of polymer matrix, the filler may be about 1 mg to about 100 mg in weight. As expressed in terms of percent loading, for a nucleic acid load level of 0.1%, a filler would amount to about 0.1% to 10% or more.

Incorporation of such fillers may affect the release rate of any nucleic acid also incorporated into the polymer matrix. For example, nucleic acid was observed to release at a higher rate from P(DAPG-EOP) in which BSA was also incorporated. Other fillers known to those of skill in the art, such as carbohydrates, sugars, saccharides, and polysaccharides, including mannitose and sucrose, may be used in certain embodiments in the present invention.

Alternatively, materials that produce a therapeutic effect may be incorporated into the polymer matrix. U.S. Pat. No. 5,256,765 discloses a variety of such bioactive substances. For example, the co-encapsulation of one or more cytokines, such as IFN-γ and IL-4, may affect the immunogenic response afforded any nucleic acid also associated with the polymer matrix. The amount of any such therapeutic agent to be loaded into any polymer matrix will depend on a variety of factors, including the nature of the therapeutic agent, the polymer matrix, whether there are any other nucleic acid or materials incorporated, and the like. For any therapeutic agent, the present invention contemplates incorporating a therapeutically effective amount of such agent. In other embodiments, the amount of such therapeutic agent may range from about 0.005% up to about 25%, or alternatively 0.01, 0.05, 0.1, 0.25, 0.5, 1.0, 2.5, 5.0, 10, 15 or 20%. For example, a therapeutic agent loaded at a 2% level means that there is 2 mg of such agent per 100 mg of polymer matrix.

In another aspect, the present invention contemplates loading more than two different substances into any polymer matrix. In certain embodiments, three, four, five or more nucleic acids, therapeutic agents, fillers, or other materials or bioactive substances may be incorporated or associated with any polymer matrix. For example, a polymer matrix may be prepared incorporating nucleic acid and two other materials, such as one filler and one therapeutic agent.

Alternatively, for example, a polymer matrix may be prepared having nucleic acid and two or more therapeutic agents.

In another aspect, subunits of polymers of the present invention may contain functional groups which allow the chemical linkage of nucleic acids or other materials to the polymers. For example, nucleic acid may be coupled to a hydroxyl group of a subunit in the polymer via a phosphate linkage. The rate of nucleic acid release will depend in part on the hydrolytic cleavage of the conjugate. One feature of this delivery system is the possibility of attaining high nucleic acid loading levels.

The means by which any material, including nucleic acid, is incorporated into the polymer matrix may affect its release rate. When the nucleic acid or other material is not bound to the matrix, then it is generally physically dispersed within or on the surface of the polymer matrix. When the nucleic acid is pendantly attached to the polymer, it is usually attached though a bonding linkage, for example, by ionic or covalent bonding, often to a sidechain present in at least some of the subunits of the polymer. In the first instance, nucleic acid and other material are typically released as the matrix degrades. Release from the surface of the polymer matrix may also occur in certain embodiments. In the pendant system, the nucleic acid is usually released as the polymer-nucleic acid bond is cleaved during use, often in vivo. Other materials may be pendantly attached to the polymer as well and released upon use.

In certain embodiments, the phosphate bond also provides a reactable side chain that allows conjugation of functional groups of interest, such as targeting ligands. In this manner, polymers of the present invention may be targeted to cells of interest, e.g., the M cells of the Peyer's patches which are responsible for the uptake of microparticles such as the microspheres of the present invention.

According to the present invention, the polymers and blends thereof may be used as a pharmaceutical carrier in a gene delivery matrix, e.g., to form a polymeric system for delivery and in vivo transfection by nucleic acid, such as a recombinant nucleic acid. One potential feature of the subject polymeric formulations is that, because the subject delivery systems may be formulated with substantially any of a wide range of vectors, issues of size limitations, which may be problematic in viral vectors, may be overcome. Moreover, the choice of vector may reduce other problems associated with the use of viral vectors, such as retroviral vectors or unwanted recombination events. Moreover, the subject formulations may be used to provide long-term transient transfection of cells that are otherwise refractory to many viral vectors. For example, in certain embodiment, the subject delivery system may be used to transfect non-dividing cells such as muscle.

In another aspect, the polymer systems of the present invention may pre used in the manufacture of a medicament for any number of uses, including as a DNA vaccination, those presented herein. In still other aspects, the present invention is directed to a method for formulating compositions or supplements of the present invention in a pharmaceutically acceptable excipient.

Another aspect of the invention is a method for transfecting cells with the subject polymeric formulations. As described herein, exemplary uses of these formulations include gene therapy for correction of genetic defects in the transfected tissue, as well as for the ectopic expression of secreted proteins which act locally or distally relative to the transfected tissue. Furthermore, as described in the appended examples, the subject transfection system may elicit a strong immune response, even at low dose, and may be used to deliver a coding sequence for an antigen(s) as part of a genetic immunization protocol. The subject methods may be used in mammals, including humans, livestock and pets.

When formulated, the polymer matrices of the present invention may be prepared in a variety of different forms. In certain embodiments, the polymer systems may be formed as preparation of stable particles. Particles may be prepared in a range of sizes so as to provide a suitable release rate of any nucleic acid or other material incorporated therein upon use. In certain embodiments, the particles range in size from nanometers to sizes even greater than 1 mm, even exceeding 5 mm or even 10 mm. For example, the particles may be microspheres. In certain embodiments, microspheres range in size from about 2 to about 20 micrometers, or 5, 7, 10 or 15. Alternatively, the particles may be nanospheres. In other embodiments, polymers of the present invention may be formed into capsules, including microcapsules and nanocapsules. A variety of methods are known in the art and may be used to prepare microspheres using polymers of the present invention, including the double emulsion method.

2. Definitions

For convenience, certain terms employed in the specification, examples, and appended claims are collected here. These definitions should be read in light of the rest of the disclosure and understood as by a person of skill in the art.

The term "biocompatible polymer", or "biocompatibility" when used in relation to polymers of the present invention, is used herein to refer to polymers that are neither themselves toxic to the host (e.g., an animal or human), nor degrade (if at all) at a rate that produces monomeric subunits or other byproducts at toxic concentrations in the host. In certain embodiments of the present invention, biodegradation generally involves degradation of the polymer, ultimately, into its monomeric subunits, which are usually known to be effectively non-toxic. Intermediate oligomeric products resulting from such degradation may have different toxicological properties, however. Consequently, in certain embodiments, toxicology of a biodegradable polymer intended for in vivo use, such as implantation or injection into a patient, may be determined after one or more toxicity analyses.

The term "biodegradable" as used herein in relation to polymers, compositions and formulations of the present invention refers to such material that are intended to degrade during use. Biodegradable polymers typically differ from non-biodegradable polymers in that the former may be degraded during use. In certain embodiments, such use involves in vivo use, such as in vivo therapy. In other certain embodiments, such use involves in vitro use. In general, degradation attributable to biodegradability involves the degradation of a biodegradable polymer into its component subunits, which in certain cases may consist of one or more different monomers. Typically, such degradation occurs by cleavage of a bond connecting one or more of subunits of a biodegradable polymer. The degradation rate of a biodegradable polymer often depends in part on a variety of factors, including the chemical identity of the linkage responsible for any degradation, and the molecular weight, crystallinity, biostability, and degree of cross-linking of such polymer. For example, the greater the molecular weight, the higher the degree of crystallinity, and/or the greater the biostability, the biodegradation of any biodegradable polymer is usually slower.

In certain embodiments, if the biodegradable polymer also has a biologically active substance associated with it, the biodegradation rate of such polymer may be characterized by a release rate of the biologically active substance. In such circumstances, the biodegradation rate typically depends on not only the chemical identity and physical characteristics of the polymer, but also the identity of the biologically active substance.

The term "biodegradable polymer having phosphorous-based linkages" is used herein to refer to polymers in which the following substructure is present at least a multiplicity of times in the backbone of such polymer:

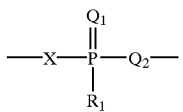

wherein, independently for each occurrence: $Q_1$ represents O or S; $Q_2$ represents O, S or NR'; X represents O, S or NR', R' represents H or alkyl, and R1 is other than —OH, and wherein such substructure is responsible in part for any biodegradability properties of such polymer. In certain embodiments, such biodegradable polymer is non-naturally occurring.

The phrases "parenteral administration" and "administered parenterally" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal and intrastemal injection and infusion.

The term "modulation" as used herein refers to both up regulation (i.e., activation or stimulation) and down regulation (i.e. inhibition or suppression) of a response.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the supplement and not injurious to the patient. Some examples of materials which may serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (II) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrases "systemic administration," "administered systemically," "peripheral administration" and "administered peripherally" mean the administration of a subject supplement, composition, therapeutic or other material other than directly into the central nervous system, such that it enters the patient's system and, thus, is subject to metabolism and other like processes, for example, subcutaneous administration.

The phrase "therapeutically-effective amount" means that amount of nucleic acid or other material that, when incorporated into a polymer of the present invention, produces some desired effect at a reasonable benefit/risk ratio applicable to any medical treatment. In certain embodiments, a therapeutically effective amount of a nucleic acid for in vivo use will likely depend on a number of factors, including: the rate of release of the nucleic acid from the polymer matrix, which will depend in part on the chemical and physical characteristics of the polymer, the identity of the nucleic acid, the mode and method of administration; the nature of the nucleic acid sequence; and any other materials incorporated in the polymer matrix in addition to the nucleic acid.

As used herein, the term "aliphatic" refers to a linear, branched, cyclic alkane, alkene, or alkyne. In certain embodiments, aliphatic groups in the present invention are linear or branched and have from 1 to about 20 carbon atoms.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$–$C_{30}$ for straight chain, $C_3$–$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents may include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls may be further substituted with alkyls, alkenyls, alkoxys, alkylthios, aminoalkyls, carbonyl-substituted alkyls, —$CF_3$, —CN, and the like.

The term "aralkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, alternatively from one to about six carbon atoms in its backbone structure. Likewise, "lower alkenyl" and "lower alkynyl" have similar chain lengths.

The term "heteroatom" as used herein means an atom of any element other than carbon or hydrogen. Illustrative heteroatoms include boron, nitrogen, oxygen, phosphorus, sulfur and selenium, and alternatively oxygen, nitrogen or sulfur.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that may be represented by the general formula:

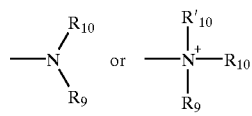

wherein $R_9$, $R_{10}$ and $R_{11}$ each independently represent a hydrogen, an alkyl, an alkenyl, —$(CH_2)_m$—R80, or $R_9$ and $R_{10}$ taken together with the N atom to which they are attached complete a heterocycle having from 4 to 8 atoms in the ring structure; R80 represents an aryl, a cycloalkyl, a cycloalkenyl, a heterocycle or a polycycle; and m is zero or an integer in the range of 1 to 8. In certain embodiments, only one of $R_9$ or $R_{10}$ may be a carbonyl, e.g., $R_9$, $R_{10}$ and the nitrogen together do not form an imide. In other embodiments, $R_9$ and $R_{10}$ (and optionally $R'_{10}$) each independently represent a hydrogen, an alkyl, an alkenyl, or —$(CH_2)_m$—R80. Thus, the term "alkylamine" as used herein means an amine group, as defined above, having a substituted or unsubstituted alkyl attached thereto, i.e., at least one of $R_9$ and $R_{10}$ is an alkyl group.

The term "acylamino" is art-recognized and refers to a moiety that may be represented by the general formula:

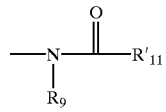

wherein $R_9$ is as defined above, and $R'_{11}$ represents a hydrogen, an alkyl, an alkenyl or —$(CH_2)_m$—R80, where m and R80 are as defined above.

The term "amido" is art recognized as an amino-substituted carbonyl and includes a moiety that may be represented by the general formula:

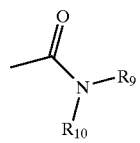

wherein $R_9$, $R_{10}$ are as defined above. Certain embodiments of the amide will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R80, wherein m and R80 are defined above. Representative alkylthio groups include methylthio, ethyl thio, and the like.

The term "carbonyl" is art recognized and includes such moieties as may be represented by the general formula:

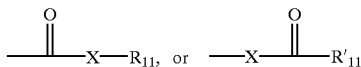

wherein X is a bond or represents an oxygen or a sulfur, and $R_{11}$ represents a hydrogen, an alkyl, an alkenyl, —$(CH_2)_m$—R80 or a pharmaceutically acceptable salt, $R'_{11}$ represents a hydrogen, an alkyl, an alkenyl or —$(CH_2)_m$—R80, where m and R80 are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11}'$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—$(CH_2)_m$—R80, where m and R80 are described above.

The term "sulfonate" is art recognized and includes a moiety that may be represented by the general formula:

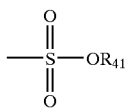

in which $R_{41}$ is an electron pair, hydrogen, alkyl, cycloalkyl, or aryl.

The term "sulfate" is art recognized and includes a moiety that may be represented by the general formula:

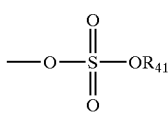

in which $R_{41}$ is as defined above.

The term "sulfonamido" is art recognized and includes a moiety that may be represented by the general formula:

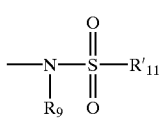

in which $R_9$ and $R'_{11}$ are as defined above.

The term "sulfamoyl" is art-recognized and includes a moiety that may be represented by the general formula:

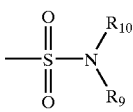

in which $R_9$ and $R_{10}$ are as defined above.

The term "sulfonyl", as used herein, refers to a moiety that may be represented by the general formula:

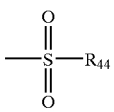

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that may be represented by the general formula:

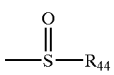

in which $R_{44}$ is selected from the group consisting of hydrogen, alkyl, alkenyl, alkynyl, cycloalkyl, heterocyclyl, aralkyl, or aryl.

A "phosphoryl" may in general be represented by the formula:

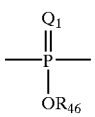

wherein $Q_1$ represented S or O, and $R_{46}$ represents hydrogen, a lower alkyl or an aryl. When used to substitute, e.g., an alkyl, the phosphoryl group of the phosphorylalkyl may be represented by the general formula:

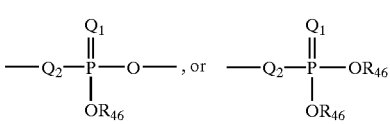

wherein $Q_1$ represented S or O, and each $R_{46}$ independently represents hydrogen, a lower alkyl or an aryl, $Q_2$ represents O, S or N. When $Q_1$ is an S, the phosphoryl moiety is a "phosphorothioate".

A "phosphoramidite" may be represented in the general formula:

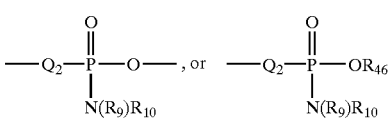

wherein $R_9$ and $R_{10}$ are as defined above, and $Q_2$ represents O, S or N.

A "phosphonamidite" may be represented in the general formula:

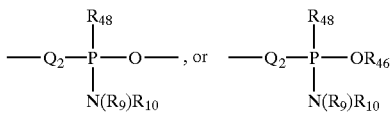

wherein $R_9$ and $R_{10}$ are as defined above, $Q_2$ represents O, S or N, and $R_{48}$ represents a lower alkyl or an aryl, $Q_2$ represents O, S or N.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—$R_7$, m and $R_7$ being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*.

Certain monomeric subunits of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds that may be substituted or unsubstituted.

The phrase "protecting group" as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

The phrase "hydroxyl-protecting group" as used herein refers to those groups intended to protect a hydrozyl group against undesirable reactions during synthetic procedures and includes, for example, benzyl or other suitable esters or ethers groups known in the art.

As used herein, the definition of each expression, e.g. lower alkyl, m, n, p, etc., when it occurs more than once in any structure, is intended to be independent of its definition elsewhere in the same structure.

The term "electron-withdrawing group" is recognized in the art, and denotes the tendency of a substituent to attract valence electrons from neighboring atoms, i.e., the substituent is electronegative with respect to neighboring atoms. A quantification of the level of electron-withdrawing capability is given by the Hammett sigma (a) constant. This well known constant is described in many references, for instance, J. March, *Advanced Organic Chemistry*, McGraw Hill Book Company, New York, (1977 edition) pp. 251–259. The Hammett constant values are generally negative for electron donating groups ($\sigma(P)$=–0.66 for $NH_2$) and positive for electron withdrawing groups ($\sigma(P)$=0.78 for a nitro group), $\sigma(P)$ indicating para substitution. Exemplary electron-withdrawing groups include nitro, acyl, formyl, sulfonyl, trifluoromethyl, cyano, chloride, and the like. Exemplary electron-donating groups include amino, methoxy, and the like.

The term "$ED_{50}$" means the dose of a drug which produces 50% of its maximum response or effect. Alternatively, the dose which produces a pre-determined response in 50% of test subjects or preparations.

The term "$LD_{50}$" means the dose of a drug which is lethal in 50% of test subjects.

The term "therapeutic index" refers to the therapeutic index of a drug defined as $LD_{50}/ED_{50}$.

A "gene therapy construct" as used herein refers to an expression vector which may alter the phenotype of a cell, particularly a muscle cell, when taken up by the cell. For example, the gene therapy construct may be an "recombinant coding sequence" which encodes a polypeptide, or is transcribable to an antisense nucleic acid, a ribozyme, or any other RNA product which alters the phenotype of the cell in which it is produced. As used herein, "recombinant gene" refers to a genetic construct including a "recombinant coding sequence."

The term "genetic immunization" generally includes the direct delivery of DNA or RNA sequences to tissues in vivo in order provoke the in situ synthesis of proteins which, if seen by the host as foreign, may induce an immune response.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression construct which is in turn used to transform a host cell, e.g., a host muscle cell, to produce the heterologous protein. That is, the polypeptide is expressed from a heterologous nucleic acid.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or anti sense) and double-stranded polynucleotides.

An "inducible" promoter is a promoter which is under environmental or developmental regulation.

The term "constitutive" promoter refers to a promoter which is active under most environmental and developmental conditions.

The term "operably linked" refers to functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "vector" refers to a nucleic acid molecule capable of transporting another nucleic acid to which it has been linked, and includes plasmids, cosmids or phages.

As used herein, "antisense" nucleic acid refers to oligonucleotides which specifically hybridize (e.g. bind) under cellular conditions with a gene sequence, such as at the cellular mRNA and/or genomic DNA level, so as to inhibit expression of that gene, e.g. by inhibiting transcription and/or translation. The binding may be by conventional base pair complementarily, or, for example, in the case of binding to DNA duplexes, through specific interactions in the major groove of the double helix.

A "ribozyme sequence" is a catalytic RNA sequence capable of cleaving a target RNA, such as a hairpin or hammerhead ribozyme. The term also encompasses a nucleic acid sequence in an expression cassette from which the RNA is transcribed.

The term "host cell" or "target cell" refers to a cell transduced with a specified vector. The cell is optionally selected from in vitro cells such as those derived from cell culture, ex vivo cells, such as those derived from an organism, and in vivo cells, such as those in an organism.

A "patient" or "subject" to be treated by the subject method may mean either a human or non-human animal.

Contemplated equivalents of the polymers, subunits and other compositions described above include such materials which otherwise correspond thereto, and which have the same general properties thereof (e.g., biocompatible), wherein one or more simple variations of substituents are made which do not adversely affect the efficacy of such molecule to achieve its intended purpose. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

3. Exemplary Compositions and Methods

In certain embodiments, a polymer of the subject invention may include one or more subunits of general formula (XV):

Formula XV

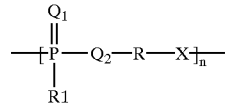

wherein, independently for each occurrence:
$Q_1$ represents O or S;
$Q_2$ represents O, S or NR';
X represents O, S or NR';
R' represents H or alkyl;
R represents an organic or organometallic moiety, e.g., a substituted or unsubsituted cyclic, branched or straight chain aliphatic group of 2 to about 10 bonds in length, including alkyls, alkenyls, cycloalkyls, cycloalkenyls, alkynyls, aryls, heteroalkyls, or heteroaryl moieties;
R1 represents hydrogen, alkyl, —O-alkyl, —O-cycloalkyl, aryl, —O-aryl, heterocycle, —O-heterocycle, —S—$R_4$, —O—(C=O)—$R_4$, —Cl or —N($R_2$)$R_3$;
$R_2$ and $R_3$, each independently, represent a hydrogen, an alkyl, an alkenyl, —(CH$_2$)$_n$—$R_4$, or $R_2$ and $R_3$ taken together with the N atom to which they are attached complete a heterocycle having from 4 to about 8 atoms in the ring structure; and
$R_4$ represents a hydrogen, aryl, cycloalkyl, cycloalkenyl, heterocycle or polycycle.

In certain embodiments, "n" in formula XV range from about 5 to about 500 or more. Alternatively, in other embodiments, "n" may be about 10, 25, 50, 75, 100, 150, 200, 300, or 400.

In certain embodiments, the polymers of the present invention are comprised almost entirely, if not entirely, of the same subunit. Alternatively, in other embodiments, the polymers may be copolymers, in which different subunits and/or other monomeric units are incorporated into the polymer. In certain instances, the polymers are random copolymers, in which the different subunits and/or other monomeric units are distributed randomly throughout the polymer chain. For example, the polymer having units of formula XV may consist of effectively only one type of such subunit, or alternatively two or more types of such subunits. In addition, the polymer may contain monomeric units other than those subunits represented by formula XV. In other embodiments, the different types of monomeric units, be they one or more subunits depicted by formula XV or other monomeric units, are distributed randomly throughout the chain. In part, the term "random" is intended to refer to the situation in which the particular distribution or incorporation of monomeric units in a polymer that has more than one type of monomeric units is not directed or controlled directly by the synthetic protocol, but instead results from features inherent to the polymer system, such as the reactivity, amounts of subunits and other characteristics of the synthetic reaction or other methods of manufacture, processing or treatment.

The ratio of different subunits in any polymer of the present invention may vary. For example, in certain embodiments, polymers of the present invention may be composed almost entirely, if not entirely, of a single monomeric element, such as a subunit depicted in formula XV. Alternatively, in other instances, the polymers of the present invention are effectively composed of two different subunits, in which the percentage of each subunit may vary from less than 1:99 to more than 99:1, or alternatively 10:90, 15:85, 25:75, 40:60, 50:50, 60:40, 75:25, 85:15, 90:10 or the like. For example, in some instances, a polymer of the present invention may be composed of two different subunits that may be both represented by the generic formula XV, but which differ in their chemical identity. In certain embodiments, the polymers of the present invention may have just a few percent, or even less (e.g., 5, 2.5, 1, 0.5, 0.1%) of the subunits having phosphorous-based linkages, which give rise, in part, the biodegradability characteristics of the resulting polymer system. In other embodiments, in which three or more different monomeric units are present, the present invention contemplates a range of mixtures like those taught for the two-component systems.

In certain embodiments, the polymeric composition of the present invention include one or more recurring monomeric elements in the polymer represented in general formula (I) and (II):

it does not interfere with the polymerization or biodegradation reactions of the polymer. Specifically, L may be an alkylene group, such as methylene, ethylene, 1,2-dimehtylethylene, n-propylene, isopropylene, 2,2-dimethylpropylene or tert-butylene, n-pentylene, tert-pentylene, n-hexylene, n-heptylene and the like; an alkylene substituted with a non-interfering substituent, for example, hydroxy-, halogen-, or nitrogen-substituted alkylene; an alkylene group such as ethenylene, propenylene, 2-(3-propenyl)-dodecylene; and an alkynylene group such as ethynylene, proynylene, 1-(4-butynyl)-3-methyldecylene; and the like.

In certain embodiments, L is independently a branched or straight chain alkylene group, alternatively, an alkylyene group having from 1 to about 7 carbon atoms. In other embodiments, L is an ethylene group, a methyl-substituted methylene group, or an ethylene group.

$M_1$ and $M_2$ in the formula are each independently either (i) a branched or straight chain aliphatic group having from 1 to about 20 carbon atoms, or (ii) a branched or straight chain, oxy-carboxy-, or amino-aliphatic group having from 1 to about 20 carbon atoms. In either case the branched or straight chain aliphatic group may be any divalent aliphatic moiety having from 1 to about 20 carbon atoms, preferably 1 to about 7 carbon atoms, that does not interfere with the polymerization, copolymerization, or biodegradation reactions of the polymers. Specifically, when either $M_1$ or $M_2$ is a branched or straight chain aliphatic group having from 1 to about 20 carbon atoms, it may be, for example, an alkylene group such as methylene, ethylene, 1-methylethylene, 1,2-dimethylethylene, n-propylene, trimethylene, isopropylene, 2,2-dimethylpropylene or tert-butylene, n-pentylene, tert-pentylene, n-hexylene, n-heptylene, n-octylene, n-nonylene, n-decylene, n-undecylene, n-dodecylene, and the like; an alkenylene group such as n-propenylene, 2-vinylpropylene, n-butenylene, 3-theylbutylene, n-pentenylene, 4-(3-propenyl)hexylene, n-octenylene, 1-(4-butenyl)-3-methyldecylene, 2-(3-propenyl)dodecylene, hexadece-

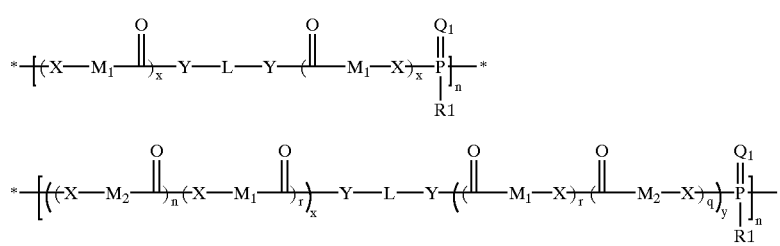

Formula I

Formula II wherein, independently for each occurrence:
$Q_1$ represents O or S;
X represents O, S or NR';
R' is H or alkyl;
R1 represents hydrogen, alkyl, —O-alkyl, aryl, —O-aryl, heterocycle, —O-heterocycle, or —N(R$_2$)R$_3$;
$R_2$ and $R_3$, each independently, represent a hydrogen, an alkyl, an alkenyl, —(CH$_2$)$_p$—R$_4$, or R$_2$ and R$_3$, taken together with the N atom to which they are attached, complete a heterocycle having from 4 to about 8 atoms in the ring structure; and,
$R_4$ represents an aryl, a cycloalkyl, a cycloalkenyl, a heterocycle or a polycycle.

L may be any divalent branched or straight chain aliphatic group having from 1 to about 20 carbon atoms, so long as nylene and the like; an alkynylene group, such as ethynylene, propynylene, 3-(2-ethynyl)pentylene, n-hexynylene, 2-(2-propynyl)decylene, and the like; or an alkylene, alkenylene or alkynylene group substituted with a non-interfering substituent, for example, a hydroxy, halogen or nitrogen group, such as 2-chloro-n-decylene, 1-hydroxy-3-ethenylbutylene, 2-propyl-6-nitro-10-dodecynylene, and the like.

When either $M_1$ or $M_2$ is a branched or straight chain, oxyaliphatic group having from 1 to about 20 carbon atoms, it may be, for example, a divalent alkoxylene group, such as ethoxylene, 2-methylethoxylene, propoxylene, butoxylene, pentoxylene, dodecyloxylene, hexadecyloxylene, and the like. When $M_1$ or $M_2$ is a branched or straight chain, oxy-aliphatic group, it may have the formula —O—(CH$_2$)$_a$— where a is 1 to about 7.

When either $M_1$ or $M_2$ is a branched or straight chain, oxyaliphatic group having from 1 to about 20 carbon atoms, it may also be, for example, a dioxyalkylene group such as dioxymethylene, dioxyethylene, 1,3-dioxypropylene, 2-methoxy-1,3-dioxypropylene, 1,3-dioxy-2-methylpropylene, dioxy-n-pentylene, dioxy-n-octadecylene, methoxylene-methoxylene, ethoxylene-methoxylene, ethoxylene-ethoxylene, ethoxylene-1-propoxylene, butoxylene-n-propoxylene, pentadecyloxylene-methoxylene, and the like. When $M_1$ or $M_2$ is a branched or straight chain, dioxo-aliphatic group, it may have the formula —O—(CH$_2$)$_a$—O— or —O—(CH$_2$)$_a$—O—(CH$_2$)$_b$—, wherein each of a and b is from 1 to about 7.

When either $M_1$ or $M_2$ is a branched or straight chain, carboxy-aliphatic group having from 1 to about 20 carbon atoms, it may also be, for example, a divalent carboxylic acid ester such as the divalent radical of methyl formate, methyl acetate, ethyl acetate, n-propyl acetate, isopropyl acetate, n-butyl acetate, ethyl propionate, allyl propionate, t-butyl acrylate, n-butyl butyrate, vinyl chloroacetate, 2-methoxycarbonylcyclohexanone, 2-acetoxycyclohexanone, and the like. When $M_1$ or $M_2$ is a branched or straight chain, carboxy-aliphatic group, it may have the formula —O—CHR$_5$—CO—O—CHR$_6$—, wherein $R_5$ and $R_6$ are each independently H, alkyl, alkoxy, aryl, aryloxy, heterocyclic or heterocycloxy.

When either $M_1$ or $M_2$ is a branched or straight chain, amino-aliphatic group having from 1 to about 20 carbon atoms, it may be a divalent amino such as —CH$_2$NH—, —(CH$_2$)$_2$N—, —CH$_2$(C$_2$H$_5$)N—, —n—C$_4$H$_9$NH—, —t—C$_4$H$_9$NH—, —CH$_2$(C$_3$H$_7$)N—, —C$_2$H$_5$(C$_3$H$_7$)N—, —CH$_2$(C$_8$H$_{17}$)N—, and the like. When $M_1$ or $M_2$ is a branched or straight chain, amino-aliphatic group, it may have the formula —(CH$_2$)$_a$—NR'— where R' is H or lower alkyl.

In certain embodiments, $M_1$ and/or $M_2$ is an alkylene group having the formula —O—(CH2)$_a$— where a is 1 to about 7, or alternatively, a divalent ethylene group. In another embodiment, $M_1$ and $M_2$ are both present; $M_1$ and $M_2$ are not the same chemical entity; and $M_1$ and $M_2$ are n-pentylene and the divalent radical of methyl acetate, respectively.

R1 in the polymer of the invention is H, alkyl, alkoxy, aryl, aryloxy, heterocyclic or heterocycloxy residue. Examples of possible alkyl R1 groups include methyl, ethyl, n-propyl, i-propyl, n-butyl, tert-butyl, —C$_8$H$_{17}$, and the like groups; alkyl substituted with a non-interfering substituent, such as hydroxy, halogen, alkoxy or nitro; corresponding alkoxy groups; and alkyl conjugated to a biologically active substance to from a pendant drug delivery system.

When R1 is aryl or the corresponding aryloxy group, it typically contains from about 5 to about 14 carbon atoms, or about 5 to about 12 carbon atoms, and optionally, may contain one or more rings that are fused to each other. Examples of particularly suitable aromatic groups include phenyl, phenoxy, naphthyl, anthracenyl, phenanthrenyl and the like.

When R1 is heterocyclic or heterocycloxy, it typically contains from about 5 to about 14 ring atoms, alternatively from about 5 to about 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando [3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthyridine, pyrido [3,4-b]-pyridine, pyrido [3,2-b]-pyridine, pyrido [4,3-b] pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. In certain embodiments, when R1 is heterocyclic or heterocycloxy, it is selected from the group consisting of furan, pyridine, N-alkylpyridine, 1,2,3- and 1,2,4-triazoles, indene, anthracene and purine rings.

In certain embodiments, R1 is an alkyl group, an alkoxy group, a phenyl group, a phenoxy group, a heterocycloxy group, or an ethoxy group.

The molar ratio of n: (x or y) may vary greatly depending on the biodegradability and the release characteristics desired in embodiments of the present invention, but typically varies between about 200:1 and 1:200. In certain embodiments, the ratio x:y is from about 100:1 to about 1:100 and, alternatively, from about 50:1 to about 1:50.

The molar ratio of q:r may vary greatly depending on the biodegradability and the release characteristics desired in embodiments of the present invention, but typically varies between about 1:200 and 200:1. In certain embodiments, the ratio q:r is from about 1:150 to about 150:1 and, alternatively, from about 1:99 to about 99:1.

The molar ratio of x:y may also vary greatly depending on the biodegradability and the release characteristics desired in embodiments of the present invention. Typically, such ratio is about 1.

In another embodiment, the subject polymeric transfection system comprises a polymer including one or more recurring monomeric elements in the polymer represented in general formula VIII:

Formula VIII

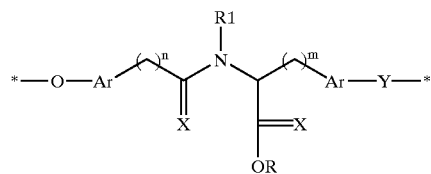

wherein, independently for each occurrence:
  Ar, independently for each occurrence, represents an aryl moiety;
  X, independently for each occurrence, represents O or S;
  Y represents a phosphate, or derivative or analog thereof;
  R represents H, an alkyl, an alkenyl, an alkynyl, an aryl, a heterocycle or a branched or straight chain aliphatic group having from 1 to about 20 carbon atoms;
  R1 represents H or a lower alkyl; and
  n and m, independently, are 0, 1, 2 or 3.

In certain embodiments of the present invention, X is O, and in other embodiments, n and m, independently, are 1 or 2.

Certain embodiments of the present invention that are encompassed by Formula VIII include a polymeric composition having one or more recurring monomeric units represented in general formula (IX):

Formula IX

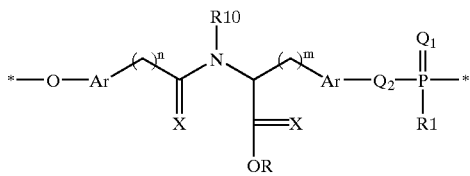

wherein, independently for each occurrence:
Ar, independently for each occurrence, represents an aryl moiety;
X, independently for each occurrence, represents O or S;
Y represents a phosphate, or derivative thereof;
$Q_1$ represents O or S;
$Q_2$ represents O, S or NH;
in R represents H, an alkyl, an alkenyl, an alkynyl, an aryl, a heterocycle or a branched or straight chain aliphatic group having from 1 to about 20 carbon atoms;
R1 represents hydrogen, alkyl, —O-alkyl, —O-cycloalkyl, aryl, —O-aryl, heterocycle, —O-heterocycle, or —N($R_2$)$R_3$;
$R_2$ and $R_3$, each independently, represent a hydrogen, an alkyl, an alkenyl, —($CH_2$)$_n$—$R_4$, or $R_2$ and $R_3$ taken together with the N atom to which they are attached complete a heterocycle having from 4 to about 8 atoms in the ring structure;
$R_4$ represents an aryl, a cycloalkyl, a cycloalkenyl, a heterocycle or a polycycle;
$R_{10}$ represents H or a lower alkyl; and
i, n and m, independently for each occurrence, are 0, 1, 2 or 3.

In certain embodiments, compositions of the present invention include polymeric chains represented in general formula (IXa):

Formula IXa

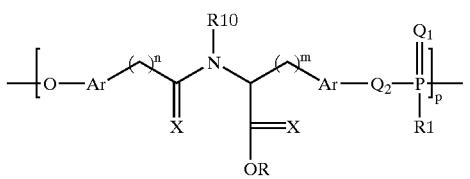

wherein the nomenclature is the same as for general formula IX, and p is in the range of about 100 to about 10,000 or more. Usually, the value for p in any sample of polymer, such as that depicted in Formula IXa, varies from polymeric chain to polymeric chain.

In certain embodiments, the biodegradable polymer of the invention comprises the recurring monomeric units shown in formula X:

Formula XV

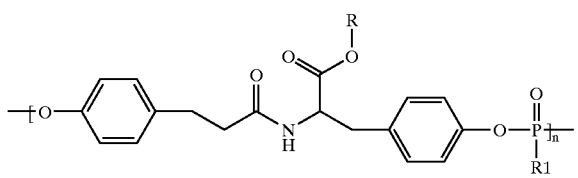

wherein, independently for each occurrence: R is H, alkyl, aryl or heterocyclic. R may be any aliphatic moiety so long as it does not interfere undesirably with the polymerization or biodegradation reactions of the polymer. In certain embodiments, R is a branched or straight chain aliphatic group having from 1 to about 20 carbon atoms. Specifically, R may be an alkyl group, such as methyl, ethyl, 1,2-dimethylethyl, n-propyl, isopropyl, 2,2-dimethylpropyl or tert-butyl, n-pentyl, tert-pentyl, n-hexyl, n-heptyl and the like; an alkyl group substituent, for example, halogen-substituted alkyl; or a cycloaliphatic group such as cyclopentyl, 2-methylcyclopentyl, cyclohexyl, cyclohexenyl and the like. In some embodiments, R is a branched or straight chain alkyl group, an alkyl group having from 2 to about 18 carbon atoms, or an n-hexyl group.

$R_1$ in the polymer of the invention, independently for each occurrence, is an alkyl, alkoxy, aryl, aryloxy, heterocyclic or heterocycl-loxy residue. Examples of useful alkyl $R_1$ groups include methyl, ethyl, n-propyl, i-propyl, n-butyl, tert-butyl, —$C_8H_{17}$, and the like groups; alkyl substituted with a non-interfering substituent, such as a halogen group; corresponding alkoxy groups, and alkyl that is conjugated with a biologically active substance to form a pendant drug delivery system.

When $R_1$ is aryl or the corresponding aryloxy group, it typically contains from about 5 to about 14 carbon atoms, alternatively about 5 to about 12 carbon atoms, and optionally may contain one or more rings that are fused to each other. Examples of particularly suitable aromatic groups include phenyl, phenoxy, naphthyl, anthracenyl, phenanthrenyl and the like.

When $R_1$ is heterocyclic or heterocycloxy, it typically contains from about 5 to about 14 ring atoms, alternatively from about 5 to about 12 ring atoms, and one or more heteroatoms. Examples of suitable heterocyclic groups include furan, thiophene, pyrrole, isopyrrole, 3-isopyrrole, pyrazole, 2-isoimidazole, 1,2,3-triazole, 1,2,4-triazole, oxazole, thiazole, isothiazole, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-dioxazole, 1,2,4-dioxazole, 1,3,2-dioxazole, 1,3,4-dioxazole, 1,2,5-oxatriazole, 1,3-oxathiole, 1,2-pyran, 1,4-pyran, 1,2-pyrone, 1,4-pyrone, 1,2-dioxin, 1,3-dioxin, pyridine, N-alkyl pyridinium, pyridazine, pyrimidine, pyrazine, 1,3,5-triazine, 1,2,4-triazine, 1,2,3-triazine, 1,2,4-oxazine, 1,3,2-oxazine, 1,3,5-oxazine, 1,4-oxazine, o-isoxazine, p-isoxazine, 1,2,5-oxathiazine, 1,2,6-oxathiazine, 1,4,2-oxadiazine, 1,3,5,2-oxadiazine, azepine, oxepin, thiepin, 1,2,4-diazepine, indene, isoindene, benzofuran, isobenzofuran, thionaphthene, isothionaphthene, indole, indolenine, 2-isobenzazole, 1,4-pyrindine, pyrando[3,4-b]-pyrrole, isoindazole, indoxazine, benzoxazole, anthranil, 1,2-benzopyran, 1,2-benzopyrone, 1,4-benzopyrone, 2,1-benzopyrone, 2,3-benzopyrone, quinoline, isoquinoline, 12,-benzodiazine, 1,3-benzodiazine, naphthpyridine, pyrido[3,4-b]-pyridine, pyrido[3,2-b]-pyridine, pyrido[4,3-b]-pyridine, 1,3,2-benzoxazine, 1,4,2-benzoxazine, 2,3,1-benzoxazine, 3,1,4-benzoxazine, 1,2-benzisoxazine, 1,4-benzisoxazine, carbazole, xanthrene, acridine, purine, and the like. In certain embodiments, when $R_1$ is heterocyclic or heterocycloxy, it is selected from the group consisting of furan, pyridine, N-alkylpyridine, 1,2,3- and 1,2,4-triazoles, indene, anthracene and purine rings.

In certain embodiments, $R_1$ is an alkyl group, an alkoxy group, a phenyl group, a phenoxy group, or a heterocycloxy group, an alkoxy group having from 1 to about 7 carbon atoms, or an ethoxy group.

The number n may vary greatly depending on the biodegradability and the release characteristics desired in the polymer, but typically varies between about 2 and about 500 or even greater. In certain embodiments, n is from about 5 to about 300, or about 200.

In another embodiment, the polymeric formulation of the subject transfection system may be made with poly (cycloaliphatic phosphoester)s, e.g., comprising a polymer having the recurring monomeric units shown in formula XI:

$$*\!-\!\!\left[\!X\!-\!R\!-\!L\!-\!R''\!-\!Q_2\!-\!\overset{\overset{Q_1}{\|}}{\underset{R1}{P}}\!\right]_n\!\!-\!*$$

Formula XI wherein, independently for each occurrence:

$Q_1$ represents O or S;

$Q_2$ represents O, S or NR';

X represents O, S or NR';

R' is H or alkyl;

R1 represents hydrogen, alkyl, —O-alkyl, —O-cycloalkyl, aryl, —O-aryl, heterocycle, —O-heterocycle, or —N($R_2$)$R_3$;

$R_2$ and $R_3$, each independently, represent a hydrogen, an alkyl, an alkenyl, —($CH_2$)$_n$—$R_4$, or $R_2$ and $R_3$ taken together with the N atom to which they are attached complete a heterocycle having from 4 to about 8 atoms in the ring structure;

$R_4$ represents an aryl, a cycloalkyl, a cycloalkenyl, a heterocycle or a polycycle;

R and R'', each independently, represent a straight or branched aliphatic, either unsubstituted or substituted with one or more non-interfering substituents;

L is a divalent cycloaliphatic group; and n is 5 to 1,000 wherein the polymer composition is biocompatible both before and upon biodegradation.

In still another embodiment, the polymeric transfection system may include a biodegradable terephthalate polymers of the invention comprise the recurring monomeric units shown in formula XII:

Other biodegradable poly(phosphoesters) which may be adapted for use in the subject invention are described in the art, such as U.S. Pat. Nos. 5,256,765 and 5,194,581.

The subject transfection system may also be formulated with other polymers including, for example, certain polyanhydrides, poloxamers, pseudopolyamino acids, poly (ester-amides) and like. For example, hydrolyzable group may be polymers and oligomers of glycolide, lactide, ε-caprolactone, other hydroxy acids, and other biologically degradable polymers that yield materials that are non-toxic or present as normal metabolites in the body. Other useful materials include poly(amino acids), poly(anhydrides), poly (orthoesters), poly(phosphazines) and poly(phosphoesters). Polylactones such as poly(ε-caprolactone), poly(ε-caprolactone), poly(Δ-valerolactone) and poly(γ-butyrolactone), for example, may also be useful.

The polymer of the invention may also comprise additional biocompatible monomeric units as long as they do not interfere with the biodegradable characteristics desired. Such additional monomeric units may offer even greater flexibility in designing the precise release profile desired for targeted drug delivery or the precise rate of biodegradability desired for structural implants such as for orthopedic applications. Examples of such additional biocompatible monomers include the recurring units found in polycarbonates; polyorthoesters; polyamides; polyurethanes; poly (iminocarbonates); and polyanhydrides.

To determine whether any polymer of the subject invention is biocompatible, it may be necessary to conduct a toxicity analysis. Such assays are well known in the art. On example of such an assay would be performed with live carcinoma cells, such as GT3TKB tumor cells, in the following manner:

About 100–150 mg of the sample polymer is degraded in 20 mL of 1M NaOH at 37° C. for 1–2 days, or until complete degradation is observed. The solution is then neutralized with 20 mL of 1M HCl. About 200 μL of various concentrations of the degraded polymer products are placed in 96-well tissue culture plates and seeded with human gastric carcinoma cells (GT3TKB) at $10^4$/well density. The degraded polymer products are incubated with the GT3TKB cells for 48 hours. The results of the assay may be plotted as % relative growth vs. Concentration of degraded polymer in the tissue-culture well.

Formula XII $$*\!-\!\!\left[\!(O\!-\!R\!-\!O\!-\!\overset{O}{\underset{}{\overset{\|}{C}}}\!-\!\!\bigcirc\!\!-\!\overset{O}{\underset{}{\overset{\|}{C}}}\!-\!O\!-\!R\!-\!O\!-\!\overset{\overset{Q_1}{\|}}{\underset{R1}{P}}\!\right)_{\!x}\!\!\left(O\!-\!R\!-\!O\!-\!\overset{O}{\underset{}{\overset{\|}{C}}}\!-\!\!\bigcirc\!\!-\!\overset{O}{\underset{}{\overset{\|}{C}}}\!\right)_{\!y}\right]_n\!\!-\!*$$

wherein, independently for each occurrence:

$Q_1$ represents O or S;

R is a divalent organic moiety;

R1 represents hydrogen, alkyl, —O-alkyl, —O-cycloalkyl, aryl, —O-aryl, heterocycle, —O-heterocycle, or —N($R_2$)$R_3$;

$R_2$ and $R_3$, each independently, represent a hydrogen, an alkyl, an alkenyl, —($CH_2$)$_n$—$R_4$, or $R_2$ and $R_3$ taken together with the N atom to which they are attached complete a heterocycle having from 4 to about 8 atoms in the ring structure;

$R_4$ represents an aryl, a cycloalkyl, a cycloalkenyl, a heterocycle or a polycycle; and, x is >1, y is 1 to about 5; and n is 1 to about 5,000 or more, wherein the biodegradable polymer is sufficiently pure to be biocompatible and degrades to biocompatible residues upon biodegradation.

In addition, polymers and formulations of the present invention may also be evaluated by well-known in vivo tests, such as subcutaneous implantations in rats to confirm that they hydrolyze without significant levels of irritation or inflammation at the subcutaneous implantation sites.

In certain embodiments, the polymer of the present invention is soluble in one or more common organic solvents for ease of fabrication and processing. Common organic solvents include such solvents as chloroform, dichloromethane, acetone, ethyl acetate, DMAC, N-methyl pyrrolidone, dimethylformamide, and dimethylsulfoxide.

4. Exemplary Synthesis

The most common general reaction in preparing poly (phosphates) is a dehydrochlorination between a phosphorodichloridate and a diol according to the following equation:

$$n \quad Cl-\underset{OR'}{\underset{|}{\overset{O}{\overset{\|}{P}}}}-Cl \quad + \quad n \quad HO-R-OH \longrightarrow$$

$$-\left[\underset{OR'}{\underset{|}{\overset{O}{\overset{\|}{P}}}}-O-R-O\right]_n + 2n \text{ HCl}$$

Most poly(phosphonates) are also obtained by condensation between appropriately substituted dichlorides and diols.

Poly(phosphites) have been prepared from glycols in a two-step condensation reaction. A 20% molar excess of a dimethylphosphite is used to react with the glycol, followed by the removal of the methoxyphosphonyl end groups in the oligomers by high temperature.

One feature of melt polycondensation is that it avoids the use of solvents and large amounts of other additives, thus making purification more straightforward. It may also provide polymers of reasonably high molecular weight. Somewhat rigorous conditions, however, are often required and may lead to chain acidolysis (or hydrolysis if water is present). Unwanted, thermally-induced side reactions, such as cross-linking reactions, may also occur if the polymer backbone is susceptible to hydrogen atom abstraction or oxidation with subsequent macroradical recombination.

To minimize these side reactions, the polymerization may also be carried out in solution. Solution polycondensation requires that both the prepolymer and the phosphorus component be soluble in a common solvent. Typically, a chlorinated organic solvent is used, such as chloroform, dichloromethane or dichloroethane. The solution polymerization is usually run in the presence of equimolar amounts of the reactants and a stoichiometric amount of an acid acceptor, usually a tertiary amine such as pyridine or triethylamine. The product is then typically isolated from the solution by precipitation in a non-solvent and purified to remove the hydrochloride salt by conventional techniques known to those or ordinary skill in the art, such as by washing with an aqueous acidic solution, e.g., dilute HCl.

Reaction times tend to be longer with solution polymerization than with melt polymerization. However, because overall milder reaction conditions may be used, side reactions are minimized, and more sensitive functional groups may be incorporated into the polymer. One different of solution polymerization from other polymerization methods is that the attainment of high molecular weights, such as a Mw greater than 20,000, is less common.

Interfacial polycondensation may be used when high molecular weight polymers are desired at high reaction rates. Mild conditions minimize side reactions. Also the dependence of high molecular weight on stoichiometric equivalence between diol and dichloridate inherent in solution methods is removed. However, hydrolysis of the acid chloride may occur in the alkaline aqueous phase. Sensitive dichloridates that have some solubility in water are generally subject to hydrolysis rather than polymerization. Phase transfer catalysts, such as crown ethers or tertiary ammonium chloride, may be used to bring the ionized diol to the interface to facilitate the polycondensation reaction. The yield and molecular weight of the resulting polymer after interfacial polycondensation are affected by reaction time, molar ratio of the monomers, volume ratio of the immiscible solvents, the type of acid acceptor, and the type and concentration of the phase transfer catalyst.

In certain embodiments of the present invention, the biodegradable polymer of formula I or II is made by a process comprising the steps of:

(a) reacting at least one heterocyclic ring compound having formula III, IV or V:

Formula III

Formula IV

Formula V wherein $M_1$, $M_2$ and X are as defined above,
with an initiator having the formula H—Y—L—Y—H, wherein Y and L are as defined above, to form a prepolymer of formula VI or VII, shown below:

Formula VI $$-(X-M_1-\overset{O}{\overset{\|}{C}})_x-Y-L-Y-(\overset{O}{\overset{\|}{C}}-M_1-X)_x-$$

Formula VII $$-\left[(X-M_2-\overset{O}{\overset{\|}{C}})_n-(X-M_1-\overset{O}{\overset{\|}{C}})_r\right]_x-Y-L-Y-\left[(\overset{O}{\overset{\|}{C}}-M_1-X)_r-(\overset{O}{\overset{\|}{C}}-M_2-X)_q\right]_y-$$

wherein X, $M_1$, $M_2$, Y, L, R, x, y, q and r are as defined above; and (b) farther reacting said prepolymer of formula VI and VII with a phosphorodihalidate of formula VIII:

Formula VIII $$halo-\underset{R_1}{\underset{|}{\overset{O}{\overset{\|}{P}}}}-halo$$

where "halo" is Br, Cl or I; and $R_1$ is as defined above, to form said polymer of formula I or II.

The function of the first reaction step (a) is to use the initiator to open the ring of the heterocyclic ring compound of formula III, IV or V. Examples of useful heterocyclic compounds of formula II, IV or V include caprolactones, caprolactams, amino acid anhydrides such as glycine anhydride, cycloalkylene carbonates, dioxanones, glycolids, lactides and the like.

When the compound of the invention has formula I, only one heterocyclic rong compound of formula II, which contains $M_1$, may be used to prepare the prepolymer of formula VI in step (a). When the compound of the invention has formula II, then a combination of a heterocyclic compound of formula III, which contains $M_1$, and a heterocyclic compound of formula IV which contains $M_2$, may be used in step (a). Alternatively, when the compound of the invention has formula II, a single heterocyclic compound of formula V, which contains both $M_1$ and $M_2$, may be used in step (a).

Examples of suitable initiators include a wide variety of compounds having at least two active hydrogens (H—Y—L—Y—H) where L is a linking group and is defined above, and Y may be —O—, —S— or —NR", where R" is as defined above. The linking group L may be a straight chain group, e.g., alkylene, but it may also be substituted with one or more additional active-hydrogen-containing groups. For example, L may be a straight chain alkylene group substituted with one or more additional alkyl groups, each bearing an activated hydrogen moiety, such as —OH, —SH, or $NH_2$. In this way, various branched polymers may be prepared using the branched active hydrogen initiators to design the resulting polymer such that it has the desired properties. However, when branched polymers are reacted with acid chlorides, cross-linked polymers will result.

The reaction step (a) may take place at widely varying temperatures, depending upon the solvent used, the molecular weight desired, the susceptibility of the reactants to form side reactions, and the presence of a catalyst. In some embodiments, the reaction step (a) takes place at a temperature from about 0 to about +235° C. for melt conditions. Somewhat lower temperatures may be possible with the use of either a cationic or anionic catalyst.

The time required for the reaction step (a) also may vary widely, depending upon the type of reaction being used and the molecular weight desired. In certain embodiments, the reaction step (a) takes place during a time between about 1 hour and 7 days.

The reaction step (a) may be in bulk, in solution, by interfacial polycondensation, or any other convenient method of polymerization. In certain instances, the reaction step (a) takes place under melt conditions.

Examples of prepolymers include:

(i) OH-terminated prepolymer derived from polycaprolactone H—[—O($CH_2$)$_5$—CO—]$_x$—O—$CH_2$—$CH_2$—O—[—CO—($CH_2$)$_5$—O—]$_y$—H;

(ii) NH-terminated prepolymer derived from polycaprolactam (Nylon 6) H—[—NH—($CH_2$)$_5$—CO—]$_x$—NH—$CH_2$—$CH_2$—NH—[—CO—($CH_2$)$_5$—NH—]$_y$—H;

(iii) OH-terminated prepolymer derived from polylactide H—[—OCH—($CH_3$)—CO—]$_x$—O—$CH_2$—$CH_2$—O—[—CO—CH($CH_3$)—O—]$_y$—H; and, (iv) OH-terminated prepolymer derived from polytrimemethylene carbonate H—[—O—($CH_2$)$_3$—O—CO—]$_x$—O—$CH_2$—$CH_2$—O—[—CO—O—($CH_2$)$_3$—O—]$_y$—H.

Examples of other prepolymers include:

(i) OH-terminated copolymer derived from lactide and glycolide:

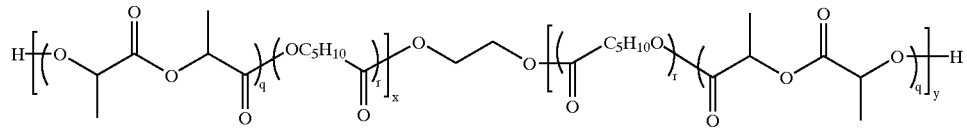

(ii) OH-terminated copolymer derived from lactide and caprolactone:

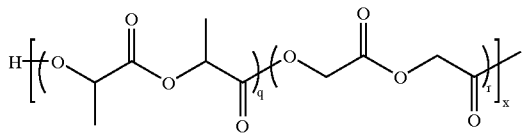

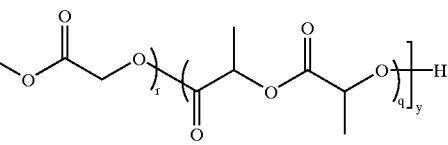

(iii) OH-terminated copolymer derived from glycolide and caprolactone:

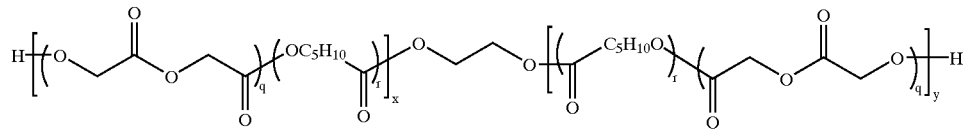

The purpose of the polymerization of step (b) is to form a polymer comprising (i) the prepolymer produced as a result of step (a) and (ii) interconnecting phosphorylated units. The result may be a block copolymer having a microcrystalline structure that is often particularly well-suited to use as a controlled release medium.

The polymerization step (b) of the invention usually takes place at a slightly lower temperature than the temperature of step (a), but also may vary widely, depending upon the type of polymerization reaction used, the presence of one or more catalysts, the molecular weight desired, and the susceptibility of the reactants to undesirable side reaction. When melt conditions are used, the temperature may vary from about 0 to about 150° C. However, when the polymerization step (b) is carried out in a solution polymerization reaction, it typically takes place at a temperature between about −40 and about 100° C. Typical solvents include methylene chloride, chloroform, or any of a wide variety of inert organic solvents.

The time required for the polymerization of step (b) may also vary widely, depending on the molecular weight of the material desired and, in general, the need to use more or less rigorous conditions for the reaction to proceed to the desired degree of completion. Typically, however, the polymerization step (b) takes place during a time of about 30 minutes to about 48 hours.

Particularly when solution polymerization reaction is used, an acid acceptor is advantageously present during the polymerization step (a). A particularly suitable class of acid acceptor comprises tertiary amines, such as pyridine, trimethylamine, triethylamine, substituted anilines and substituted aminopyridines. Another acid acceptor is the substituted aminopyridine 4-dimethylaminopryridine ("DMAP").

The polymers of formula I and II are isolated from the reaction mixture by conventional technique, such as by precipitating out, extraction with an immiscible solvent, evaporation, filtration, crystallization, and the like. Typically, however, the polymers of formulas I and II are both isolated and purified by quenching a solution of said polymer with a non-solvent or a partial solvent, such as diethyl ether or petroleum ether.

5. Biodegradability and Release Characteristics

In certain embodiments, the polymers and blends of the present invention, upon contact with body fluids, undergo gradual degradation, typically through hydrolysis, with, if so formulated, concomitant release of a nucleic acid, often a gene therapy construct, for a sustained or extended period (as compared to the release from an isotonic saline solution). Such release profile may result in prolonged delivery (over, say 1 to about 2,000 hours, or alternatively about 2 to about 800 hours) of effective amounts (e.g., about 0.0001 mg/kg/hour to about 10 mg/kg/hour) of the nucleic acid or any other material associated with the polymer.

Degradation of the polymers of the present invention typically involves cleavage of a bond to the phosphorous atom incorporated into the backbone of the polymers. In vivo, cleavage usually results from hydrolysis of the polymer. For example, the polymers of formulas I and II are usually characterized by a release rate of the biologically active substance in vivo that is controlled at least in part as a function of hydrolysis of the phosphoester bond of the polymer during biodegradation.

A variety of factors may affect the desired rate of hydrolysis of polymers of the subject invention, the desired softness and flexibility of the resulting solid matrix, rate and extent of bioactive material release. Some of such factors include: the selection of the various substituent groups, such as the phosphate group making up the linkage in the polymer backbone (or analogs thereof), the enantiomeric or diastereomeric purity of the monomeric subunits, homogeneity of subunits found in the polymer, and the length of the polymer. For instance, the present invention contemplates heteropolymers with varying linkages, and/or the inclusion of other monomeric elements in the polymer, in order to control, for example, the rate of biodegradation of the matrix.

To illustrate further, a wide range of degradation rates may be obtained by adjusting the hydrophobicities of the backbones or sidechains of the polymers while still maintaining sufficient biodegradability for the use intended for any such polymer. Such a result may be achieved by varying the various functional groups of the polymer. For example, the combination of a hydrophobic backbone and a hydrophilic linkage produces heterogeneous degradation because cleavage is encouraged whereas water penetration is resisted. In another example, it is expected that use of substituent on phosphate in the polymers of the present invention that is lipophilic, hydrophobic or bulky group would slow the rate of degradation. Thus, release is usually faster from polymer compositions with a small aliphatic group sidechain than with a bulky aromatic sidechain.

Figure 3:
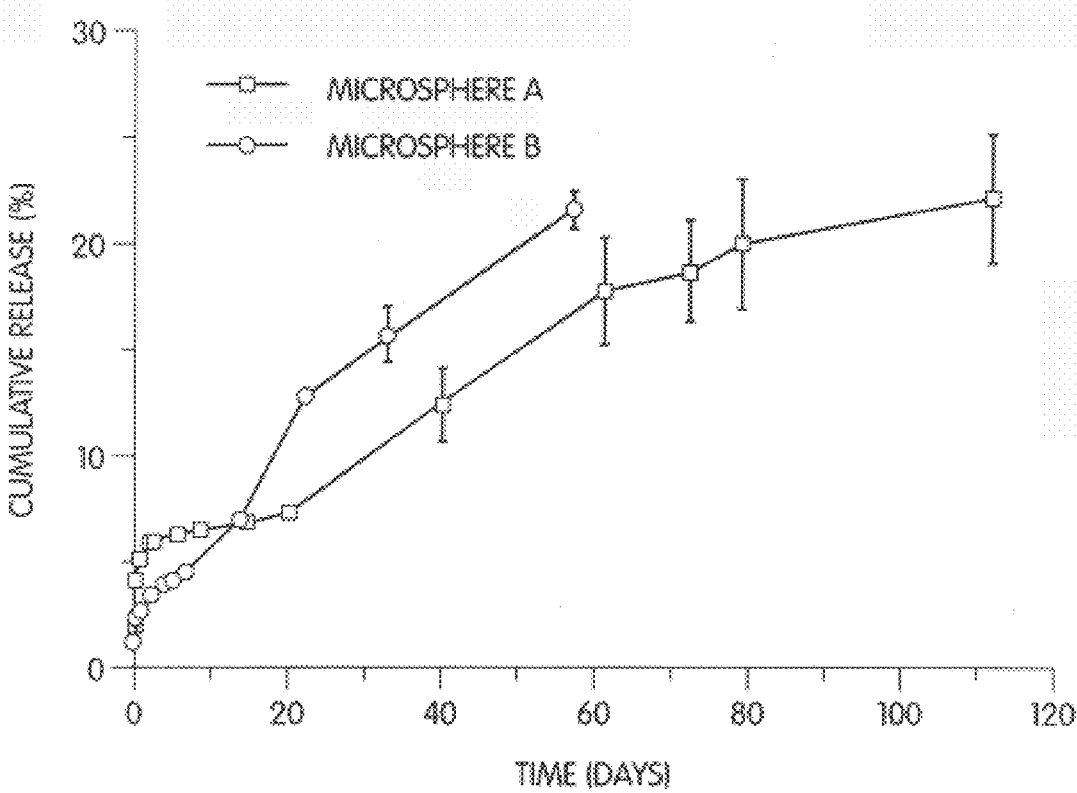
FIG. 3: Release of DNA from microsphere in PBS at 37° C.
Figure 10:
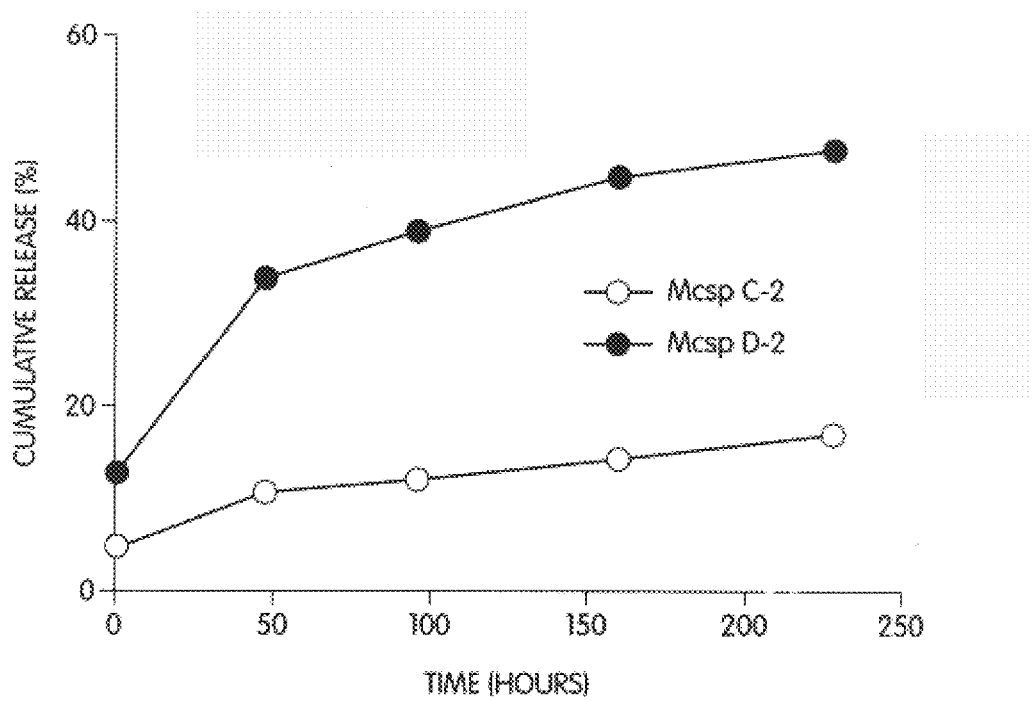
FIG. 10: In vitro release of DNA from P(DAPG-EOP) microspheres in PBS at 37° C.
Figure 11:
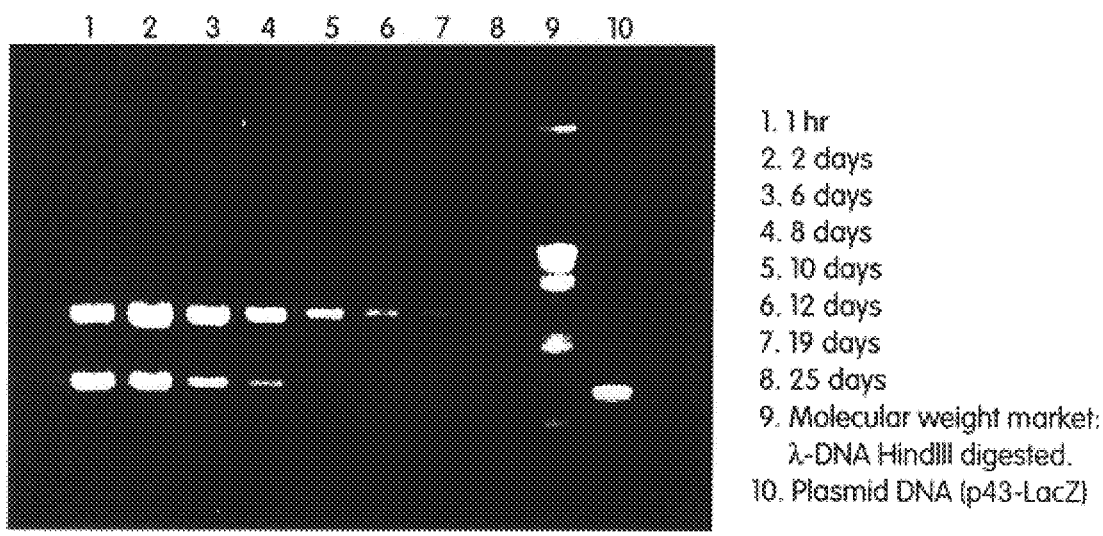
FIG. 11: LacZ plasmid DNA released from P(DAPG-EOP) microspheres containing 1.8% p43-LacZ DNA and 9% mouse serum albumin (MSA). (Release was performed at 37° C. in PBS).

One protocol generally accepted in the field that may be used to determine the release rate of any nucleic acid or other material loaded in the polymer matrices of the present invention involves degradation of any such matrix in a 0.1 M PBS solution (pH 7.4) at 37° C. Examples of this protocol are presented in Examples 4, 7, 8 and 9 below, and results from such protocols are depicted in FIGS. 3, 10 and 11. For purposes of the present invention, the term "PBS protocol" is used herein to refer to such protocol.

In certain instances, the release rates of different polymer systems of the present invention may be compared by subjecting them to such a protocol. In certain instances, it may be necessary to process polymeric systems in the same fashion to allow direct and relatively accurate comparisons of different systems to be made. For example, the present invention teaches several different means of formulating the polymeric matrices of the present invention. Such comparisons may indicate that any one polymeric system releases incorporated material at a rate from about 2 or less to about 1000 or more times faster than another polymeric system. Alternatively, a comparison may reveal a rate difference of about 3, 5, 7, 10, 25, 50, 100, 250, 500 or 750. Even higher rate differences are contemplated by the present invention and release rate protocols.

In certain embodiments, when formulated in a certain manner, the release rate for polymer systems of the present invention may present as mono- or bi-phasic. Release of any material incorporated into the polymer matrix, which is often provided as a microsphere, may be characterized in certain instances by an initial increased release rate, which may release from about 5 to about 50% or more of any incorporated material, or alternatively about 10, 15, 20, 25, 30 or 40%, followed by a release rate of lesser magnitude.

The release rate of any incorporated material may also be characterized by the amount of such material released per day per mg of polymer matrix. For example, in certain embodiments, the release rate may vary from about 1 ng or less of any incorporated material per day per mg of polymeric system to about 5000 or more ng/day.mg. Alternatively, the release rate may be about 10, 25, 50, 75, 100, 125, 150, 175, 200, 250, 300, 350, 400, 450, 500, 600, 700, 800 or 900 ng/day.mg. In still other embodiments, the release rate of any incorporated material may be 10,000 ng/day.mg or even higher. In certain instances, materials incorporated and characterized by such release rate protocols may include nucleic acid, therapeutic agents, fillers, and other substances.

In another aspect, the rate of release of any material from any polymer matrix of the present invention may be presented as the half-life of such material in the such matrix.

In addition to the embodiment involving protocols for in vitro determination of release rates, in vivo protocols, whereby in certain instances release rates for polymeric systems may be determined in vivo, are also contemplated by the present invention. Other assays useful for determining the release of any material from the polymers of the present system are known in the art.

6. Exemplary Uses

A. Nucleic Acids and Genes

A variety of genes and other nucleic acids may be incorporated into the subject microspheres for use in in vitro and in vivo transfection systems. These recombinant sequences may be transcribable to RNA and/or expressible as protein molecules which render them useful as therapeutic agents.

Proteins of use in gene therapy include various hormones, growth factors, enzymes, lymphokines, cytokines, receptors, and the like. For example, the vectors of the present invention may be used for direct gene replacement therapy, as in the case of replacing the function of a non-functional gene. Such direct replacement therapies have useful veterinary applications as well.

Among the genes that may be transferred in accordance with the invention are those encoding polypeptides that are absent, are produced in diminished quantities, or are produced in mutant form in individuals suffering from a genetic disease. Other genes of interest are those that encode proteins that have been engineered to circumvent a metabolic defect or proteins that, when expressed by a cell, may adapt the cell to grow under conditions where the unmodified cell would be unable to survive, or would become infected by a pathogen.

In addition the vectors may be used to produce anti-sense nucleic acids in target cells. Antisense therapy involves the production of nucleic acids that bind to a target nucleic acid, typically an RNA molecule, located within cells. The term antisense is so given because the oligonucleotides are typically complementary to mRNA molecules ("sense strands") which encode a cellular product targeted to selected cellular or viral gene expression products.

Exemplary modes by which sequences may be targeted for therapeutic applications include: blocking the interaction of a protein with an RNA sequence (e.g., the interaction of RNA virus regulatory proteins with their RNA genomes); and targeting sequences causing inappropriate expression of cellular genes.

In addition, the vectors of the present invention may be used to deliver sequences encoding catalytic RNA molecules into cells. For example, DNA sequences encoding a ribozyme of interest may be cloned into a vector of the present invention. Such a ribozyme may be a hammerhead ribozyme capable of cleaving a viral substrate, such as the Human Immunodeficiency Virus genome or an undesirable messenger RNA, such as that of an oncogene. The DNA-encoding ribozyme sequences may be expressed in tandem with tRNA sequences, with transcription directed from, for example, mammalian tRNA promoters.

In another embodiment, the microspheres may be used to deliver a nucleic acid which is itself a "decoy", or which is transcribable by the host cell to provide a decoy nucleic acid. A decoy nucleic acid is a nucleic acid having a sequence recognized by a regulatory nucleic acid binding protein (i.e., a transcription factor). Upon expression, the transcription factor binds to the decoy nucleic acid, rather than to its natural target in the genome. Useful decoy nucleic acid sequences include any sequence to which a transcription factor binds.

In still other embodiments, the subject microspheres may be used to transfect a cell with a recombinant gene encoding a "transdominant" protein. Such proteins may be dominant positive (agonists) or dominant negative (antagonists) with respect to all or a portion of the biological activities of a wild-type protein.

In general, the subject recombinant genes are provided in the form of an expression vector comprising the coding sequence operably linked to at least one regulatory sequence. Operably linked is intended to mean that the nucleotide sequence is linked to a regulatory sequence in a manner which allows expression of the coding sequence, wherein "expression" refers to transcription and translation in the case of a polypeptide or only transcription in the case of RNA. Regulatory sequences are art-recognized and are selected to direct expression of the coding sequence in the intended host cell. Accordingly, the term regulatory sequence includes promoters, enhancers and other expression control elements.

Exemplary regulatory sequences are described in Goeddel; Gene Expression Technology: Methods in Enzymology, Academic Press, San Diego, Calif. (1990). For instance, any of a wide variety of expression control sequences that control the expression of a DNA sequence when operatively linked to it may be used in these vectors to express recombinant gene sequences. Such useful expression control sequences, include, for example, the early and late promoters of SV40, adenovirus or cytomegalovirus immediate early promoter, the promoter for 3-phosphoglycerate kinase or other glycolytic enzymes.

In certain instances, the coding sequence will be operably linked to an inducible promoter. Several inducible promoter systems have been described, including those controlled by heavy metals (Mayo, K. E. et al., Cell 29:99–108 (1982)), RU-486, a progesterone antagonist (Wang, Y. et al., Proc. Natl. Acad. Sci. (USA) 91:8180–8184 (1994)), steroids (Mader & White, Proc. Natl. Acad. Sci. (USA) 90:5603–5607 (1993)) and tetracycline (Gossen & Bujard, Proc. Natl. Acad. Sci. (USA) 89:5547–5551 (1992)).

It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

The recombinant gene which is employed may result in an intracellular product, i.e., retained in the cell, in the cytoplasm or organelle, e.g., the nucleus, in transport to a membrane, either an intracellular membrane or the cell membrane, or for secretion. In certain embodiments, particularly where the recombinant gene encodes a polypeptide product, it will be desirable for the gene product to be secreted or at least a portion of the protein presented on the extracellular surface of the host cell. Proteins may be directed for secretion by providing the natural secretion signal sequence, if available, or a heterologous secretion signal sequence. In some situations, where the soluble protein of interest is a fragment of a larger protein, it may be necessary to provide a signal sequence with such protein, so that upon secretion and processing at the processing site, the desired protein will have the natural sequence. Examples include growth hormone, Factor VIII, Factor IX, cytokines, angiogenic factors, transforming growth factors (TGFs), antagonists of cytokine receptors, glucose transporters, insulin receptors, contraceptives, or addressins to promote adhesion and migration to specific sites.

The expression vector may also include a marker for selection of host cells which contain the construct, particularly where the subject transfection system is to be used as part of an ex vivo gene therapy protocol. Normally, the marker will allow for positive selection, in providing protection from one or more cytotoxic agents. For example, neomycin resistance may be employed, where the cells may be selected with G418, dihydrofolate reductase may be employed for resistance to methotrexate, the cell sorter may be used to select cells expressing LacZ, and the like. The marker may be an inducible or non-inducible gene, so that selection may occur under induction or without induction.

The vector may also include a replication origin and such other genes which are necessary for replication in the host. The replication system comprising the origin and any proteins associated with replication encoded by the particular virus may be included as part of a construct. Care must be taken in selecting the replication system, so that the genes which are encoded for replication do not provide for transformation of the myoblasts. Illustrative replication systems include Epstein-Barr virus (Margolskee et al., (1988) Mol. Cell. Biol. 8:2837–2847). Alternatively, replication defective vehicles may be employed, particularly replication-defective retroviral vectors. These vectors are described by Price et al., (1987) Proc. Natl. Acad. Sci. 84:156–160 and Sanes, et al., (1986) EMBO J. 5:3133–3142. The final vehicle construct may have one or more genes of interest. Either a cDNA gene or a chromosomal gene may be employed.

To further illustrate exemplary uses of the subject methods and reagents, the following list indicates various genes of interest and associated diseases, as appropriate, for which the polymers, polymeric systems and microspheres of the present invention may be employed for gene therapy:

(i) Single gene defects:
   Factor IX and Factor VIII (hemophilias: clotting disorders)
   alpha-1-antitrypsin (emphysema)
   growth hormone (inherited and acquired growth hormone deficiency)
   adenosine deaminase (other immunodeficiency disorders)
   enzyme defects (metabolic disorders)
   dystrophin (Duchenne and Becker muscular dystrophy)

(ii) Cancer:
   interferon (leukemia)
   Interleukin-2 (T-cell activator: leads to tumor shrinkage)
   leuprolide:analog of human gonadotropin (ovarian and testicular)
   asparaginase (leukemia)
   monoclonal antibodies (specific IgG) to specific proteins
   granulocyte colony stimulating factor (all cancers: allows higher doses of chemotherapy)

(iii) Brain:
   glucocerebrosidase (other lysosomal storage disorders; Tay Sachs)
   Levodopa (Parkinson's)
   nerve growth factor (Alzheimer's)

(iv) Regulated expression systems:
   insulin (diabetes)
   glucose transporter (diabetes)
   growth factors: IGF-I and IGF-II (v) Infectious diseases:
   delivery of antisense sequences, toxin genes, or other genes into cells to interfere with expression of the pathogenic genetic functions (vi) Contraception:
   antibody to human chorionic gonadotropin
   antibodies to zona pellucida antigens or sperm antigens
   progesterone antagonist (vii) Pain:
   endorphins (dynorphin): endogenous opiates (viii) Clotting disorders:
   Factor VIII and Factor IX (hemophilias)
   tissue plasminogen activator (ix) Organ and cell transplants:
   antibody to CD4 (HLA)

(x) AIDS:
   growth hormone to stimulate lymphocyte proliferation
   CD4 protein as a decoy to keep virus from interacting with CD4+cells (xi) Other:
   hormones, serum proteins, other humoral or diffusible proteins, and low molecular weight metabolic products In yet another embodiment, the subject compositions may be used to deliver a "gene activation" construct which, by homologous recombination with a genomic DNA, alters the transcriptional regulatory sequences of an endogenous gene. For instance, the gene activation construct may replace the endogenous promoter of a gene with a heterologous promoter, e.g., one which causes consitutive expression of the gene or which causes inducible expression of the gene under conditions different from the normal expression pattern of the gene. A variety of different formats for the gene activation constructs are available. See, for example, PCT publications WO93/09222, WO95/31560, WO96/29411, WO95/31560 and WO94/12650.

In certain embodiments, the nucleotide sequence used as the gene activation construct may be comprised of (i) DNA from some portion of the endogenous gene (exon sequence, intron sequence, promoter sequences, etc.) which direct recombination and (ii) heterologous transcriptional regulatory sequence(s) which is to be operably linked to the coding sequence for the genomic gene upon recombination of the gene activation construct.

The gene activation construct is inserted into a cell, and integrates with the genomic DNA of the cell in such a position so as to provide the heterologous regulatory sequences in operative association with the native gene. Such insertion occurs by homologous recombination, i.e., recombination regions of the activation construct that are homologous to the endogenous gene sequence hybridize to the genomic DNA and recombine with the genomic sequences so that the construct is incorporated into the corresponding position of the genomic DNA.

The terms "recombination region" or "targeting sequence" refer to a segment (i.e., a portion) of a gene activation construct having a sequence that is substantially identical to or substantially complementary to a genomic gene sequence, e.g., including 5' flanking sequences of the genomic gene, and may facilitate homologous recombination between the genomic sequence and the targeting transgene construct.

As used herein, the term "replacement region" refers to a portion of a activation construct which becomes integrated into an endogenous chromosomal location following homologous recombination between a recombination region and a genomic sequence.

The heterologous regulatory sequences, e.g., which are provided in the replacement region, may include one or more of a variety elements, including: promoters (such as constitutive or inducible promoters), enhancers, negative regulatory elements, locus control regions, transcription factor binding sites, or combinations thereof. Promoters/enhancers which may be used to control the expression of the targeted gene in vivo include, but are not limited to, the cytomegalovirus (CMV) promoter/enhancer (Karasuyama et al., 1989, J. Exp. Med., 169:13), the human β-actin promoter (Gunning et al. (1987) PNAS 84:4831–4835), the glucocorticoid-inducible promoter present in the mouse mammary tumor virus long terminal repeat (MMTV LTR)

(Klessig et al. (1984) Mol. Cell Biol. 4:1354–1362), the long terminal repeat sequences of Moloney murine leukemia virus (MULV LTR) (Weiss et al. (1985) RNA Tumor Viruses, Cold Spring Harbor Laboratory, Cold Spring Harbor, N.Y), the SV40 early or late region promoter (Bernoist et al. (1981) Nature 290:304–310; Templeton et al. (1984) Mol. Cell Biol., 4:817; and Sprague et al. (1983) J. Virol., 45:773), the promoter contained in the 3' long terminal repeat of Rous sarcoma virus (RSV) (Yamamoto et al., 1980, Cell, 22:787–797), the herpes simplex virus (HSV) thymidine kinase promoter/enhancer (Wagner et al. (1981) PNAS 82:3567–71), and the herpes simplex virus LAT promoter (Wolfe et al. (1992) Nature Genetics, 1:379–384).

In still other embodiments, the replacement region merely deletes a negative transcriptional control element of the native gene, e.g., to activate expression, or ablates a positive control element, e.g., to inhibit expression of the targeted gene.

B. Target Cells

The present invention may be used to introduce exogenous nucleic acid molecules into a variety of cells and tissues including, without limitation, muscle cells, endothelial cells, myeloid cells, bone marrow cells, stem cells (including hematopoietic and embryonic stem cells), lymphocytes, hepatocytes, fibroblasts, lung epithelial cells, embryonic cells, and nerve cells. In certain embodiments, the subject transfection system is used to transfect muscle or other cells of myocytic lineage.

A salient feature of certain embodiments of the polymeric transfection system of the present invention is the property of being able to transduce both proliferating and nonproliferating cells. This ability may be a significant advantage of the invention because of the proliferation characteristics of many of the target cells which one would like to transduce in various gene therapy protocols. In particular, many important target cells may alter their properties in undesirable ways when they divide, or they may divide very slowly, or they may not divide at all. Thus, the present invention may be useful in the transduction of such cells as normal muscle cells, normal hepatocytes, hematopoietic stem cells, neurons, quiescent lymphocytes, and normal epithelial cells (where "normal" refers only to the proliferative index of the cells). In terms of clinical practice, the transfection system of the present invention is useful in the treatment of a broad range of inherited and acquired diseases and medical conditions including, without limitation, hematologic diseases, cardiopulmonary diseases, endocrinological diseases, transplantation associated disorders, autoimmune disorders, neurodegenerative diseases, neoplasias, and the like.

(i) Muscle

The subject vectors may also be used to tranduce muscle cells in vitro and in vivo. Muscle is an important target for gene therapy in the treatment of several muscle and nerve diseases. Controlled gene expression in muscle may also be used to express genes that invoke an immune response, as well as to produce sustained levels of proteins that act on systemic disease.

Another reason that muscle may be used as a site for the delivery and expression of polynucleotides in a number of therapeutic applications is because animals have a proportionately large muscle mass which is conveniently accessed by direct injection through the skin; for this reason, a comparatively large dose of the subject gene therapy vectors may be deposited in muscle by single or multiple injections, and the nature of the slow-release microspheres may extend the gene therapy over long periods of time.

For instance, muscle disorders related to defective or absent gene products may be treated by introducing constructs coding for a non-secreted gene product into the diseased muscle tissue. In a another strategy, disorders of other organs or tissues due to the absence of a gene product, and which results in the build-up of a circulating toxic metabolite may be treated by introducing the specific therapeutic polypeptide into muscle tissue where the non-secreted gene product is expressed and clears the circulating metabolite. In yet another strategy, a construct coding for a secretable therapeutic polypeptide may be injected into muscle tissue from where the polypeptide is released into the circulation to seek a metabolic target. In still another embodiment, in immunization strategies, muscle cells may be injected with constructs coding for immunogenic peptides, and these peptides will be presented by muscle cells in the context of antigens of the major histocompatibility complex to provoke a selected immune response against the immunogen.

(a) Nucleic Acid Vaccines

In one embodiment, the subject polymeric transfection system may be used to form nucleic acid vaccines, e.g., DNA vaccines, for immunization against pathogens, cancer, and the like. DNA vaccination presents a number of features of potential value. Multiple antigens may included simultaneously in the vaccination. Such vaccination may work even in the presence of maternal antibodies.

DNA vaccination may be applied to eliminate or ameliorate existing disease or conditions, including chronic infectious diseases. For instance, the subject DNA vaccines may be used for immunizing subjects against such infections as HSV, HIV, HCV, influenza, malaria, Ebola, hepatitis B, pappillomavirus and the like. Moreover, the DNA vaccines may also be employed as part of a protocol for induction of tolerance, such as in the treatment of allergies and other autoimmune conditions, such as multiple sclerosis, Type I diabetes, and rheumatoid arthritis.

The goal of vaccination is the induction of protective immunity. The target was once limited to infectious diseases, but has now broadened to include treatment of tumors, allergy, and even autoinimune diseases. The injection of naked plasmid DNA results in the expression of the encoded antigen by muscle cells, and perhaps APCs, resulting in the induction of protective CTLs as well as antibody responses. This method of "genetic immunization" with polynucleic acid vaccines (PNV) may represent a significant advance in vaccination technology because it may be used repeatedly to immunize to different antigens while avoiding the risk of an infectious virus and the problem of the immune response to the vector.

DNA vaccination using the polymer system of the present invention may produce different results from other vaccination efforts using DNA, such as naked injection of DNA. The pattern of antigen express, both temporally and spatially, may differ from naked injection of DNA.

Most efforts to generate CTL responses have either used replicating vectors to produce the protein antigen within the cell, or they have focused upon the introduction of peptides into the cytosol. Both of these approaches have limitations that may reduce their utility as vaccines. Retroviral vectors have restrictions on the size and structure of polypeptides that may be expressed as fusion proteins while maintaining the ability of the recombinant virus to replicate (Miller, (1992) Curr. Top. Microbiol. Immunol. 158:1), and the effectiveness of vectors such as vaccinia for subsequent immunizations may be compromised by immune responses against the viral particle (Cooney et al., (1991) Lancet 337:567). Also, viral vectors and modified pathogens have inherent risks that may hinder their use in humans.

The polymeric transfection systems of the present invention may be used to deliver a coding sequence for an antigen(s) as part of a genetic immunization protocol. U.S. Pat. No. 5,783,567 and WO 94/04171 present a number of potential polypeptide sequences for inducing an immunogenic response. Because the subject delivery systems may be formulated with any of a wide range of vectors, issues of size limitation may be overcome. Moreover, the choice of vector may avoid the problems associated with the use of pathogens, such as retroviral vectors, associated with the prior art efforts at genetic vaccines.

As described in the appended examples, the subject transfection system may elicit a strong immune response even at low dose. The choice of encapsulation formulations, along with selection of transcriptional regulatory sequences, may be used to optimize the vaccine response. For example, the polymer matrix in which the nucleic acid or other material is incorporated, and any oligomers of monomers of such polymer, may serve as an adjuvant, wherein an "adjuvant" is a substance that in combination with specific antigen may produce more immunity than the antigen alone. The size of any microspheres of the subject polymer matrix may affect immunogenicity. Additional adjuvants may be administered to enhance the inherent adjuvant effect of the microspheres or polymer matrix.

By controlling the rate of release from the polymer matrix of the sequence giving rise to the antigen, it may be possible to prepare a single dose vaccine to replace a vaccination protocol requiring an initial vaccination followed by booster doses.

In another aspect of the present invention, a variety of DNA vaccination techniques may be employed with the polymer systems of the present invention to elicit a stronger immune response. For example, in certain embodiments, a naked nucleic acid, such as DNA, may be administered along with a polymeric system of the present invention loaded with the same nucleic acid or, alternatively, a different nucleic acid or acids (as well as possibly other materials). In this example, the initial dose of naked nucleic acid followed by release of nucleic acid from the polymeric system may result in a more effective vaccination.

In one embodiment, the subject method may be used as part of a vaccination against microbial pathogens. A major obstacle to the development of vaccines against viruses and bacteria, particularly those with multiple serotypes or a high rate of mutation, against which elicitation of neutralizing antibodies and/or protective cell-mediated immune responses is desirable, is the diversity of the external proteins among different isolates or strains. Since cytotoxic T-lymphocytes (CTLs) in both mice and humans are capable of recognizing epitopes derived from conserved internal viral proteins (Yewdell et al., (1985) PNAS 82:1785; Townsend, et al., (1986) Cell 44:959; McMichael et al., (1986) J. Gen. Virol. 67:719); Bastin et al., (1987) J. Exp. Med. 165:1508; Townsend and H. Bodmer, (1989) Annu. Rev. Immunol. 7:601), and are thought to be important in the immune response against viruses (Lin et al. (1981) J. Exp. Med. 154:225; Gardner et al., (1974) Eur. J. Immunol. 4:68; Taylor et al. (1986) Immunol. 58:417), efforts have been directed towards the development of CTL vaccines capable of providing heterologous protection against different viral strains.

Those skilled in the art will recognize appropriate epitopes for use generating an immunizing form of the subject polymeric transfection system. It is known that CTLs kill virally- or bacterially-infected cells when their T cell receptors recognize foreign peptides associated with MHC class I and/or class II molecules. These peptides may be derived from endogenously synthesized foreign proteins, regardless of the protein's location or function within the pathogen. By recognition of epitopes from conserved proteins, CTLs may provide heterologous protection. In the case of intracellular bacteria, proteins secreted by or released from the bacteria are processed and presented by MHC class I and II molecules, thereby generating T-cell responses that may play a role in reducing or eliminating infection.

In an exemplary embodiment, the subject method may be used to produce a protective vaccination against infection by Mycobacterium tuberculosis. Genes encoding Mycobacterium tuberculosis proteins may cloned into eukaryotic expression vectors, and formulated into the subject microspheres for expression of the encoded proteins in mammalian muscle cells in vivo.

(b) Treatment of Dystrophic Muscle Diseases

Another application of the subject method is in the treatment of muscular dystrophy. The genetic basis of the muscular dystrophies is beginning to be unraveled. The gene related to Duchenne/Becker muscular dystrophy has recently been cloned and encodes a rather large protein, termed dystrophin. An attractive approach would be to directly express the dystrophin gene within the muscle of patients with Duchennes. Because most patients die from respiratory failure, the muscles involved with respiration would be a primary target.

The present transfection system may be used to express high levels of the following genes specifically in muscle tissue; the full length Duchenne's muscular dystrophy gene (dystrophin), the related sequence of the gene responsible for Becker's muscular dystrophy; myotonin protein kinase; alph alpha-subunit of Na+channels; the 50 kd-dystrophyn associated glycoprotein; myophosphorylase; phosphofructokinase; acid maltase; glycogen debrancing enzyme; phosphoglycerate kinase; phosphoglycerol mutase; lactate dehydrogenase; and carnitine palmitoyl transferase. The appropriate gene for the particular afflicted individual may be determined through genetic screening as known in the art.

(c) Treatment of Heart Tissue

In another embodiment, gene transfer into heart tissue using the subject polymeric transfection system may be used to treat both genetic and acquired heart disease. There are a variety of diseases and conditions affecting the heart tissue that could benefit from gene therapy. Pathogenic changes associated with hereditary, environmental and infectious disease may selectively or generally affect the heart endocardium, myocardium, epicardium or pericardium.

The myocardium is an example of a target for gene therapy directed to the heart. The myocardium is the thickest layer of the heart containing the cardiac muscle cells, the impulse-conducting system and connective tissue. Myocardial disease occurs in many forms of heart disease including myocardial infarction, rheumatic heart disease, and hypertensive heart disease. A number of myocardial pathologies involve inflammatory reactions that may impair heart function and persist for long periods of time. Untreated, the inflammatory reaction may produce focal necrosis and compromise cardiac function. In fact, many forms of myocarditis have unknown etiologies. Here the single most apparent symptom upon autopsy is an overwhelming immune response isolated within the cardiac muscle tissue. For these inflammatory diseases, gene therapy may be used to control the immune response. For example, antisense oligonucleotides may be used to control lymphokine release from inflammatory cells.

A construct which is transcribed to an antisense molecule may be designed once a DNA sequence for a particular gene is identified. For example, elevated IL-6 levels are observed both in cardiac inflammation associated with adventitious agents and autoimmune disease. It may therefore be beneficial to deliver IL-6 "antisense construct", e.g., which is transcribed to an antisense RNA which hybridizes to IL-6 mRNA, to control IL-6 release from immune cells within the heart. The cDNA sequence for IL-6 is provided in a publication by Hirano et al. (Nature 324:73–76, 1986) and Green et al. review the use and application of antisense polynucleotide to regulate protein expression (Ann. Rev. Biochem. 55:569–597, 1986). Tumor necrosis factor (TNF-α) is also implicated in IL-6 production and levels of TNF-α are increased at the site of inflammation. Mechanism to modulate TNF-α expression will prove beneficial for controlling localized immune responses in the heart. The sequence for TNF-α is provided by Pennica et al. (Nature 312:724, 1984). Alternatively, transforming growth factor (TGF-β) may be used to limit lymphocyte proliferation. An expression construct encoding a TGF-β protein may be introduced directly into heart cells to produce TGF-β thereby limiting lymphocyte proliferation within a localized area. The cDNA sequence for TGF-β is found in a publication by Derynck et al. (Nature 316:701–705, 1985). Similarly other growth factors or regulatory molecules may be used to selectively control other cells involved in the immune response.

If the causative agent for myocarditis is identifiable, then antisense polynucleotides or other regulatory proteins may be injected or introduced into the myocardium to act on that causative agent. These polynucleotide sequences may additionally be combined with sequences that encode polypeptides that control the immune response. Myocarditis is associated with rheumatic fever (Group A Streptococci), diphtheria, typhoid fever, scarlet fever and organisms causing infective endocarditis. Viral disorders causing myocarditis include influenza, poliomyelitis, mumps, measles, Epstein Barr virus, Coxsackie and ECHO viruses. In addition most rickettsial infections also induce some myocardial damage. Parasitic infections that may induce myocarditis and create cardiac abnormalities include Chagas' disease (Trypanosoma cruzi), toxoplasmosis and trichinosis. In addition, systemic lupus erythromatosus, scleroderma and generalized hypersensitivity reactions may also induce cardiac inflammation. More rarely, Mycoplasma pneumoniae and Toxoplasma gondii may induce myocarditis. Those conditions of unknown etiology that affect cardiac tissue include Fiedler's and giant cell myocarditis. These infectious agents induce inflammatory responses that may be controlled by the secretion of immunoregulatory polypeptides encoded by constructs delivered by the subject polymeric compositions.

Primary cardiomyopathies include arrhythmias, emboli valve insufficiency and ventricular obstruction. These pathologies may be either familial or acquired and may be amenable to gene therapy. However, for many of these myopathies, the specific causative agent has not yet been identified. Some myopathies, particularly those characterized by restricted ventricular filling, are primarily due to the overproduction of a given protein and would therefore benefit from gene therapy. For example, endocardial fibroelastosis is characterized by focal or diffuse cartilage-like fibroelastic thickening of the mural endocardium that may extend into the myocardium. The use of polynucleotide sequences, in accordance with the present invention, to control protein secretion would be of value.

Similarly, amyloidosis, the accumulation of amyloid protein, effects the heart and may be controllable by the therapy contemplated herein. Polynucleotide sequences encoding protein associated with amyloidosis are available in the literature and are readily identifiable to those with skill in the art. The introduction of antisense sequences by the subject lentiviral vectors to control over-expression of a molecule or alternatively, the introduction of sequences coding for functional protein to correct the defective enzyme or regulatory protein responsible for the overproduction of a particular molecule, could cessate further deposit accumulation.

Some diseases thought to be "connective tissue" diseases also involve the heart. These include Rheumatoid arthritis, Lupus erythematosus, polyarthritis and scleroderma. Elevated levels of IL-6 are observed in systemic lupus erythematosus (SLE). As noted above, antisense directed to IL-6 may be beneficial for controlling localized immune responses within cardiac tissue. In addition, Linker-Israeli et al. (J. Immunol. 147:117, 1991) have shown that TNF-α is useful to inhibit immune cell stimulation of SLE cells in vitro. Therefore the invention disclosed herein may additionally comprise the delivery of gene sequences encoding TNF-α (Pennica et al. supra.). The immune response within the heart may be controlled using the methods detailed herein.

Individuals with diabetes develop cardiomyopathies over time. Increased levels of atrial natriuretic peptide (ANP) mRNA is found in the heart tissue of some diabetics. The changes in levels of ANP synthesis occur before cardiomyopathic histological changes. ANP levels are even greater in diabetic conditions combined with hypertension (Drexler et al. (1989) Circulation 79:620). Localized levels of ANP may be reduced through the delivery of polynucleotide directed at limiting ANP synthesis. The particular gene sequence chosen will correct a cellular defect associated with a particular cardiac disease or pathology. The gene sequence could encode a range of molecules as discussed and these molecules may be engineered to be expressed either intracellularly or extracellularly. Further, the polynucleotide may be a regulatory molecule of itself (i.e. anti-sense or the like) or encode regulatory or immunoregulatory molecules. The polynucleotide may additionally encode enzymes, hormones, and growth factors.

Cardiac treatment may be performed either prophylactically or on individuals with known cardiac sequelae. Characteristic symptoms of myocardial malfunction include, but are not limited to, arrhythmias, heart pain, cardiac enlargement, and congestive heart failure (predominantly of the right side). Infusion of calcitonin gene related peptide, an alternate product in calcitonin synthesis, is beneficial for the treatment of congestive heart failure (Shekhar et al., Am. J. Cardiol. 67(8):732–736, 1991). Thus it is additionally contemplated that the subject method may be used to deliver, to the hearts of those patients with congestive heart failure, expression constructs encoding enzymes involved calcitonin synthesis. Inhibitors of angiotensin converting enzyme are beneficial in controlling experimental cardiac hypertrophy and congestive heart failure (Soubrier et al. (1988) PNAS 85:9386; and Michel (1990) Eur. Heart J. 11 Suppl. D:17). The subject polymeric system may be used to deliver of a recombinant gene encoding protein, or transcribable into an antisense nucleic acid, which inhibits angiotensin converting enzyme.

In other embodiments, the subject method may be used to cause the ectopic expression of adenosine receptors on the surface of the heart. Adenosine is a chemical produced by the heart that regulates heart function and protects the heart during periods of low oxygen supply.

(d) Myocytes as Source of Secreted, Recombinant Proteins

In another embodiment, the subject polymeric compositions may be used to cause the ectopic expression, in myocytic cells, of a gene encoding a secreted protein. For example, the subject method may be used to deliver an expression vector cytokines, growth factors, (e.g., EGF, FGF, etc.), colony stimulating factors, interferons, surface membrane receptors, insulin or the like.

In one embodiment, the subject transfection system may be used as part of a gene therapy protocol in the treatment of inflammatory disorders, lupus and colitis. To illustrate, the polymeric delivery system of the present invention may be used to treat certain forms of arthritis by intramuscular gene therapy by ectopic expression of a transforming growth factor (TGF). Song et al. (1998) J Clinical Investigation 101 (12) recently reported that plasmid DNA, injected directly into muscle tissue, encoding transforming growth factory suppresses chronic disease in a streptococcal cell wall-induced arthritis model. This procedure was observed to dramatically reduced chronic arthritis symptoms in the joints, and now offers an innovative approach for eventually treating human disease. In this report, researchers tested the TGF plasmid in a rat model for human rheumatoid arthritis. In this model, animals that are injected in the abdomen with a preparation of bacterial cell walls soon develop swollen and inflamed joints in the feet. The acute arthritic phase lasts several days and then develops into a long-term chronic condition that is marked by the erosion of cartilage and bone within the joints. When the animals were intramuscularly injected with TGF-encoding plasmids, a dramatic reduction in disease symptoms in the joints was observed. The number of affected joints and the amount of swelling in the joints were both substantially reduced.

This study also demonstrated that the manner in which the protein was administered to the animals determined whether or not the outcome was favorable. Injecting TGF directly into joints led to a worsening of the condition. On the other hand, injection of the protein into the abdomen or under the skin, which delivers TGF into the blood stream, dramatically improved symptoms. However, this route of delivery also carries the risk of bone marrow suppression, anemia, and formation of fibrous tissues in the kidneys-undesirable side effects associated with exposing the entire body to high levels of TGF. However, using the gene therapy approach rather than administration of the protein permits the production of a low-level supply of TGF that effects the inflammatory response in the joints without disrupting the balance of other bodily functions. The TGF expression system of Song et al., supra, may be adapted for delivery by the polymeric microspheres of the present invention.

In another embodiment, the subject polymer systems may be used to cause the ectopic expression of an angiogenic growth factor to stimulate the development of collateral arteries, e.g., as part of a "therapeutic angiogenesis" treatment approach. In an exemplary embodiment, the microspheres of the present invention are used to treat ischemic ulcers by ectopic expression of vascular endothelial growth factor (VEGF) in muscle of the afflicted limb.

To illustrate, Baumgartner et al. (1998) Circulation 97:1114 recently reported that preclinical studies have indicated that angiogenic growth factors may stimulate the development of collateral arteries. In that study, naked plasmid DNA encoding the 165-amino-acid isoform of human vascular endothelial growth factor (phVEGF(165)) was injected directly into the muscles of limbs of patients with non-healing ischemic ulcers. The investigators reported newly visible collateral blood vessels, qualitative evidence of improved distal flow in limbs, and marked improvement in healing of ischemic ulcers. The VEGF vectors of Baumgartner et al., supra, may be may be adapted for delivery by the polymeric microspheres of the present invention.

In still other embodiments, the subject method may be used for ectopic expression of growth hormone or insulin like growth factor I (IGF-I). Growth hormone is normally produced and secreted from the anterior pituitary and promotes linear growth in prepuberty children. Growth hormone acts on the liver and other tissues to stimulate the production of IGF-I. This factor is, in turn, responsible for the growth promoting effects of growth hormone. Further, this factor serves as an indicator of overall growth hormone secretion. Serum IGF-I concentration increases in response to endogenous and erogenous administered growth hormone. These concentrations are low in growth hormone deficiency. Insulin-like growth factors are one of the key factors that potentiate muscle development and muscle growth. Myoblasts naturally secrete IGF-I/IGF-II as well as its cognate binding proteins during the onset of fusion. This process coincides with the appearance of muscle specific gene products. In terminally differentiated muscle, signals propagated from passive stretch induced hypertrophy induce the expression of IGF genes. Many of the actions of IGFs on muscle result from interactions with the IGF-I receptor. The intramuscular delivery of an expression vector containing the sequence for growth hormone or IGF-I may be used to treat growth disorders. Since intramuscular expression using the subject compositions may lead to expression of the GH or IGF-I product for extended periods of time, the subject method may provide a long-term inexpensive way to increase systemic blood concentration of IGF-I in patients with growth hormone deficiency.

Moreover, growth hormone levels decline with increasing age. The levels in healthy men and women above age of 55 are approximately one third lower than the levels in men and women 18 to 33. This is associated with a decrease in the concentration of IGF-I. The decline in growth hormone and IGF-I production correlate with the decrease in muscle mass, termed senile muscle atrophy, and increase in adiposity that occur in healthy human subjects. Administering growth hormone three times a week to healthy 61 to 81 year old men who had serum levels below those of healthy younger men increased the serum IGF-I levels to within the range found in young healthy adults. This increase level led to increased muscle mass and strength and reduced body fat. The secretion of growth hormone is regulated by a stimulatory (growth hormone releasing hormone) and an inhibitory (somatostatin) hypothalamic hormone.

The transfection systems of the present application may be used to deliver expression vectors encoding growth hormone, the growth hormone releasing hormone (GHRH), or IGF-I. This versatility is important since the GHRH, GH, and IGF-I, while having equivalent desired effects on muscle mass, may have different side effects, or kinetics which will affect their efficacy. The expression of the growth factor releasing hormone might be more advantageous than the expression of either IGF-I or the growth hormone vectors transcripts. Since GHRH is reduced in the elderly it appears to be responsible for the lack of GH secretion rather than the anterior pituitary capability of synthesizing growth hormone, thus the increased expression of GHRH from muscle would increase GHRH levels in the systemic blood system and may allow for the natural diurnal secretion pattern of GH from the anterior pituitary. In this way, GHRH could act as the natural secretogogue, allowing for elevate secretion or release of GH from the hypothalamus of the elderly.

Thus, the application of vector systems described herein to express insulin-like growth factors through the ectopic expression of IGF-I, HG, or GHRH into adult muscle of the elderly is a long-term inexpensive way to increase systemic blood concentration of IGF-I in the elderly.

(e) Treatment of Atherosclerotic Cardiovascular Diseases

Atherosclerotic cardiovascular disease is a major cause of mortality in the United States and the world. The atherosclerotic plaque, the basic underlying lesion in atherosclerosis, contains cholesterol esters that are derived from circulating lipids. These circulating lipids are essential to the development of atherosclerosis. The plasma concentration of high density lipoprotein (HDL) is inversely related to the propensity for developing atherosclerosis. In the nascent state, HDL is secreted in the form of discoidal particles. These particles consist of a bilayer of phospholipids onto which the apolipoproteins (ApoA-I, ApoII and E) are embedded. HDL captures cholesterol esters by the action of an enzyme, lecithin-cholesterol acyltransferase. HDL is secreted from the liver, the small intestine and possibly other tissues.

The ApoA-I cDNA is 878 bp and encodes 267 amino acids, including the 24 amino acid propeptide. Increasing the circulating levels of HDL may influence or reverse cholesterol transport, and thus reduce the propensity for forming atherosclerotic plaques. The insertion of the human ApoA-I coding sequences into the expression vector of the present application may enhanced ApoA-I expression following transfection of that vector into skeletal muscle, and may be used to increases the plasma concentration of HDL.

(ii) Other Tissue

In another embodiment, the subject polymeric compositions may be used as part of a gene therapy protocol for treatment of liver diseases that are, for example, genetically based, as for example Wilson's disease, glycogen storage diseases, urea cycle enzyme defects, and Creigler-Najir disease. For example, the subject transfection system may be used to correct an inherited deficiency of the low density lipoprotein (LDL) receptor, and/or to correct an inherited deficiency of ornithine transcarbamylase (OTC), which results in congenital hyperammonemia.

In another embodiment, the subject constructs may, be used to treat acquired infectious diseases of the liver, such as diseases resulting from viral infection. For example, the vectors may be employed to treat viral hepatitis, particularly hepatitis B or non-A non-B hepatitis. For example, an microsphere of the present invention, containing a gene encoding an antisense gene, could be transduced into hepatocytes in vivo to inhibit viral replication. In this case, the infectious viral particle, which includes a vector including a structural hepatitis gene in the reverse or opposite orientation, may be introduced into hepttocytes, resulting in production of an antisense gene capable of inactivating the hepatitis virus or its RNA transcripts. Alternatively, the hepatocytes may be transduced with a vector which includes a gene encoding a protein, such as, for example, (α-interferon, which may confer resistance ti) the hepatitis virus.

Crigler-Najjar syndrome is an autosomal recessive disorder which causes severe jaundice in affected children. Mutation of both alleles of the bilirubin gulcuronosyl transferase (BUGT) gene results in an inability to excrete bilirubin, which then accumulates in the body. The resulting jaundice is unremitting, leading inevitably to brain damage (spasticity, deafness, dementia) and death. The genes for human BUGTs have been cloned by others and an animal model of this syndrome is available. The subject polymeric transfection system may be used to deliver the human BUGT gene to hepatocytes in vivo. The response to this gene transfer therapy may be easily monitored by measuring the patient's serun bilirubin level. Correction of the BUGT defect via gene therapy may provide an alternative to transplantation, the only other therapy currently available.

In another embodiment, the subject transfection system may be used to transfect neuronal cells. Most neurons do not divide at all. Accordingly, the prior art retroviral vector transduction systems generally may not efficiently be used with these cells. The microspheres of the invention, however, do not require cell proliferation and thus may be used to transduce neurons.

Endothelial cells which are contact inhibited, the usual state of such cells within the body, divide very slowly, if at all. Accordingly, the same considerations regarding transduction which apply to neurons also apply to endothelial cells.

In another embodiment of the present invention, DNA vaccination may use mucosal delivery, which allows for easy administration, reduced side-effects, and the possibility of frequent boosting without requiring trained medical personnel. Mucosal delivery of vaccines appears to be the only effective means of inducing immune responses in the mucosal secretions. Many pathogens enter the body through the mucosal tissues of the gut or the respiratory or genital tracts.

Another application of the subject transfection system is in the treatment of cystic fibrosis. The gene for cystic fibrosis was recently identified (Goodfellow, P. Nature, 341(6238): 102–3 (Sept. 14, 1989); Rommens, J. et al. Science, 245 (4922):1059–1065 (Sep. 8, 1989); Beardsley, T. et al., Scientific American, 261(5):28–30 (1989). Significant amelioration of the symptoms should be attainable by the expression of the dysfunctional protein within the appropriate lung cells. The bronchial epithelial cells are postulated to be appropriate target lung cells and they could be accessible to gene transfer following instillation of genes into the lung. Since cystic fibrosis is an autosomal recessive disorder one would need to achieve only about 5% of normal levels of the cystic fibrosis gene product in order to significantly ameliorate the pulmonary symptoms.

Biochemical genetic defects of intermediary metabolism may also be treated by the subject method. These diseases include phenylketonura, galactosemia, maple-syrup urine disease, homocystinuria, propionic acidemia, methylmalonic acidemia, and adenosine deaminase deficiency. The pathogenesis of disease in most of these disorders fits the phenylketonuria (PKU) model of a circulating toxic metabolite. That is, because of an enzyme block, a biochemical, toxic to the body, accumulates in body fluids. These disorders are ideal for gene therapy for a number of reasons. First, only 5% of normal levels of enzyme activity would have to be attained in order to significantly clear enough of the circulating toxic metabolite so that the patient is significantly improved. Second, the transferred gene could most often be expressed in a variety of tissues and still be able to clear the toxic biochemical. Similar transfection of pancreatic islet cells utilizing a polymeric transfection system described herein may prove useful in the treatment of insulin dependent diabetes mellitus.

7. Formulations of the Present Invention

The polymeric microspheres of the present invention may be administered by various means, depending on its intended use, as is well known in the art. For example, if polymer matrices of the present invention, often shaped as microspheres, are to be administered orally, it may be formulated as tablets, capsules, granules, powders or syrups. Alternatively, formulations of the present invention may be administered parenterally as injections (intravenous, intramuscular or subcutaneous), drop infusion preparations, or suppositories. For application by the ophthalmic mucous membrane route, polymer matrices of the present invention, often shaped as microspheres, may be formulated as eyedrops or eye ointments. These formulations may be prepared by conventional means, and, if desired, the polymer matrices may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agent!;, preservatives and antioxidants may be present in the supplements.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of polymer matrix which may be combined with a carrier material to produce a. single dose vary depending upon the subject being treated, and the particular mode of administration.

Methods of preparing these formulations or compositions include the step of bringing into association polymer matrices of the present invention., often shaped as microspheres, with the carrier and, optionally, one or more accessory ingredients. In general, the formulations are prepared by uniformly and intimately bringing into association a supplement or components thereof with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a supplement or components thereof as an active, ingredient. Polymer matrices of the present invention, often formed as microspheres, may also be administered as a bolus, electuary, or paste.

In solid dosage forms for oral administration (capsules, tablets, pills, dragees, powders, granules and the like), the supplement or components thereof is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds;; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the supplement or components thereof moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the supplement or component, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the supplement or components thereof, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more component with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations Containing such carriers as are known in the art to be appropriate.

Dosage forms for transdermal administration of an supplement or component includes powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required. For transdermal administration of transition metal complexes, the complexes may include lipophilic and hydrophilic groups to achieve the desired water solubility and transport properties.

The ointments, pastes, creams and gels may contain, in addition to a supplement or components thereof, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a supplement or components thereof, excipients such as lactose, talc, silicic acid, ; hydroxide, calcium silicates and polyamide powder, or mixtures of these substances. Sprays may additionally contain customary propellants, such as chlorofluorohydrocarbons and volatile unsubstituted hydrocarbons, such as butane and propane.

Components of the supplement may alternatively be administered by aerosol. This is accomplished by preparing an aqueous aerosol, liposonal preparation or solid particles containing the compound. A non-aqueous (e.g., fluorocarbon propellant) suspension could be used. Sonic nebulizers may be used because they minimize exposing the agent to shear, which may result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Ophthalmic formulations, eye ointments, powders, solutions and the like, are also contemplated as being within the scope of this invention.

Pharmaceutical compositions of this invention suitable for parenteral administration comprise one or more components of a supplement in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as. ethyl oleate.

Proper fluidity may be maintained, for example, by the use of coating materials, such as lecithin, by the maintenance of the required particle size in the case of dispersions, and by the use of surfactants.

8. Exemplification

EXAMPLE 1

Synthesis of Poly(L-lactide-co-ethyl-phosphite) [poly(LAEG-EOP), or P(LAEG-EOP)]

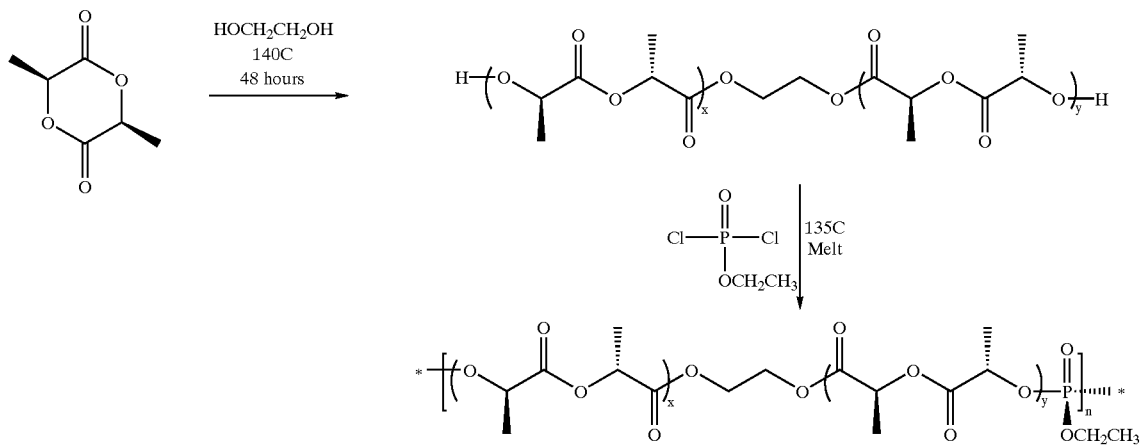

20 g (0.139 mole of (3S)-cis-3,6-dimethyl-1,4-dioane-2,5-dione (L-lactide) (obtained from Aldrich Chemical Company, recrystallized with ethyl acetate, sublimed, and recrystallizes with ethyl acetate again) and 0.432 g (6.94 mole ) of ehtylene glycol (99.8%, anhydrous, from Aldrich) were places in a 250 mL round-bottom flask flushed with dried argon. The flask was closed under vacuum and placed in an oven heated to 140° C. The flask was kept at this temperature for about 48 hours with occasional shaking.

The flask was then filled with dried argon and placed in oil bath heated to 135° C. Under an argon stream, 1.13 g of phosphorodichloridate was added with stirring. Under an argon stream, 1.13 g of ethyl phosphorodichlorate is added with stirring. After one hour of stirring, a low vacuum (about 20 mmHg) was applied to the system, and it was allowed to stand overnight. One hour before work-up, a high vacuum was applied. After cooling, the polymer was dissolved in 200 mL of chloroform and quenched into one liter of ether twice to obtain a an off-white precipitate, which was dried under vacuum.

EXAMPLE 2

Properties of P(LAEG-EOP)

A P(LAEG-EOP) polymer where (x or y)/n=10:1 was prepared as described above in Example 1. The resulting poly(phosphoester-co-ester) polymer was analyzed by GPC using polystyrene as a standard, and the resulting graph established an Mw of 33,000 and an Mn of 4800.

The viscosity was measured in chloroform ($CH_3Cl$) at 40° C. and determined to be 0.315 dL/g. The polymer was soluble in ethyl acetate, acetone, acetonitrile, chloroform, dichloromethane, tetrahydrofuran, N-methylpyrrolidone, dimethylformamide, and dimethyl sulfoxide. The polymer formed a brittle film, and the Tg was determined by DSC to be 51.5° C.

EXAMPLE 3

Synthesis of P(LAEG-HOP)

A second polymer, P(LAEG-HOP), having the following structure:

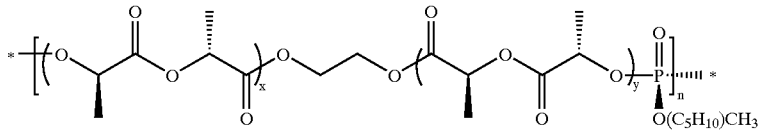

was also prepared by the method described in Example 1, except that hexyl phosphorodichloridate (HOP) was substituted for EOP (ehtyl phosphodichlorate).

EXAMPLE 4

Properties of P(LAEG-EOP) and P(LAEG-HOP)

The weight-average molecular weight (Mw) of the phosphoester-co-ester polymer of Example 1, P(LAEG-EOP), and the polymer of Example 3, P(LAEG-HOP), were determined, and samples of each were then allowed to remain exposed to room temperature air to test for ambient, unprotected storage capability. After one month, the Mw was again determined for each polymer. The results showed that, while the Mw for p(LAEG-EOP) was reduced by about one-third after a month of unprotected ambient conditions, the Mw for p(LAEG-HOP) remained fairly constant, even showing a slight increase.

Discs for degradation studies were then fabricated from each polymer by compression molding at 50° C. and a pressure of 200 MPa. The discs were 4 mm in diameter, 1.5 mm in thickness, and 40 mg in weight. The degradation studies were conducted by placing the discs in 4 mL of 0.1M PBS (pH 7.4) at 37° C. Duplicate samples were removed at different time points up to eight days, washed with distilled water, and dried under vacuum overnight. Samples were analyzed for weight loss and molecular weight change (GPC). Both polymers, P(LAEG-EOP) and P(LAEG-HOP), demonstrated acceptable degradation profiles.

EXAMPLE 5

In vivo Biocompatibility of P(LAEG-EOP)

A 100 mg polymer wafer was formed from P(LAEG-EOP) and, as a reference, a copolymer of lactic and glycolic acid ["PLGA (RG755)"] known to be biocompatible. These wafers were inserted between muscle layers of the right limb of adult SPF Sprague-Dawley rats under anesthesia. The wafers were retrieved at specific times, and surrounding tissues were prepared for histopathological analysis by a pathologist using the following scoring:

| Score | Level of Irritation |
| --- | --- |
| 0 | No irritation |
| 0–200 | Slight irritation |
| 200–400 | Mild irritation |
| 400–600 | Moderate irritation |
| >600 | Severe irritation |

The results of the histopathological analysis are as follows:

| | Days | | | | | |
| --- | --- | --- | --- | --- | --- | --- |
| Polymer | 3 | 7 | 14 | 30 | 60 | 120 |
| P(LAEG-EOP) | 130 | 123 | 180 | 198 | 106 | 99 |
| PLGA(RG755) | 148 | 98 | 137 | 105 | 94 | 43 |

EXAMPLE 6

Preparation of Copolymer Microspheres Containing FITC-BSA with 10% Theoretical Loading LEvel 100 mL of FITC-BSA solution (100 mg/mL dissolved in water) was added to a solution of 100 mg of P(LAEG-EOP) in 1 mL of methylene chloride,, and emulsified via sonication for 15 seconds on ice. The resulting emulsion was immediately poured into 5 mL of vortexing 1% solution of polyvinyl alcohol (PVA) in 5% NaCl, and vortexing was maintained for one minute. The emulsion thus formed was then poured into 20 mL of a 0.3% PVA solution in 5% NaCl, which was being stirred vigorously. 25 mL of a 2% solution of isopropanol was added, and the mixture was kept stirring for one hour to ensure complete extraction. The resulting microspheres were collected via centrifugation at 3000×g, washed 3 times with water, and freeze dried.

Different formulations of microspheres were made Ivy using as the second aqueous phase a 5% NaCl solution or a 5% NaCl solution also containing 1% PEG 8000. Yet another technique was used in evaporating the solvent by stirring the mixture overnight, thus forming microspheres by solvent evaporation.

EXAMPLE 7

Intramolecular Delivery of LacZ Plasmid Encapsulated in Microspheres Composed of Biodegradable Phosphate Chain-extended Poly(L-lactide)

To evaluate if a controlled release formulation may effect gene transfer in muscles and elicits similar immune responses as multiple naked DNA injections, we encapsulated the reporter gene LacZ in a new synthetic biodegradable polymer. The polymer is composed of phosphate bonds distributed between oligomeric blocks of lactide in the backbone. The phosphate bond accelerates the degradation of the polylactide, renders the polymer soluble in common organic solvents such as ethyl acetate and acetone, and provides a reactable side-chain for ligand conjugation or further manipulation of the physiochemical properties. These poly(L-lactide-phosphate)s exhibited good soft tissue biocompatibility and a relatively linear mass loss profile in vitro. Sustained release of low-molecular weight drugs and proteins from microsphere formulations has also been demonstrated (Mao, H.-Q., et al. (1997) *Proceedings of the Topical Conference on Biomaterials Carriers for Drug Delivery and Scaffold for Tissue Engineering*, Peppas, N. A., et al., eds. Los Angeles, Calif.). In this report, we studied the encapsulation and release of the p43-LacZ plasmid, and characterized the immune response to β-galactosidase as a model antigen in vivo.

(i) Preparation of Different Formulations of Microspheres with P(LAEG-EOP) Containing p43 LacZ pcDNA One hundred μL of pcDNA solution (10 mg/mL dissolved in TE buffer) was added to a solution of 100 mg of P(LAEG-EOP) in 1 mL of methylene chloride, and emulsified via sonication for 15 seconds on ice. The resulting emulsion vias immediately poured into 5 mL of vortexing 1% polyvinyl alcohol (PVA)-5% NaCl solution and maintained vortexing for 1 minute. This emulsion was then poured into 20 mL of 0.3% PVA-5% NaCl solution being stirred vigorously. An isopropanol solution (2%, 25 mL) was added and the mixture was kept stirring for 1 hour to ensure complete extraction. The resulting microspheres were collected via centrifugation at 3000×g, washed 3 times with water and freeze dried.

The blank microspheres were prepared in the same manner using water as the inner aqueous phase. Microspheres containing BSA were prepared according to the same method by incorporating 10:1 ratio of BSA in the pcDNA solution.

(ii) Estimation of Encapsulation Efficiency and Loading Level

Encapsulation efficiency of pcDNA was determined by comparing the quantity of pcDNA entrapped with the initial amount via fluorometry. The loading level of pcDNA was determined by assaying for pcDNA and BSA. The assay vias carried out by spectrophotometry at 492 mn.

Encapsulation efficiencies and loading levels of different formulation of microspheres were listed in Table 1.

TABLE 1

Encapsulation efficiency and loading level of pcDNA

| Different Formulation of Microspheres | Microsphere A | Microsphere B | |
|---|---|---|---|
| Encapsulation Efficiency (%) | 81.8 | 78.1 | 88.9 (BSA) |
| Loading Level (%) | 1.4 | 0.8 | 9.1 (BSA) |

(iii) Size and Surface Morphology or Microspheres Containing p43 LacZ pcDNA

The images of freeze dried microspheres were taken by electron microscopy (FIG. 1). The double emulsion/solvent extraction method yielded DNA-microspheres ranging in size between 5 and 30 $\mu$m.

(iv) Distribution of Plasmid DNA within the Microspheres

To visualize the DNA distribution, plasmid DNA (p43 LacZ) were stained with To Pro I (Molecular Probes, Eugene, Oreg.) and purified by gel filtration. The labeled DNA was encapsulated into the microspheres according to the same method as described in Example 1. The freeze-dried microspheres were examined under the confocal fluorescence microscope.

Figure 2:
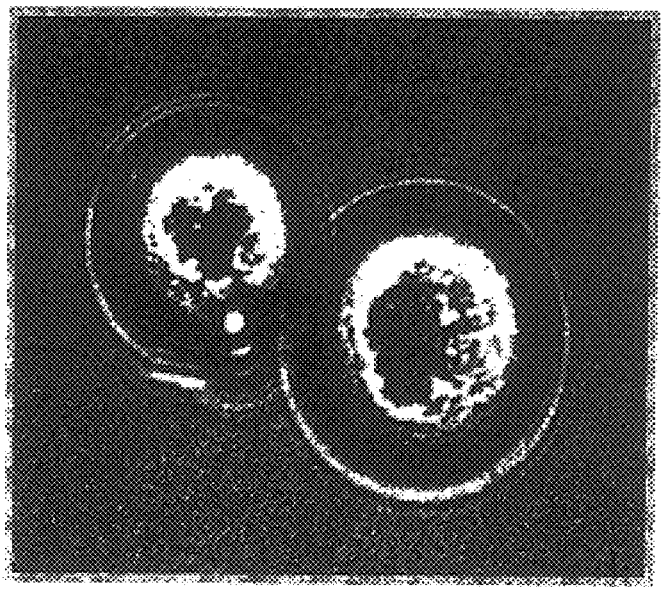
FIG. 2: Fluorescence image overlaid with phase contrast image.

The images were taken under phase contrast and confocal fluorescence filters respectively, and overlaid (FIG. 2). Fluorescence microscopy analysis revealed a shell structure with the DNA concentrated inside the core.

Figure 4:
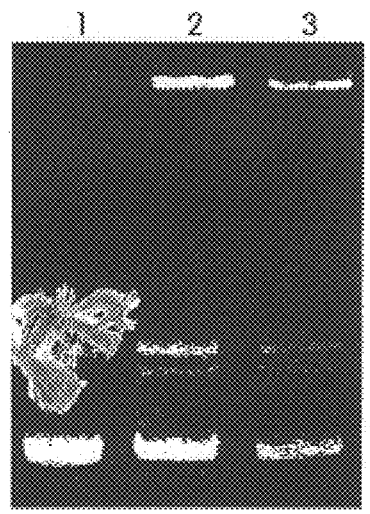
FIG. 4: Electrophoretic mobility of a DNA sample released from microsphere A. Lane1 is pcDNA, Lanes 2 and 3 are supernatant sample.

(v) In vitro Release of pcDNA from Microspheres at 37° C. Phosphate Buffered Saline (PBS, pH 7.4) and the Integrity of the Released DNA from the Microspheres Ten milligrams of microspheres were placed into 1 mL of PBS. The samples were incubated at 37° C. in a shaker. At various time points, samples were centrifuged and the supernatant was replaced with fresh PBS. The plasmid released was measured on a Hoefer fluorometer (FIG. 3). The supernatant was concentrated by ultrafiltration and separated on a 0.8% agarose gel (FIG. 4).

Release form Microsphere A formulation was bipliasic (FIG. 3). A burst of 7% of release was followed by a steady release of 19.6 ng/day.mg microspheres. In Microsphere B formulation, little burst and lag effect was observed. The release of DNA was relatively constant at an average rate of 29.3 ng/day.mg microspheres. Electrophoretic mobility analysis of the release DNA (FIG. 4) showed no degradation of the plasmid, indicating no damage during the encapsulation process.

(vi) Time Course of $\beta$-Gal Expression by the Injection of Microspheres Containing p43 LacZ into Balb/c Tibialis Muscle Balb/c mice (female, 8–10 week old, Charles River Labs, Wilmington, Mass.) were randomly grouped into five groups with 4 mice in each group. The test group received bilateral injections in the tibialis muscles of microspheres containing 5 $\mu$g pcDNA. Mice in the positive control group received 5 $\mu$g of plasmid per muscle. Blank microsphere injection and saline injection were given as negative controls. One mouse from each group was sacrificed at weeks 1, 3, 5, 7, respectively. The tibialis muscles were isolated, and fixed by 4% paraformaldehyde, permeabilized in 0.02% deoxycholate and 0.02% NP-40, and stained with Blue-Gal (Gibco-BRL) according to the manufacturer protocol. The muscles were cryo-sectioned, counter stained and coverslip mounted. Best sections were selected for the microphotograph.

Figure 5:
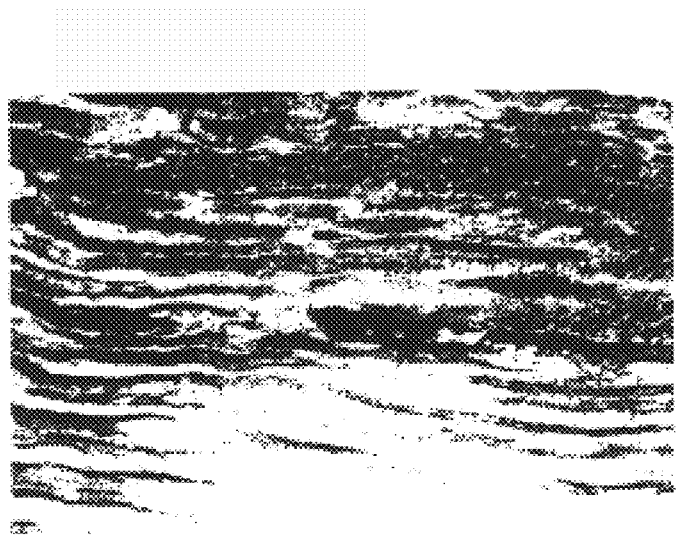
FIG. 5: β-galactosidase expression in mouse muscle after injection of DNA-microspheres.

Beta-Gal expression from the Microsphere B formulation could be detected at week 5 and increased at week 7 (A typical staining image is shown in FIG. 5). Very low expression was observed from the Microsphere A injection throughout the 7-week period. In contrast, naked DNA injection gave relatively high expression at week 1, bat became undetectable by week 5.

Figure 6:
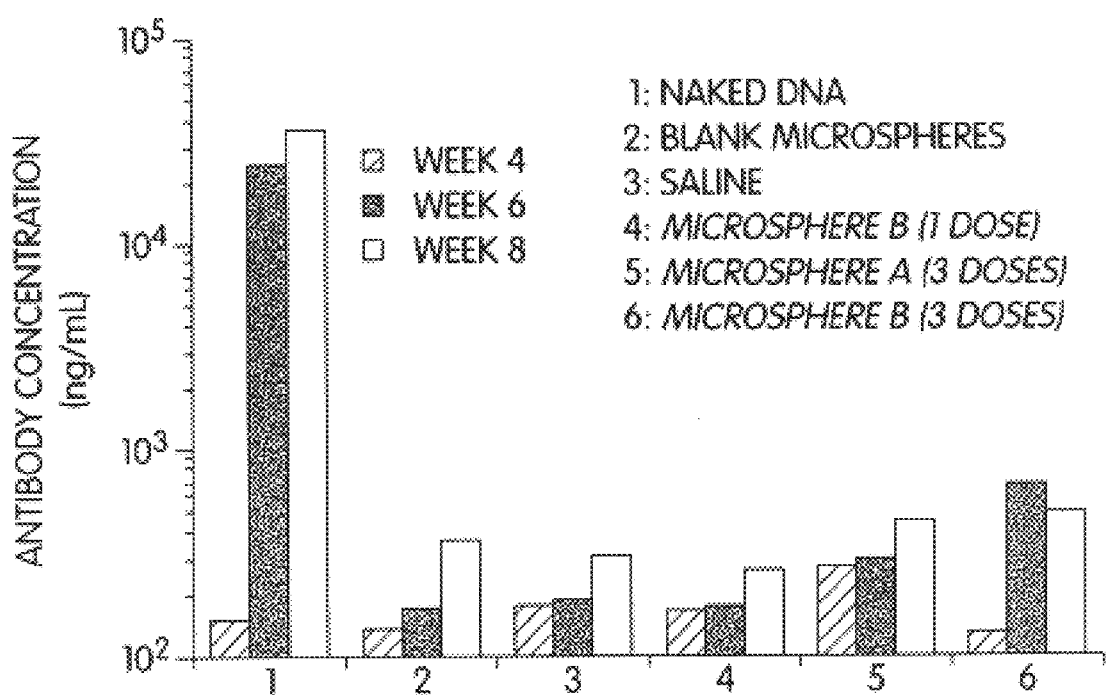
FIG. 6: Time course of anti-β-Gal IgG response in Balb/c mice.

(vii) Vaccination of Balb/c Mice by Injection of Biodegradable Microspheres Containing p43 LacZ Balb/c mice (female, 8–10 week old) were randomly grouped (4 mice in each group). They received primary injection of microspheres containing p43-LacZ plasmid containing 5 $\mu$g of plasmid at right flank in the tibialis muscle on day 0. Control groups were naked DNA, blank microspheres, or saline. Two booster injections with the same doses were given at weeks 2 and 4. One group of mice received only single injection of microspheres at the same dose. Blood samples were drawn from the tail vein at weeks 2, 4, 6 and 8. Serum was separated and analyzed for anti-$\beta$-galactosidase by ELISA (FIG. 6). CTL assay was performed at week 11 on lymphocytes harvested from the lymph nodes (inguinal and popliteal) and spleens from the immunized mice with $\beta$-Gal transfected syngenic spleenocytes (5:1 ratio of responder:stimulator cells, 5 days incubation with IL-2). Following the clonal expansion, the responder lymphocytes were incubated with $^{51}$Cr loaded and $\beta$-Gal transfected P815 target cells at various E:T ratios for 4 hours, and the percent lysis was calculated by counting the released $^{51}$Cr in the medium (FIG. 7).

Vaccination with Microsphere B formulation followed by two boosts of the same dose at biweekly intervals elicited a modest antibody response at week 6 and 8 (FIG. 6). A single injection did not stimulate any detectable antibody response within 8 weeks. Naked DNA vaccination following the same three-injection protocol at the same dose gave a much higher antibody response.

Figure 7:
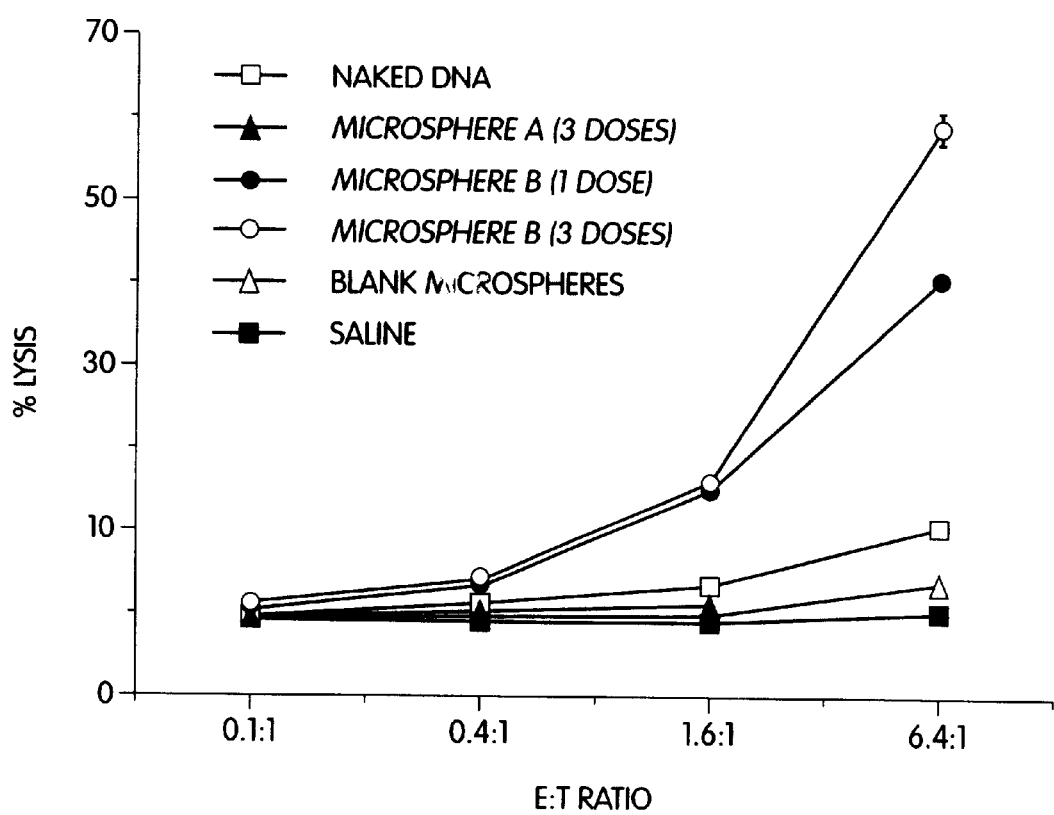
FIG. 7: Specific CTL response in Balb/C mice.

Although a single injection could not induce detectable response, it did elicit a strong CTL response when measured at week 11, even at a low E:T ratio of 6.4 (FIG. 7). The three-booster vaccination of Microsphere B generated the most potent CTL, but not the Microsphere A formulation. A moderate CTL was observed of the naked DNA group (three injections). which peaked at week 8 and then declined to background level at week 11.

(viii) Results and Discussion

The double-emulsion/solvent method yielded DNA-microspheres ranging in size between 5 and 30 μm. Two formulations of microspheres were prepared for different plasmid release profiles. Microsphere A contained 1.4% p43-LacZ by weight. Microsphere B contained 0.8% plasmid and 9.1% BSA coencapsulated to increase the release rate of plasmid. The plasmid encapsulation efficiency was 82 and 78% for Microsphere A and B, respectively. To visualize the DNA distribution, the plasmid was stained with TO-PRO1 before encapsulation. Fluorescence microscopy analysis revealed a shell structure with the DNA concentrated inside the core.

Release form Microsphere A formulation was biphasic (FIG. 1). A burst of 7% of release was followed by a steady release of 19.6 ng/day.mg microspheres. In Microsphere B formulation, little burst and lag effect was observed. The release of DNA was relatively constant at an average rate of 29.3 ng/day.mg microspheres. Electrophoretic mobility analysis of the release DNA (FIG. 4) showed no degradation of the plasmid, indicating no damage during the encapsulation process.

β-Gal expression from the Microsphere B formulation could be detected at week 5 and increased at week 7 (A typical staining image is shown in FIG. 5). Very low expression was observed from the Microsphere A injection throughout the 7-week period. In contrast, naked DNA injection gave relatively high expression at week 1, but became undetectable by week 5.

Vaccination with Microsphere B formulation followed by two boosts of the same dose at biweekly intervals elicited a modest antibody response at week 6 and 8 (FIG. 6). A single injection did not stimulate any detectable antibody response within 8 weeks. Naked DNA vaccination following the same three-injection protocol at the same dose gave a much higher antibody response.

Although a single injection could not induce detectable response, it did elicit a strong CTL response when measured at week 11, even at a low E:T ratio of 6.4 (FIG. 7). The three-booster vaccination of Microsphere B generated the most potent CTL, but not the Microsphere A formulation. A moderate CTL was observed of the naked DNA group (three injections), which peaked at week 8 and then declined to background level at week 11.

EXAMPLE 8

Intramuscular Delivery of LacZ Plasmid Encapsulated in P(DAPG-EOP) Microspheres (i) Preparation of P(DAPG-EOP) Microspheres Containing p43-LacZ P(DAPG-EOP) was prepared by a two step reaction. Several polymers with a weight average molecular weight between 8,000 and 35,000 were obtained. These polymers exhibited similar physico-chemical properties as P(LAEG-EOP). One P(DAPG-EOP) polymer with a Mw of 15,000 was used for the following microencapsulation study.

P(DAPG-EOP):

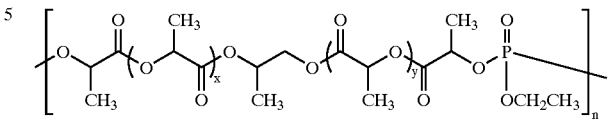

P(DAPG-EOP) microspheres containing p43-LacZ DNA were prepared according to the same method described in Example 7. One hundred microliter of pcDNA solution (10 mg/mL dissolved in TE buffer) was added to a solution of 50 mg of P(DAPG-EOP) in 1 mL of methylene chloride, and emulsified via sonication for 15 seconds. The resulting emulsion was poured into 5 mL of 1% polyvinyl alcohol (PVA) solution and vortexed for 1 minute. This emulsion was then poured into 20 mL of 0.3% PVA solution while stirring. An isopropanol solution (2%, 25 mL) was added and the mixture was kept stirring for 1 hr. The resulting microspheres were collected via centrifugation, washed with water and freeze dried. Microspheres containing both plasmid and bovine serum albumin (BSA) or mouse serum albumin (MSA) were prepared in similar manner by incorporating 10:1 (w/w) ratio of BSA or MSA in the plasmid solution.

(ii) Characterization of P(DAPG-EOP) Microspheres

P(DAPG-EOP) microspheres with or without bovine serum albumin, with two different loading levels were obtained. Their average sizes were relatively close, number average size ranged from 7 to 10 micrometers (Table 2 and FIGS. 8 and 9).

TABLE 2

| P(DAPG-EOP) microspheres containing LacZ plasmid with or without BSA | | |
|---|---|---|
| Microspheres | Encapsulation Efficiency (%) | Loading Level (%) |
| Mcsp C-1 (w/o BSA) | 94 | 0.93 |
| Mcsp C-2 (w/o BSA) | 92 | 1.84 |
| Mcsp D-1 (w/ BSA) | 88 | 0.85 |
| Mcsp D-2 (w/ BSA) | 90 | 1.80 |

(iii) In vitro Release of pcDNA from Microspheres

Five milligrams of microspheres were placed into 1 mL of PBS. The samples were incubated at 37° C. At various time points, samples were centrifuged and the supernatant was replaced with fresh PBS. The plasmid released was measured on a Hoefer fluorometer (FIG. 10). The supernatant was concentrated by ultrafiltration and separated on a 0.8% agarose gel (FIG. 11).

(iv) Vaccination with P(DAPG-EOP) Microspheres Containing p43-LacZ with or without BSA Balb/c mice (female, 8~10 week old) were randomly grouped (4 mice in each group). The test group received single injection of microspheres in the tibialis muscle at right flank containing 10 μg pcDNA (except that one of the groups received three injections of Mcsp D-2 containing 5 μg of plasmid at a biweekly interval). Mice in the positive control group received three injections of 5 μg of naked DNA at a biweekly interval. Microspheres containing pRE-Luciferase DNA (at the same dose of DNA) and saline injection were given as negative controls. Blood samples were drawn from the tail vein at week 8 and 11 and serum was collected. Serum samples from the mice in the same group were pooled together and analyzed for anti-β-galactosidase by ELISA. CTL assay was performed at week 11 on lymphocytes harvested from the lymph nodes (inguinal and popliteal) and spleens from the immunized mice with β-Gal transfected syngenic spleenocytes (5:1 ratio of responder:stimulator cells, 5 days incubation with IL-2). Following the clonal expansion, the responder lymphocytes were incubated with $^{51}$Cr loaded and β-Gal transfected P815 target cells at various E:T ratios for 4 hours, and the percent lysis was calculated by counting the released $^{51}$Cr in the medium.

(v) Results and Discussion for Example 8

(a) Preparation of P(DAPG-EOP) Microspheres Containing LacZ Plasmid

In order to achieve a faster release of plasmid DNA from the microspheres, we have tested P(DAPG-EOP) [Mw=15 Kda, structure shown above] as the matrix material, because P(DAPG-EOP) was likely to degrade faster than P(LAEG-EOP). A separate study showed that the molecular weight of P(DLAPD-EOP), between 8K to 21K, did not significantly affect the encapsulation efficiency of macromolecules. P(DLAPD-EDP) with MW15K was chosen for the following studies. With similar size distribution and surface morphology, microspheres with loading level up to about 2% were successfully prepared according to the above protocol. Mcsp C-2 and Mcsp D-2 had 1.84% and 1.80% p43-LacZ DNA loaded, respectively. Mcsp D-2 also contained 9% BSA.

Double emulsion/solvent extraction method was used to formulate microspheres. Under the optimized condition, high encapsulation efficiency (over 90%, analyzed by fluorometry) of pcDNA was achieved at 1–2% target loading level. Higher loading level of plasmid was hard to achieve because of the high viscosity of plasmid DNA solution at concentration of 10 mg/mL). In a different formulation (Mcsp D), protein excipient was coencapsulated to increase the release rate of plasmid DNA. The encapsulation efficiencies of plasmid in all cases were from 88% to 94%.

Figure 8A:
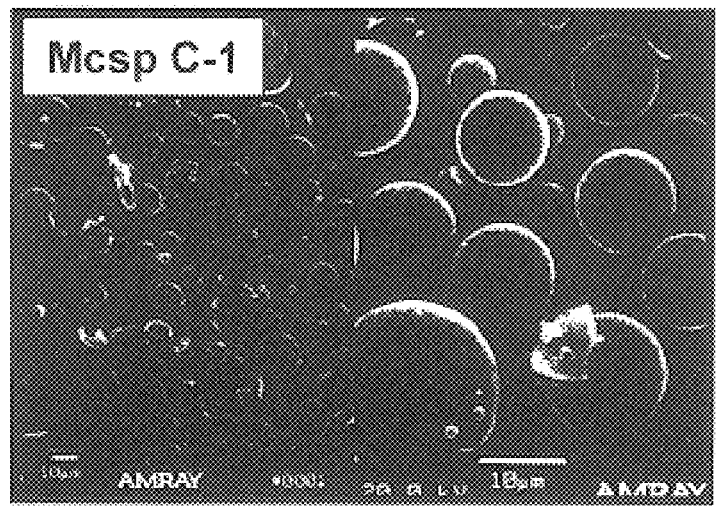
FIG. 8: EM images of PPE microspheres containing p43-LacZ DNA without BSA (Mcsp C) and with BSA (Mcsp D).
Figure 8B:
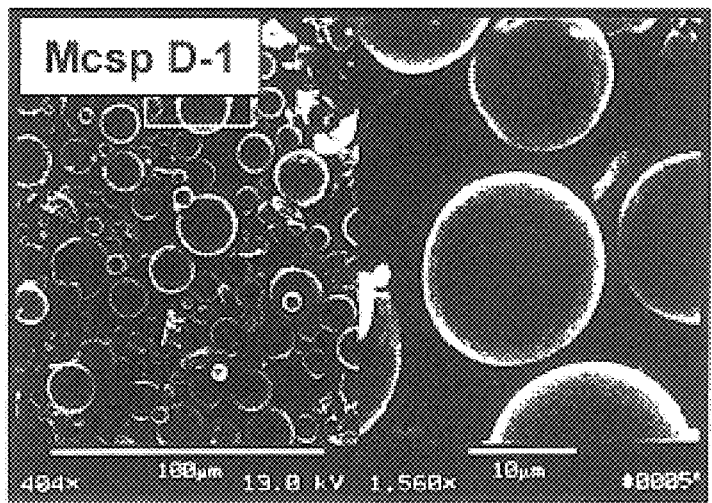
Figure 9A:
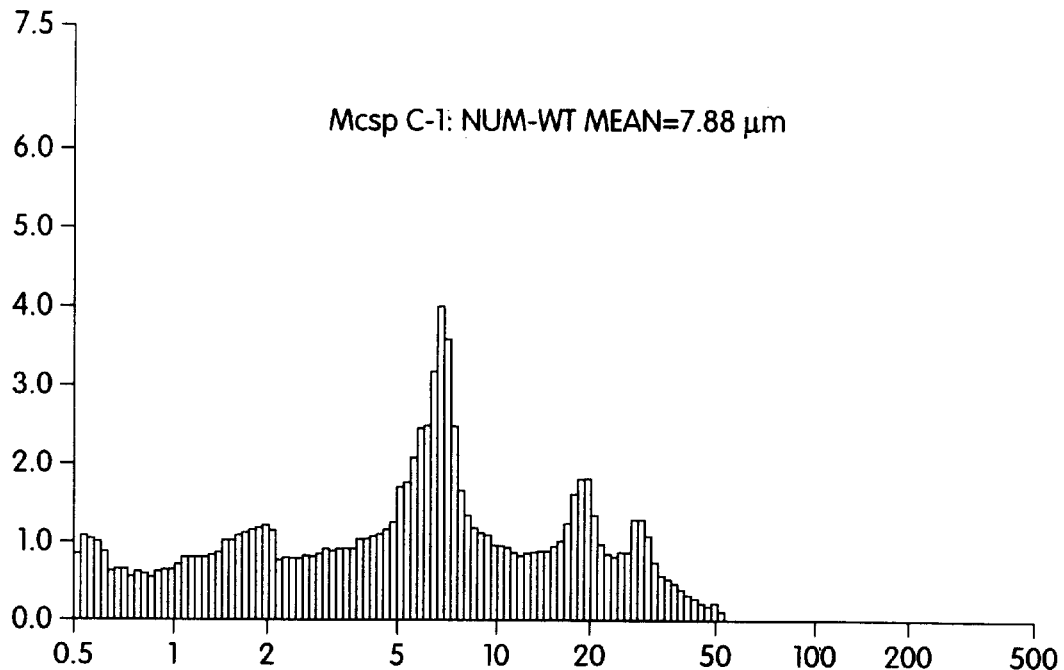
FIG. 9: Size distribution of PPE microspheres containing p43-LacZ DNA with or without BSA.
Figure 9B:
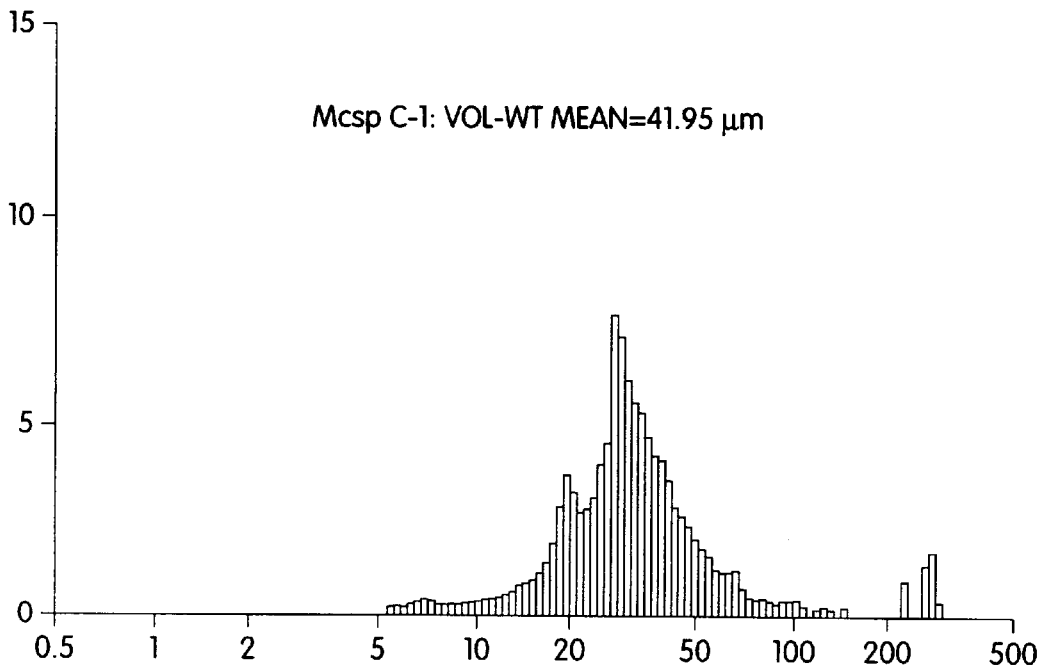
Figure 9C:
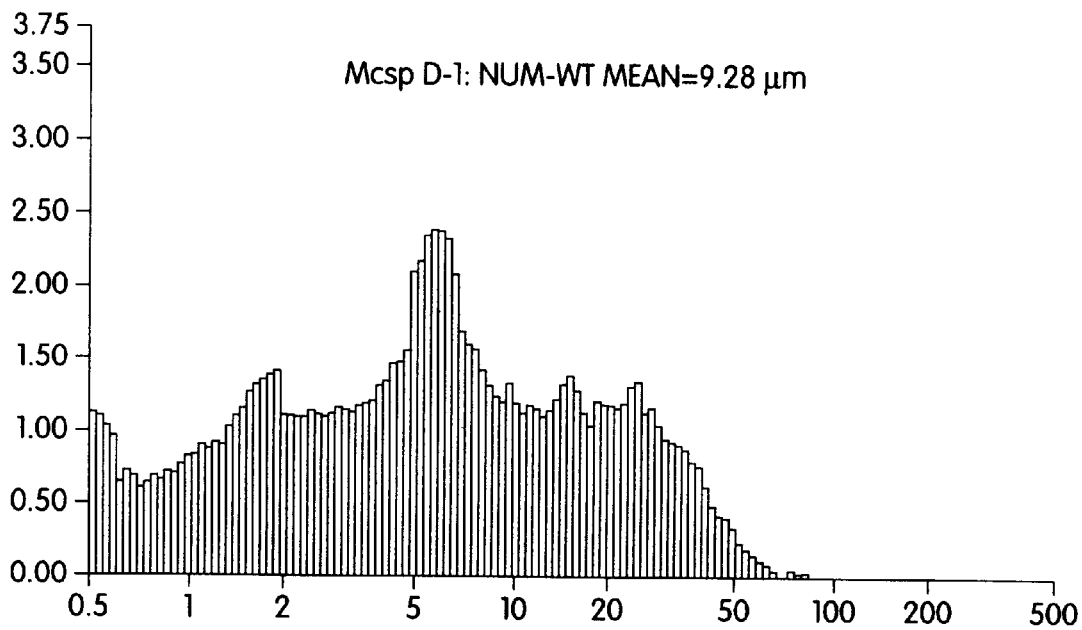
Figure 9D:
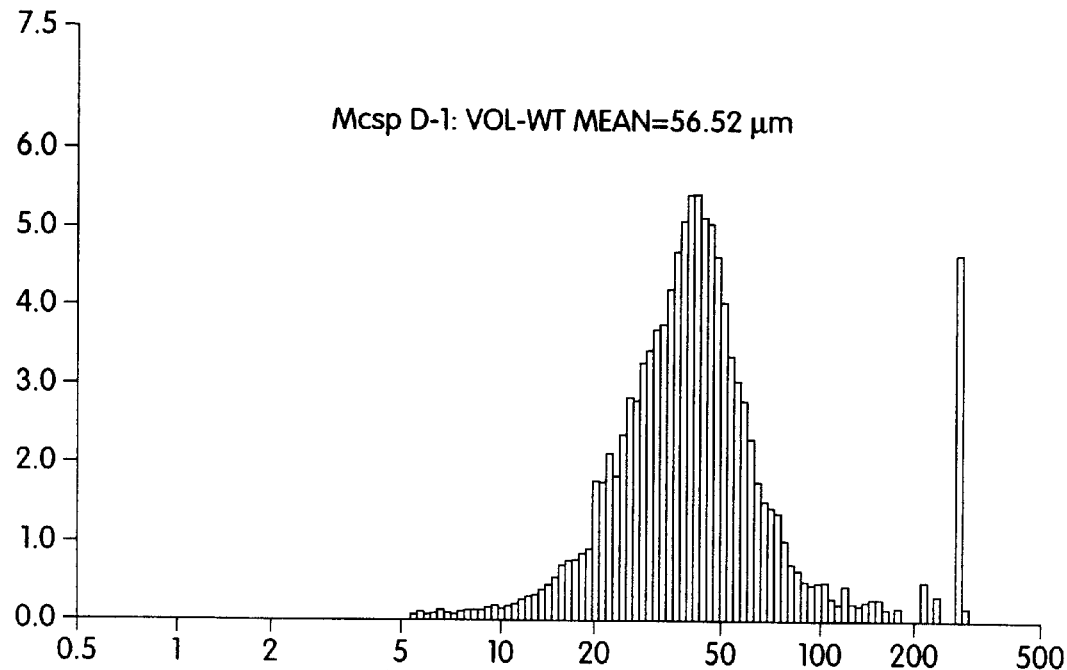

P(DAPG-EOP) microspheres prepared by this method showed a relatively smooth surface morphology (FIG. 8). The number and weight average size of Mcsp C-1 is 7.88 pm and 41.95 μm, respectively (FIG. 2); whereas 9.28 μm and 56.52 μm were for that of Mcsp D-1.

As expected, release rates of plasmid DNA from the P(DAPG-EOP) microspheres containing both p43-LacZ DNA and BSA were much higher than that with plasmid DNA only (FIG. 10). DNA release rate from Mcsp C-2 was six times higher than that from Mcsp C-1; whereas Mcsp D-2 released DNA at a rate 13 times higher than Mcsp D-1. Electrophoretic mobility analysis of the DNA released from Mcsp D-2 containing LacZ plasmid and MSA at the same loading level indicated that the plasmid released from the microspheres remained its integrity. No smear pattern, which indicated DNA degradation, was observed (FIG. 11).

b) Vaccination with P(DAPG-EOP) Microsphere, Containing p43-LacZ

The P(DAPG-EOP) microspheres (C-2 and D-2) were tested followed a similar protocol as in Example 7.

TABLE 3

Polymer: P(DAPG-EOP), Mw = 15 K.
Plasmid: p43-LacZ.
Loading level: Mcsp C-2: 1.84%, Mcsp D-2: 1.80%, Mcsp F-2: 1.80%

| | | Time after immunization (Weeks) | | | | |
|---|---|---|---|---|---|---|
| Group | Dose | 0 | 2 | 4 | 8 | 11 |
| Naked DNA | 5 μg | ✓ | ✓ | ✓ | ELISA for Serum Antibody | ELISA for Serum Antibody & CTL assay |
| Mcsp C-2 (LacZ) | 10 μg | ✓ | | | (same) | (same) |
| Mcsp D-2 (LacZ-BSA) | 10 μg | ✓ | | | (same) | (same) |
| Mcsp D-2/3 Doses | 5 μg | ✓ | ✓ | ✓ | (same) | (same) |
| Mscp F-2 (Luciferase) | 10 μg | ✓ | | | (same) | (same) |
| Saline | 40 μL | ✓ | | | (same) | (same) |

Figure 12A:
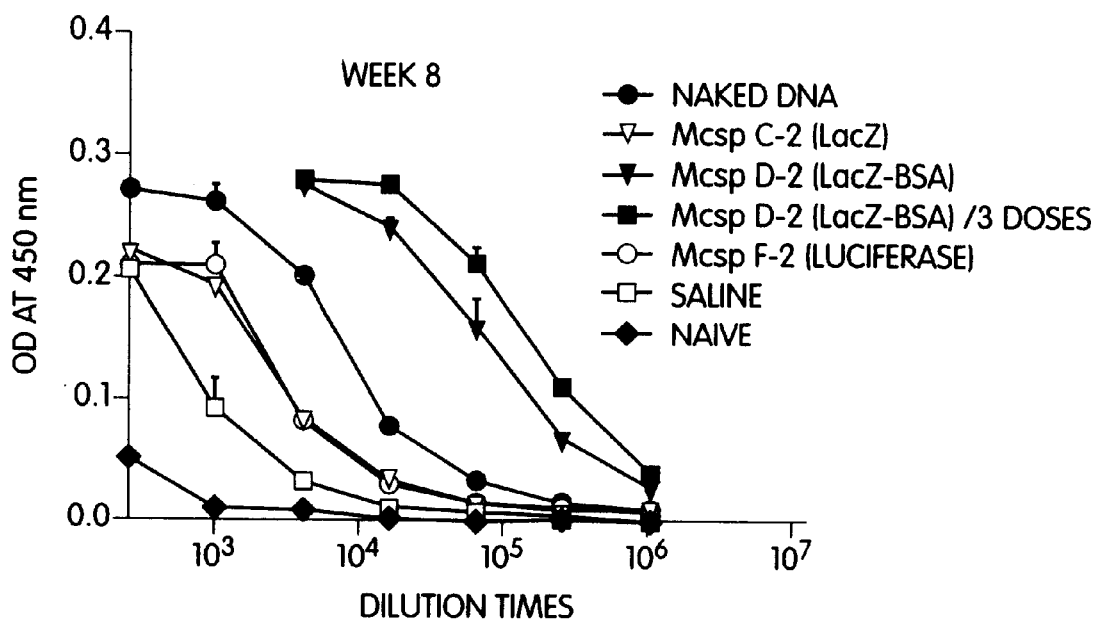
FIG. 12: β-Galactosidase-specific antibody response.
Figure 12B:
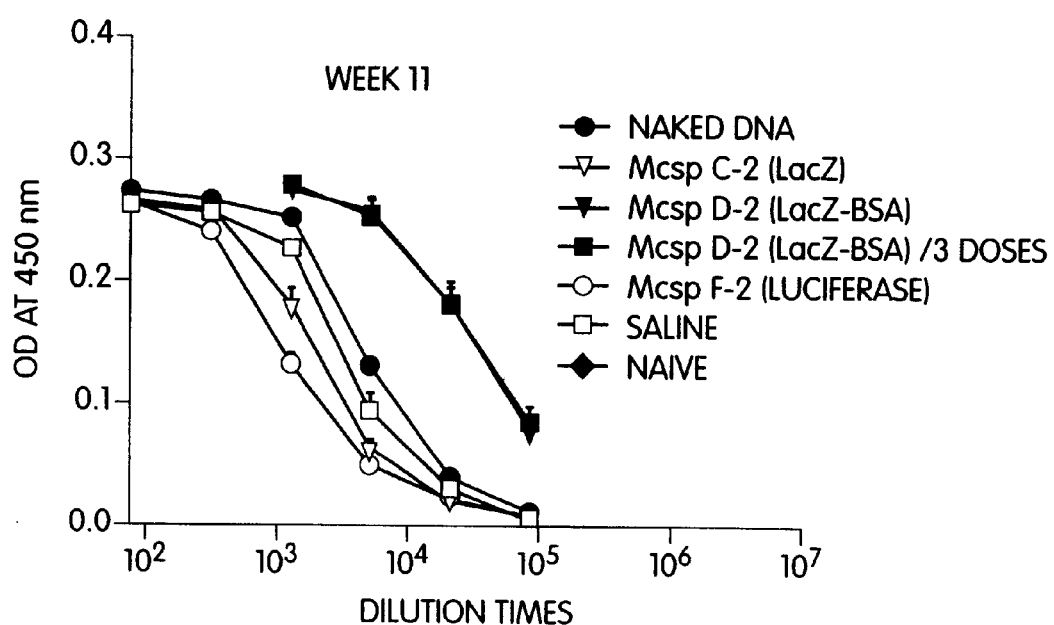
Figure 13:
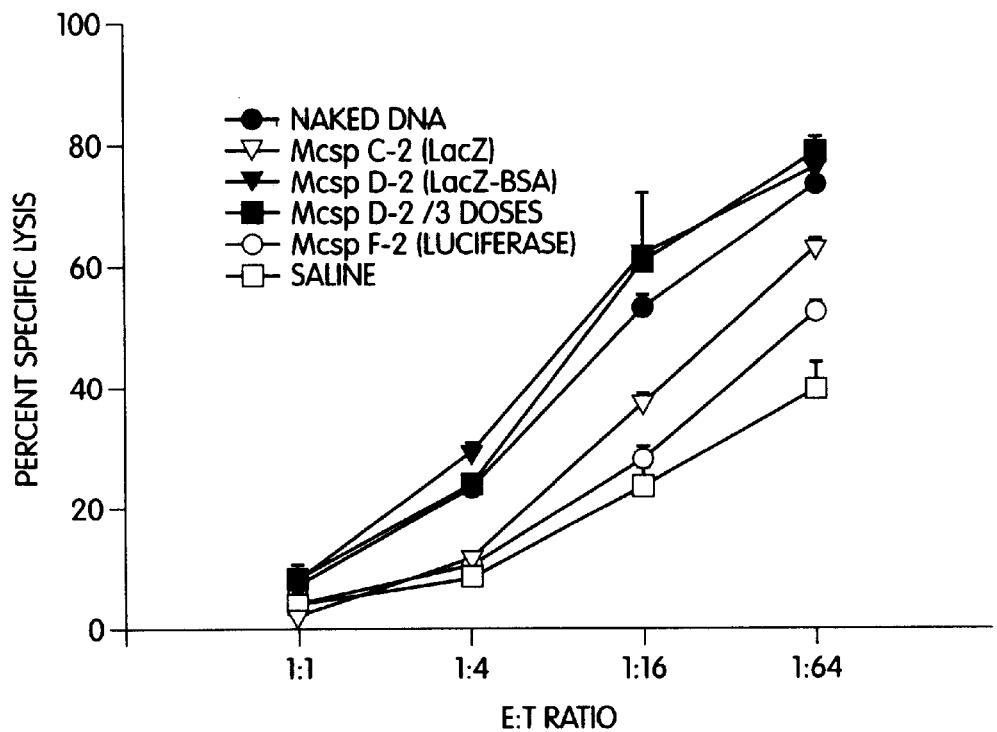
FIG. 13: β-Galactosidase-specific CTL response at week 11.
Figure 14:
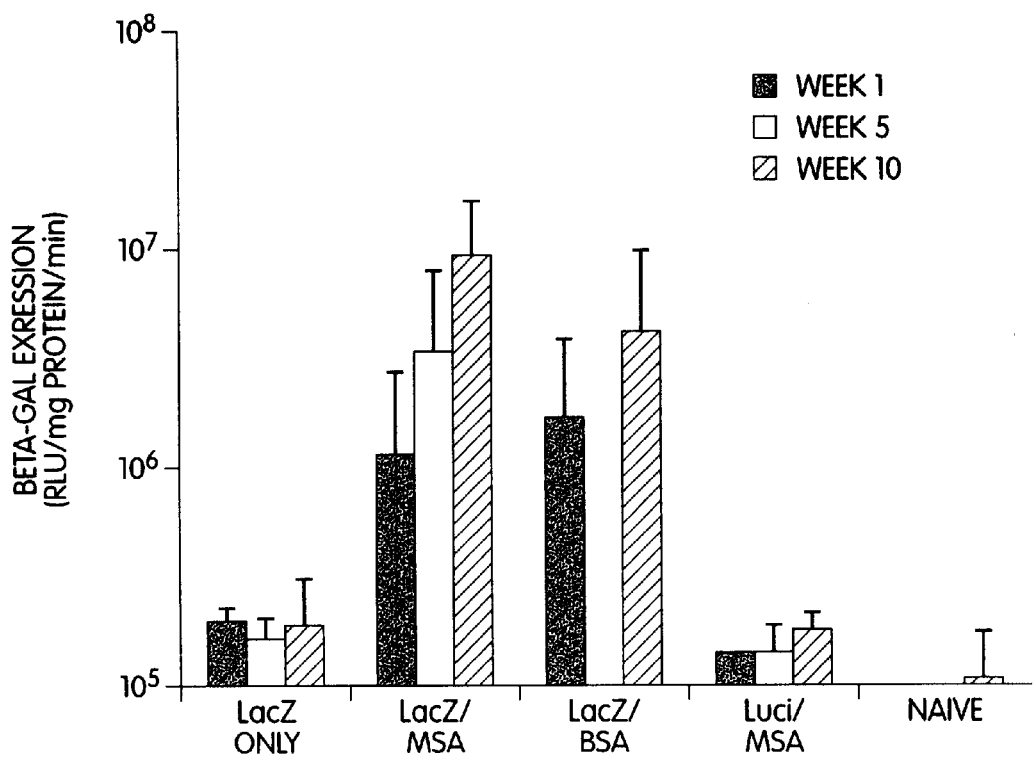
FIG. 14: β-Galactosidase expression in mouse tibialis muscle following single injection of microspheres.

Mcsp C-2 and Mcsp D-2 containing 10 μg of plasmid was given as a single injection. One group of mice received three doses of Mcsp D-2 containing 5 μg of DNA at biweekly intervals. Naked DNA control group (three injection of 5 μg of naked DNA at biweekly intervals) generated moderated level of anti-μ-Gal antibody. At both the week 8 and week 11 time points, higher antibody responses were observed in both groups that received the single dose and three injections of Mcsp D-2. Mcsp C-2 did not give any detectable antibody response (FIG. 12). The same trends were observed in the CTL assay performed at week 11 (FIG. 13), One dose and three-dose protocol resulted in the similar CTL response as the naked DNA control (three-injection protocol).

EXAMPLE 9

P(DAPG-EOP) Microsphers Containing both LacZ Plasmid DNA and IFN-γ

(i) Coencapsulation of LacZ Plasmid with IFN-γ

P(DAPG-EOP) microspheres containing LacZ plasmid and IFN-γ were prepared according to the same protocol described in Example 8, except that the IFN-γ was incorporated into the MSA solution before the preparation. All microspheres contained 9% MSA. The loading levels of DNA and IFN-γ were controlled to about 1.8% and 0.1% respectively. The number average size of the microspheres was 8–10 μm and volume average size was 42 to 57 μm.

The in vitro release conducted in PBS at 37° C. showed that microspheres containing both DNA and MSA had an average DNA release rate of 380 ng/day/mg of microspheres, similar to the microspheres containing both LacZ DNA and BSA, compared with 125 ng/day/mg of microspheres released from microspheres containing DNA alone.

TABLE 4

P(DAPG-EOP) microspheres containing LacZ plasmid, MSA and/or IFN-γ

| Microspheres | p43-LacZ | IFN-γ | MSA |
|---|---|---|---|
| Mcsp H | 1.84% | — | 9% |
| Mcsp J | 1.8% | 0.1% | 9% |
| Mcsp K | | — | 0.1% |

(ii) Expression of β-galactosidase in Mouse Tibialis Muscle

Balb/c mice (female, 8~10 weeks old) were randomly grouped and injected in the tibialis muscles with different groups of microspheres containing 5 µg of pcDNA (see FIG. 2 for group description). Microspheres containing pRE-Luciferase plasmid (instead of p43-LacZ) were used as a control. Two mice from each group were sacrificed at weeks 1, 5 and 10, respectively. The tibialis muscles were isolated, homogenized and analyzed for P-galactosidase using a chemiluminescent detection kit (Tropix, Inc., Mass.).

(iii) Vaccination of Balb/c Mice with Microencapsulated p43-LacZ Containing both LacZ Plasmid and IFN-γ

Figure 15:
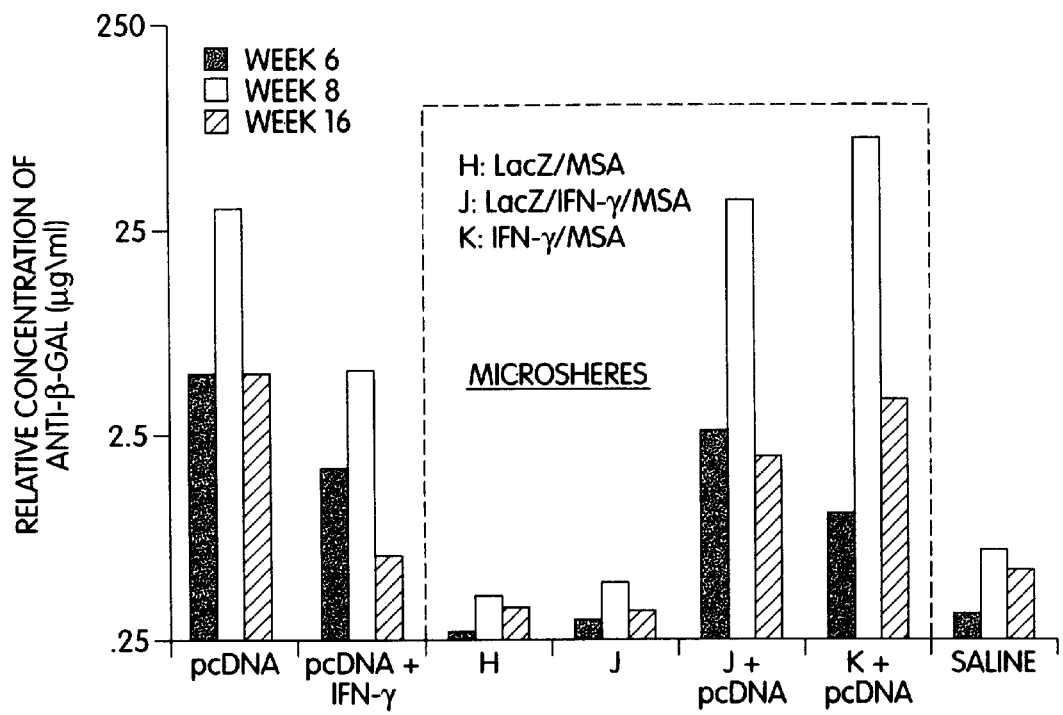
FIG. 15: Anti-β-Galactosidase concentration in mice serum (monoclonal β-galactosidase antibody as standard) measured by ELISA.

Four microsphere groups were tested (see Table 4 and FIG. 15). A single injection of microspheres equivalent to 15 µg of DNA was given for Mcsp H and Mcsp J groups. The same amount of microspheres plus 15 µg of naked DNA were injected for Mcsp K group. A mixture of Mcsp J (equivalent to 10 µg of DNA) and 5 µg of naked DNA were given for another group. A mixture of 15 µg of DNA and 800 ng IFN-γ (equivalent amount in Mcsp J and Mcsp K) were as 1:5 used as a control. Positive and negative controls were three injections of naked DNA (5 µg each) and saline, respectively, given at biweekly intervals. Blood samples were drawn from the tail vein at weeks 6, 8, and 16. Serum was separated and analyzed for anti-β-galactosidase by ELISA. The CTL assay was performed at week 10 on lymphocytes harvested from the lymph nodes and spleens from the immunized mice.

(iv) Results and Discussion for Example 9

Beta-Gal expression was analyzed by a quantitative chemluminescence assay. Microspheres with p43-LacZ alone gave very low expression, although the expression could be detected by immunohistochemistry. Microspheres containing both DNA and protein yielded a β-Gal expression 10 to 100 times higher than background level. Expression resulting from the injection of microspheres containing either DNA/BSA or DNA/MSA was not statistically different. The gene expression level of microspheres was lower than naked DNA injection at the same dose. This may be due to the low DNA concentration presented at the injection site, due to the slow release of plasmid from microspheres.

Figure 16:
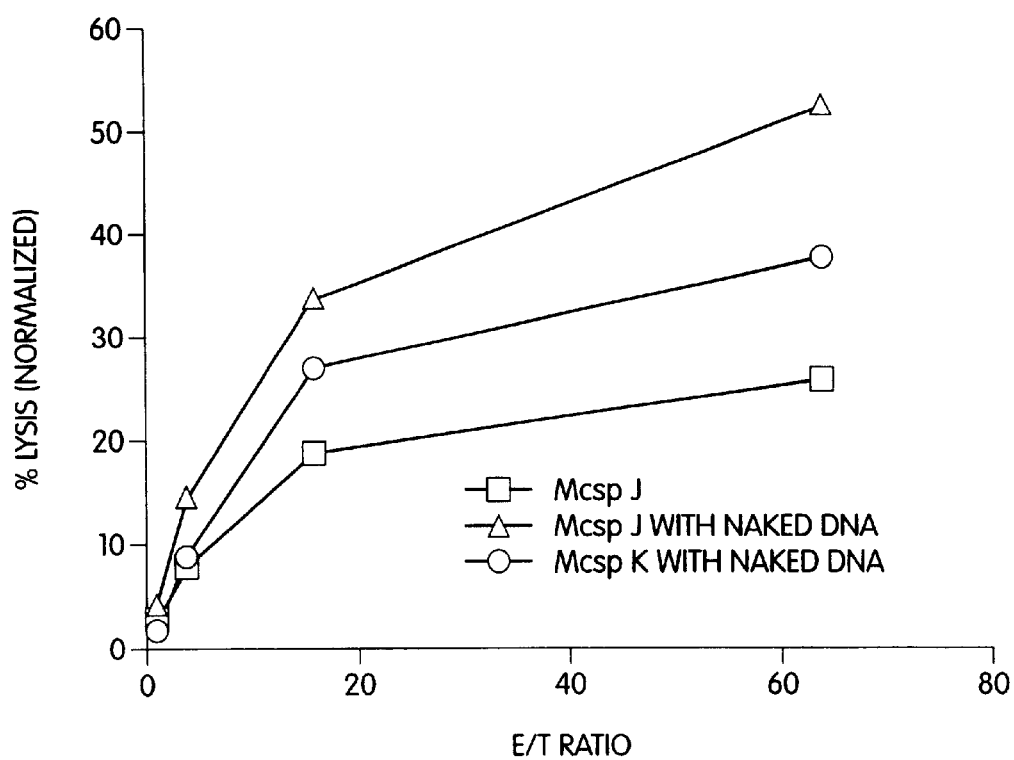
FIG. 16: Percent lysis determined in a 4-hour $^{51}$Cr release assay for CTLs obtained from mice immunized with a single injection of microspheres.

We have shown previously that vaccination with a single injection of microspheres containing BSA and p43-LacZ could generate similar CTL responses and antibody responses as three injections of naked DNA at the same total dose. In this present study, IFN-γ was co-encapsulated into microspheres as an adjuvant, and BSA was replaced with MSA (9%) to eliminate any possible immune adjuvant effect from BSA (Table 4 and FIG. 15). It was found that either Mcsp H or Mcsp J alone gave a poor antibody response, but when injected with naked DNA, Mcsp J (total dose of DNA remained 15 µg) elicited an antibody response comparable to naked DNA vaccination following the three-injection protocol, with a peak at week 8. Interestingly, injection of 15 µg of naked DNA in combination with microspheres containing only IFN-γ and MSA (Mcsp K) generated the similar level of antibody response, significantly higher than if both were injected in free form (FIG. 15). Intramuscular injection of Mcsp J alone elicited a relatively low CTL response (FIG. 16), which was unexpected because IFN-γ was reported to selectively enhance the Th1 response. The combination of naked DNA with either Mcsp J or Mcsp K generated a relatively higher CTL response. These results suggested the importance of a high initial dose of plasmid DNA for DNA vaccine for a DNA vaccine to generate a potent immune response.

EXAMPLE 10

Immunization of Balb/c Mice with P(DAG-EOP) Microspheres Containing LacZ DNA and IL-4 or IFN-γ

(i) Preparation of Microspheres Containing LacZ Plasmid and IFN-γ or IL-4

Microspheres containing LacZ plasmid DNA and IFN-γ or DNA and IL-4 were prepared according to the protocol described in Example 8. No protein excipient was used in these microspheres. The encapsulation efficiency, loading level and size of the microspheres were similar to the microspheres prepared in Examples 7 and 8.

TABLE 5

P(DAPG-EOP) microspheres used in this Example.

| Microspheres | Encapsulation Efficiency (%) | Loading Level (%) |
| --- | --- | --- |
| Mcsp C-2: DNA | 80–95 | 1.6–1.9 |
| Mcsp M: DNA/IFN-γ (no excipient) | 78 (DNA) | 1.56 |
| Mcsp L: DNA/IL-4 (no excipient) | 71 (DNA) | 1.42 |

(ii) Vaccination of Balb/c Mice with Mcsp C-2, Mcsp L and Mcsp M

Six groups of 3 mice were studied: three experimental groups contained mice injected with either Mcsp C-2 (containing LacZ DNA only), Mcsp L [containing LacZ and IFN-g (1060 IU)], or Mcsp M [containing LacZ and IL-4 (961 IU)] (Table 5). Each mouse in these experimental groups received microspheres equivalent to a total of 15 ug of LacZ DNA in saline. The positive control consisted of mice receiving 3 injections of 5 mg LacZ at a biweekly intervals, while the two negative controls contained naive: mice (no treatment) and saline-injected mice. All immunizations were intramuscular injections into the anterior tibialis muscle. Anti-β-Gal antibody response at weeks 6, 9, 1 0 and 12 were analyzed according to the method described in Examples 8 and 9.

Figure 17:
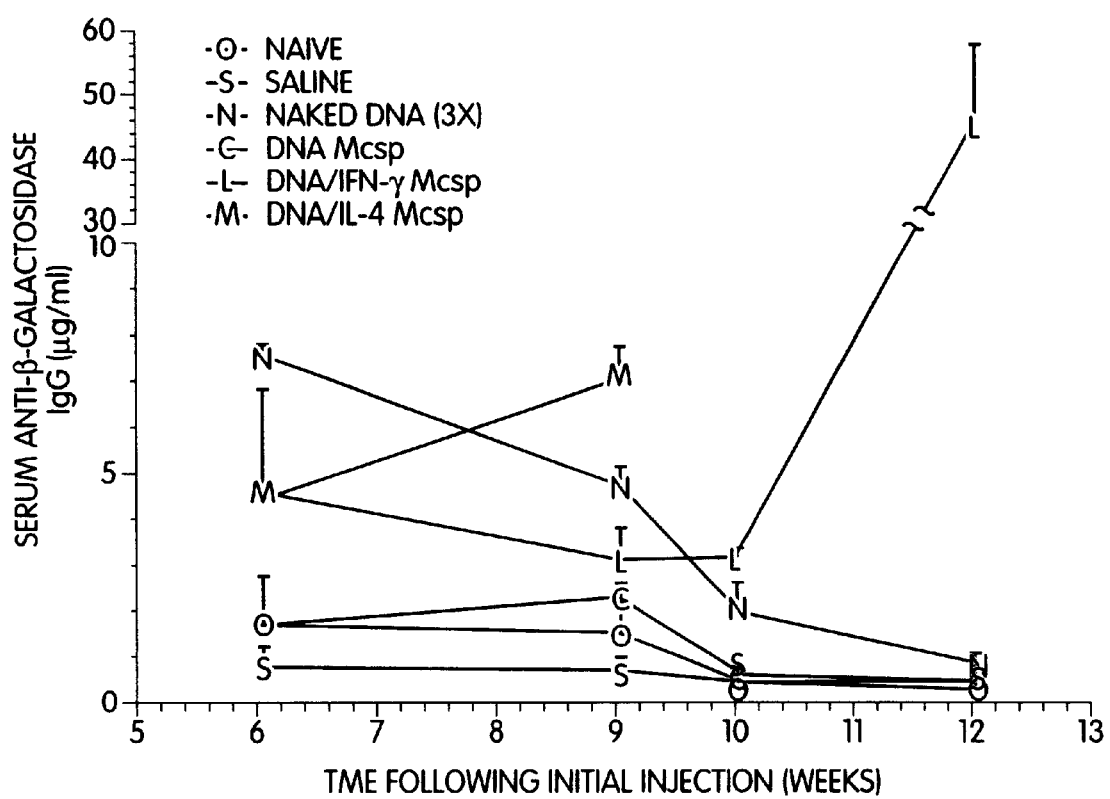
FIG. 17: Mouse serum anti-β-galactosidase IgG response following the immunization with P(DAPG-EOP) microspheres containing both LacZ plasmid and cytokines.

Consistent with Example 9, the phenomenon that a sustained delivery of IFN-γ would boost the antibody response was also confirmed in this study. This was in contrast to the expected result as shown in a bolus administration of IFN-γ, where the cytokine would enhance the Th1 type response and suppress the Th2 type immune response. FIG. 17 showed the serum β-gal-specific IgG measured at weeks 6, 9, 10, and 12 following the initial injections in the IL-4/IFN-γ microsphere experiment. The two negative controls, naive mice and saline-injected mice, showed IgG concentrations of less than 2.3 µg/mL for the duration of the experiment, as did the microspheres containing just DNA. The positive control (naked DNA) showed serum β-gal-specific IgG concentration at 7.6±0.22 µg/mL for week 6, but decreased to 0.8±0.26 µg/mL at week 12. Microspheres containing DNA/IL-4 and DNA/IFN-γ induced similar IgG concentrations at week 6 (4.6±2.2 and 4.4±2.4 µg/mL, respectively), but these concentrations differed significantly at later time points. IgG responses induced by DNA/IL-4 microspheres increased to 7.0±0.73 µg/mL at week 9 whereas IgG responses to DNA/IFN-γ microspheres increased dramatically from 3.1±0.21 µg/mL at week 11) to 44.1±13.1 µg/mL at week 12.

Comments on Examples 8–10

An extracellular gene delivery system based on biodegradable poly(phosphoester) microspheres prepared by double emulsion method wa; demonstrated. Bovine serum albumin could be co-encapsulated to increase the DNA release rate. Polymer structure and molecular weight, fabrication method, and loading levels of plasmid would also affect the plasmid DNA release kinetics.

The pattern of β-galactosidase expression, both temporal and spatial, in mouse tibialis muscle appeared to be different from that induced by naked DNA. In time points up to 7 weeks, the gene expression was at a lower level compared to naked DNA at the same dose. Intramuscular administration of PPE microspheres containing LacZ plasmid generated strong CTL response against β-galactosidase as a model antigen. A significantly higher antibody response than that of naked DNA was generated in the faster release version of microspheres (Mcsp D-2). Both humoral and cellular immune responses appeared to be more potent than that elicited by naked plasmid at the same dose.

The materials, methods and examples are illustrative only and not intended to be limiting.

REFERENCES

In addition to the publications, patent applications, patents and other references mentioned above, the following such items listed below are incorporated by reference in their entirety. In case of conflict, the present application, including definitions, will control.

Patents and Patent Applications

U.S. Pat. No. 5,869,103
U.S. Pat. No. 5,783,567
U.S. Pat. No. 5,256,765
U.S. Pat. No. 3,887,699
U.S. Pat. No. 4,293,539
U.S. Pat. No. 5,531,925
U.S. Pat. No. 5,407,609
U.S. Pat. No. 5,160,745
U.S. Pat. No. 5,075,109
U.S. Pat. No. 4,818,542
U.S. Pat. No. 4,741,872

Publications and Other References

Alpar et al., (1997) Biochemical Society Transactions, 25 (2);
Jones et al., (1977) Vaccine 15(8): 814–817;
Pretula et al., (1990) Makromol. Chem. 191, 671–680;
Pardoll, D, (1995) Annu. Rev. Immunal. 13:399–415;
Kadlyala et al., (1995) Biomedical Applications of Synthetic Biodegradable Polymers, 33–57;
Wloch et al., (1998) Human Gene Therapy, 9:1439–1447;
Rhine et al., (1980) Journal of Pharmaceutical Sciences, 69(3): 265–270;
Langer et al., (1981) Journal of Biomedical Materials Research, 15:267–277;
Odian, G., (1981) Principles of Polymerization, $2^{nd}$ ed.;
Heard, R, (1994), HLA & Disease, 123–51, Academic Press, New York,
Cell 80, 710 (1995);
Cell 67, 869877 (1991);
JEM 181, 18351845 (1995)

EQUIVALENTS

Those skilled in the art will recognize, or be able to ascertain using no more than routine experimentation, numerous equivalents to the polymers, nucleic acids, compositions, materials methods, uses, assays and reagents described herein. Such equivalents are considered to be within the scope of this invention.

We claim:

1. A composition for delivery of a nucleic acid, comprising: a nucleic acid formulated in a biocompatible polymer having recurring monomeric elements in said polymer represented in general formula (XV):

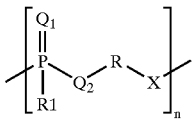

Formula XV wherein, independently for each occurrence:
$Q_1$ represents O or S;
$Q_2$ represents O, S or NR';
X represents O, S or NR';
n is an integer of about five or more;
R' represents H or alkyl;
R represents an organic or organometallic moiety;
R1 represents hydrogen, alkyl, —O-alkyl, —O-cycloalkyl, aryl, —O-aryl, heterocycle, —O-heterocycle, —S—R4, —O—(C=O)—R4, —Cl or —N(R2)R3;
R2 and R3, each independently, represent a hydrogen, an alkyl, an alkenyl, —(CH2)n-R4, or R2 and R3 taken together with the N atom to which they are attached complete a heterocycle having from 4 to about 8 atoms in the ring structure; and
R4 represents a hydrogen, aryl, cycloalkyl, cycloalkenyl, heterocycle or polycycle.

2. The composition of claim 1, wherein at least about 50 percent of said polymer comprises said monomeric elements in Formula XV.

3. The composition of claim 2, wherein $Q_1$, $Q_2$, and X represent O.

4. The composition of claim 1, wherein at least about 75 percent of said polymer comprises a single type of said monomeric element in Formula XV.

5. The composition of claim 4, wherein $Q_1$ represents O.

6. The composition of claim 4, wherein X represents O.

7. The composition of claim 4, wherein $Q_1$ represents O and $Q_2$ represents O.

8. The composition of claim 4, wherein R1 represents H, a lower alkyl, —O-lower alkyl, or —O-cycloalkyl.

9. The composition of claim 4, wherein said composition is provided as particles.

10. The composition of claim 9, wherein said particles are microspheres, and wherein said nucleic acid induces an immunogenic effect upon administration of said microspheres to a subject.

11. The composition of claim 10, wherein said nucleic acid is released from said composition upon degradation of said biocompatible polymer.

12. The composition of claim 4, wherein said composition further comprises an adjuvant.

13. The composition of claim 12, wherein said adjuvant is a cytokine.

14. The composition of claim 4, wherein said composition further comprises a filler.

15. The composition of claim 4, wherein said composition further comprises a therapeutic agent.

16. The composition of claim 4, wherein said nucleic acid constitutes at least about 1% of the composition.

17. The composition of claim 4, wherein said polymer consists essentially of a single type of said monomeric element in Formula XV, and wherein n is from about 5 to about 500.

18. The composition of claim 1, wherein said polymer has a molecular weight of at least about 5000 daltons.

19. The composition of claim 4, wherein said polymer has a molecular weight of at least about 7500 daltons.

20. The composition of claim 17, wherein said polymer has a molecular weight of at least about 10000 daltons.

21. A method for causing ectopic expression of a recombinant gene in myocytic cells of an animal, comprising: administering to an animal, by intramuscular administration, a polymeric composition comprising a recombinant gene formulated in a biocompatible polymer having recurring monomeric elements in said polymer represented in general formula (XV):

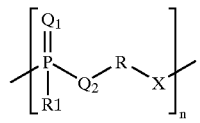

Formula XV wherein, independently for each occurrence:
- $Q_1$ represents O or S;
- $Q_2$ represents O, S or NR';
- X represents O, S or NR';
- n is an integer of about five or more;
- R' represents H or alkyl;
- R represents an organic or organometallic moiety;
- R1 represents hydrogen, alkyl, —O-alkyl, —O-cycloalkyl, aryl, —O-aryl, heterocycle, —O-heterocycle, —S—R4, —O—(C=O)—R4, —Cl or —N(R2)R3;
- R2 and R3, each independently, represent a hydrogen, an alkyl, an alkenyl, —(CH2)n-R4, or R2 and R3 taken together with the N atom to which they are attached complete a heterocycle having from 4 to about 8 atoms in the ring structure; and
- R4 represents a hydrogen, aryl, cycloalkyl, cycloalkenyl, heterocycle or polycycle, wherein said polymeric composition is administered in an amount sufficient to result in transfection of myocytic cells of said animal by said recombinant gene, thereby causing ectopic expression of a recombinant gene in myocytic cells of an animal.

22. The method of claim 21, wherein said polymer comprises almost entirely a single type of said monomeric element in Formula XV, and wherein n is from about 5 to about 500.

23. The method of claim 22, wherein said recombinant gene encodes a secreted protein.

24. The method of claim 23, wherein said secreted protein is a cytokine, growth factor, colony stimulating factor, interferon, or surface membrane receptor.

25. The method of claim 23, wherein said secreted protein is human growth hormone, growth hormone releasing hormone, insulin, insulin-like-growth factor, transforming growth factor-β, or vascular endothelial growth factor.

26. A method for preparing a biocompatible composition to transfect a cell in vivo, comprising combining a nucleic acid and a biocompatible polymer having recurring monomeric elements represented in general formula (XV):

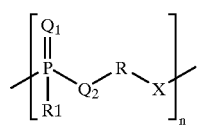

Formula XV wherein, independently for each occurrence:
- $Q_1$ represents O or S;
- $Q_2$ represents O, S or NR';
- X represents O, S or NR';
- n is an integer greater than about 5;
- R' represents H or alkyl;
- R represents an organic or organometallic moiety;
- R1 represents hydrogen, alkyl, —O-alkyl, —O-cycloalkyl, aryl, —O-aryl, heterocycle, —O-heterocycle, —S—R4, —O—(C=O)—R4, —Cl or —N(R2)R3;
- R2 and R3, each independently, represent a hydrogen, an alkyl, an alkenyl, —(CH2)n-R4, or R2 and R3 taken together with the N atom to which they are attached complete a heterocycle having from 4 to about 8 atoms in the ring structure; and
- R4 represents a hydrogen, aryl, cycloalkyl, cycloalkenyl, heterocycle or polycycle;

wherein a biocompatible composition is prepared.

27. The composition of claim 1, wherein R represents a substituted or unsubstituted cyclic, branched or straight chain aliphatic group of 2 to about 20 carbon atoms.

28. The method of claim 21, wherein R represents a substituted or unsubstituted cyclic, branched or straight chain aliphatic group of 2 to about 20 carbon atoms.

29. The method of claim 26, wherein R represents a substituted or unsubstituted cyclic, branched or straight chain aliphatic group of 2 to about 20 carbon atoms.

* * * * *